(12) United States Patent
Smith et al.

(10) Patent No.: US 11,779,585 B2
(45) Date of Patent: *Oct. 10, 2023

(54) METHOD FOR TREATING CORONAVIRUS INFECTIONS

(71) Applicant: OYAGEN, INC., Rochester, NY (US)

(72) Inventors: Harold C. Smith, Rochester, NY (US); Ryan P. Bennett, Clifton Springs, NY (US)

(73) Assignee: OYAGEN, INC., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/880,464

(22) Filed: Aug. 3, 2022

(65) Prior Publication Data

US 2022/0378815 A1 Dec. 1, 2022

Related U.S. Application Data

(63) Continuation of application No. PCT/US2021/016472, filed on Feb. 3, 2021.

(60) Provisional application No. 63/009,972, filed on Apr. 14, 2020, provisional application No. 62/987,846, filed on Mar. 10, 2020, provisional application No. 62/970,087, filed on Feb. 4, 2020.

(51) Int. Cl.

| | | |
|---|---|---|
| *A01N 43/04* | (2006.01) | |
| *A61K 31/70* | (2006.01) | |
| *A61K 31/519* | (2006.01) | |
| *A61P 31/14* | (2006.01) | |
| *A61K 31/706* | (2006.01) | |
| *A61K 31/7064* | (2006.01) | |
| *A61K 9/20* | (2006.01) | |
| *A61K 9/00* | (2006.01) | |
| *A61K 9/48* | (2006.01) | |

(52) U.S. Cl.
CPC .......... *A61K 31/519* (2013.01); *A61K 31/706* (2013.01); *A61K 31/7064* (2013.01); *A61P 31/14* (2018.01); *A61K 9/0019* (2013.01); *A61K 9/0043* (2013.01); *A61K 9/0053* (2013.01); *A61K 9/20* (2013.01); *A61K 9/4808* (2013.01)

(58) Field of Classification Search
None
See application file for complete search history.

(56) References Cited

U.S. PATENT DOCUMENTS

| | | | |
|---|---|---|---|
| 3,423,398 | A | 1/1969 | Rao |
| 6,232,282 | B1 | 5/2001 | Kvietok |
| 6,335,339 | B1 | 1/2002 | Arenas |
| 7,125,855 | B2 | 10/2006 | Bhat |
| 7,442,185 | B2 | 10/2008 | Amark |
| 8,038,649 | B2 | 10/2011 | Kronestedt |
| 8,062,255 | B2 | 11/2011 | Brunnberg |
| 8,075,517 | B2 | 12/2011 | Karlsson |
| 8,235,952 | B2 | 8/2012 | Wikner |
| 8,277,412 | B2 | 10/2012 | Kronestedt |
| 8,440,813 | B2 | 5/2013 | Babu |
| 8,475,804 | B2 | 7/2013 | Johansen |
| 8,529,510 | B2 | 9/2013 | Giambattista |
| 8,551,054 | B2 | 10/2013 | Guillermo |
| 9,724,360 | B2 | 8/2017 | Chun |
| 9,949,994 | B2 | 4/2018 | Chun |
| 10,479,996 | B2 | 11/2019 | Iversen |
| 10,548,971 | B2 | 2/2020 | Weiner |
| 11,617,753 | B2 | 4/2023 | Smith et al. |
| 2004/0259934 | A1 | 12/2004 | Olsen |
| 2010/0087388 | A1 | 4/2010 | Kotra |
| 2010/0172917 | A1 | 7/2010 | Ter Meulen |
| 2010/0233250 | A1 | 9/2010 | Baras |
| 2011/0028564 | A1 | 2/2011 | Johansen |
| 2011/0218210 | A1 | 9/2011 | Refaeli |
| 2012/0014911 | A1 | 1/2012 | Fuchs |
| 2016/0122374 | A1 | 5/2016 | Chun |
| 2016/0361330 | A1 | 12/2016 | Chun |
| 2017/0165230 | A1 | 6/2017 | Rudd |
| 2019/0255085 | A1 | 8/2019 | Clarke |
| 2019/0275063 | A1 | 9/2019 | Chun |
| 2019/0351048 | A1 | 11/2019 | Rauch |
| 2020/0017514 | A1 | 1/2020 | Plewe |
| 2020/0188404 | A1 | 6/2020 | Smith |
| 2021/0236497 | A1 | 8/2021 | Smith |

FOREIGN PATENT DOCUMENTS

| | | |
|---|---|---|
| WO | WO2005020885 | 3/2005 |
| WO | WO2009067409 | 5/2009 |
| WO | WO2002057287 | 7/2009 |

(Continued)

OTHER PUBLICATIONS

Agostini, Maria L., et al. "Coronavirus susceptibility to the antiviral remdesivir (GS-5734) is mediated by the viral polymerase and the proofreading exoribonuclease." MBio 9.2 (2018): e00221-18.*
U.S. Appl. No. 16/348,867, filed May 9, 2019.
U.S. Appl. No. 16/851,047, filed Apr. 16, 2020.
Cavins et al., "Initial toxicity study of sangivamycin (NSC-65346)," Cancer Chemotherapy Reports, 51(4):197-200 (1967).
Corman et al., "Detection of 2019 novel coronavirus (2019-nCoV) by real-time RT-PCR," Euro Surveillance, 25(30:2000045 (2020).
Dolloff et al., "Sangivamycin-like Molecule 6 Exhibits Potent Anti-Multiple Myeloma Activity through Inhibition of Cyclin-Dependent Kinase-9," Molecular Cancer Therapies, 11(11)L:2321-2330 (2012).

(Continued)

*Primary Examiner* — Patrick T Lewis
(74) *Attorney, Agent, or Firm* — HALEY GUILIANO LLP; James F. Haley, Jr.; Mihaela D. Danca

(57) ABSTRACT

Disclosed herein are methods, formulations, and kits for treating coronavirus infections, including Severe Acute Respiratory Syndrome coronavirus 2 (SARS-CoV-2) infections and SARS-CoV-2 infections. Further disclosed are stop-gap methods for controlling the spread of coronavirus infections and the emergence of drug resistant strains of coronavirus.

18 Claims, 21 Drawing Sheets

(56) References Cited

FOREIGN PATENT DOCUMENTS

| WO | WO2016069826 | 5/2016 |
|----|--------------|--------|
| WO | WO2016069827 | 5/2016 |
| WO | WO2018089306 | 5/2018 |
| WO | WO2019018185 | 1/2019 |
| WO | WO2019079339 | 4/2019 |

OTHER PUBLICATIONS

Dyall et al., "Discovery of Inhibitors of Middle East Respiratory Syndrome Coronavirus Infection" International Conference on Antimicrobial Research, Madrid Spain, Oct. 2014 (see abstract 41, p. 55).

Hardesty et al., "The disposition of the antitumor agent, sangivamycin, in mice," Cancer Research, 34(5):005-1009 (1974).

Hinshaw et. al., "Pyrrolopyrimidine nucleosides. V. A study on the relative chemical reactivity of the 5-cyano group of the nucleoside antibiotic toyocamycin and desaminotoyocamycin. The synthesis of analogs of sangivamycin," Journal of Organic Chemistry, 35(1):236-241 (1970).

Ji et al., "SARS-CoV proteins decrease levels and activity of human ENaC via activation of distinct PKC isoforms," American Journal of Physiology. Lung Cellular and Molecular Physiology, 296(3):L372-83 (2009).

Krawczyk et al., "Synthesis and evaluation of certain thiosangivamycin analogs as potential inhibitors of cell proliferation and human cytomegalovirus," Journal of Medicinal Chemistry, 38: 4115-4119 (1995).

Kucic et al., "Inhibition of protein kinases C prevents murine cytomegalovirus replication," Journal of General Virology, 86(Pt 8):2153-2161 (2005).

Panchal et. al., "Development of high-content imaging assays for lethal viral pathogens," Journal of Biomolecular Screening, 15(7):755-765 (2010).

PubChem, "4-Amino-7-[(2R,3S,4S,5R)-3,4-dihydroxy-5-(hydroxymethyl)oxolan-2-yl]-6-hydrazinylpyrrolo[2,3-d]pyrimidine-5-carboxamide," dated Nov. 9, 2021 (13 pages).

Vittori et al., "Antiviral properties of deazaadenine nucleoside derivatives," Current Medical Chemistry, 13(29):3529-3552 (2006).

Wang et al., "Remdesivir and chloroquine effectively inhibit the recently emerged novel coronavirus (2019-nCoV) in vitrom," Cell Research, 30(3):269- 271 (2020).

* cited by examiner

METHOD FOR TREATING CORONAVIRUS INFECTIONS

CROSS-REFERENCE TO RELATED APPLICATIONS

This application is continuation of International Patent Application No. PCT/US2021/016472, filed on Feb. 3, 2021, which claims priority from U.S. Provisional Patent Application No. 62/970,087, filed Feb. 4, 2020, U.S. Provisional Patent Application No. 62/987,846, filed Mar. 10, 2020, and U.S. Provisional Patent Application No. 63/009,972, filed Apr. 14, 2020, the disclosures of each of which applications are hereby incorporated by reference herein in their entireties.

FIELD

Disclosed herein are methods, compositions and kits for treating and inhibiting Coronaviridae infections and their associated diseases.

SUMMARY OF THE DISCLOSURE

The present disclosure relates to, inter alia, methods, compositions and kits for treating Severe Acute Respiratory Syndrome coronavirus 2 (SARS-CoV-2) infections and the corresponding disease known as coronavirus disease 2019 (COVID-19), as well as for treating infections with variant strains of SARS-CoV-2.

Various aspects of the present disclosure are described in the below Paragraphs 1-48 and in the noted combinations thereof, as follows:

Paragraph 1. A method for treating Coronaviridae infection in a subject in need thereof comprising administering to a subject a therapeutically effective amount of an antiviral compound comprising:

i) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide having the formula:

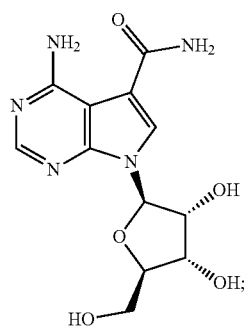

Formula IIa ii) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide hydrochloride having the formula:

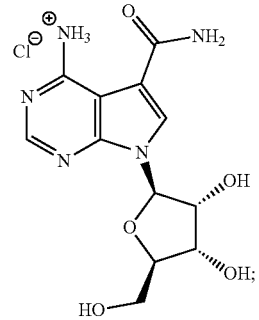

Formula Ib or iii) mixtures thereof.

Paragraph 2. The method according to Paragraph 1, wherein the Coronaviridae infection is caused by a Coronaviridae virus.

Paragraph 3. The method according to Paragraph 2, wherein the Coronaviridae virus is Severe Acute Respiratory Syndrome coronavirus 2 (SARS-CoV-2), or a variant strain of SARS-CoV-2 selected from the group consisting of B.1.1.7 from the U.K., B.1.351 from South Africa, and P.1 from Brazil, or other variant strains of SARS-CoV-2.

Paragraph 4. The method according to Paragraph 3, wherein SARS-CoV-2 is the causal agent of coronavirus disease 2019 (COVID-19).

Paragraph 5. The method according to Paragraph 2, wherein the Coronaviridae virus is selected from the group consisting of Middle East Respiratory Syndrome (MERS) coronavirus, Human coronavirus 229E (HCoV-229E), Human coronavirus OC43 (HCoV-OC43), Severe Acute Respiratory Syndrome-related coronavirus (SARS-CoV), Human coronavirus NL63 (HCoV-NL63, New Haven coronavirus), Human coronavirus HKU1, and variant strains thereof.

Paragraph 6. The method according to Paragraph 1, wherein the subject is a human or animal.

Paragraph 7. The method according to any of Paragraphs 1 to 6, wherein the effective amount is from about 0.1 mg/kg to about 10 mg/kg of the body mass of the subject or from 0.2 mg/kg to about 10 mg/kg of the body mass of the subject.

Paragraph 8. The method according to Paragraph 7, wherein the effective amount is a range selected from the group consisting of from about 0.1 mg/kg to about 1 mg/kg of the subject's body mass, from about 0.1 mg/kg to about 2 mg/kg of the subject's body mass, from about 0.2 mg/kg to about 1 mg/kg of the subject's body mass, from about 0.2 mg/kg to about 2 mg/kg of the subject's body mass, from 1 mg/kg to about 8 mg/kg of the subject's body mass, from about 2 mg/kg to about 5 mg/kg of the subject's body mass, from about 1.5 mg/kg to about 4 mg/kg of the subject's body mass, from about 4 mg/kg to about 10 mg/kg of the subject's body mass, and from about 5 mg/kg to about 8 mg/kg of the subject's body mass.

Paragraph 9. The method according to any of Paragraphs 1 to 8, wherein the antiviral compound of Formula IIa and/or Formula Ib is administered with a pharmaceutically acceptable carrier.

Paragraph 10. The method according to any of Paragraphs 1 to 9, wherein the antiviral compound of Formula IIa and/or Formula Ib is administered in combination with one or more vaccine, therapeutic, and/or other small molecule drug intended for treatment of a coronavirus as a combination therapy to treat and/or to inhibit infection with the coronavirus in the subject.

Paragraph 11. The method according to Paragraph 10, wherein the small molecule drug is selected from the group consisting of Remdesivir, Molnupiravir, Bamlanivimab, and VIR-7831.

Paragraph 12. The method according to Paragraph 11, wherein the compound of Formula IIa and/or Formula Ib is administered at a dosage ranging from about 0.1 mg/kg to about 1 mg/kg of the body mass of the subject, and wherein Remdesivir is administered at a dosage ranging from about 1 mg/kg to about 3 mg/kg of the body mass of the subject.

Paragraph 13. A method of prophylactically treating a subject uninfected with Severe Acute Respiratory Syndrome coronavirus 2 (SARS-CoV-2) or a variant strain of SARS-CoV-2 comprising administering to an uninfected subject reasonably suspected as having been exposed, of currently being exposed, or in the future of being exposed to SARS-CoV-2 or a variant strain of SARS-CoV-2, a therapeutically effective amount of an antiviral compound comprising:
  i) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide having the formula:

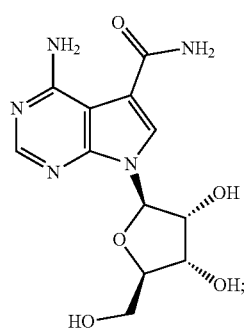

Formula IIa ii) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide hydrochloride having the formula:

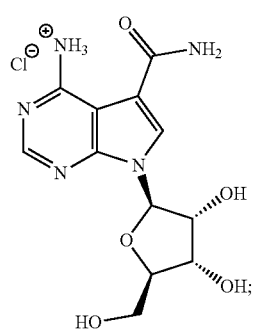

Formula Ib or
  iii) mixtures thereof.

Paragraph 14. The method according to Paragraph 13, wherein the effective amount is from about 0.1 mg/kg to about 10 mg/kg of the body mass of the subject or from 0.2 mg/kg to about 10 mg/kg of the body mass of the subject.

Paragraph 15. The method according to Paragraph 14, wherein the effective amount is a range selected from the group consisting of from about 0.1 mg/kg to about 1 mg/kg of the subject's body mass, from about 0.1 mg/kg to about 2 mg/kg of the subject's body mass, from about 0.2 mg/kg to about 1 mg/kg of the subject's body mass, from about 0.2 mg/kg to about 2 mg/kg of the subject's body mass, from 1 mg/kg to about 8 mg/kg of the subject's body mass, from about 2 mg/kg to about 5 mg/kg of the subject's body mass, from about 1.5 mg/kg to about 4 mg/kg of the subject's body mass, from about 4 mg/kg to about 10 mg/kg of the subject's body mass, and from about 5 mg/kg to about 8 mg/kg of the subject's body mass.

Paragraph 16. The method according to any of Paragraphs 13 to 15, wherein prophylactically treating a subject uninfected with SARS-CoV-2 or a variant strain of SARS-CoV-2 is used as a stop-gap method for preventing the spread of SARS-CoV-2 infection or SARS-CoV-2 variant strain infection and the related coronavirus disease 2019 (COVID-19) or variant disease.

Paragraph 17. The method according to any of Paragraphs 13 to 16, wherein the antiviral compound of Formula IIa and/or Formula Ib is administered with a pharmaceutically acceptable carrier.

Paragraph 18. The method according to any of Paragraphs 13 to 17, wherein the antiviral compound of Formula IIa and/or Formula Ib is administered in combination with one or more vaccine, therapeutic, and/or other small molecule drug intended for treatment of a coronavirus as a combination therapy to treat and/or to inhibit infection with the coronavirus in the subject.

Paragraph 19. The method according to Paragraph 18, wherein the small molecule drug is selected from the group consisting of Remdesivir, Molnupiravir, Bamlanivimab, and VIR-7831.

Paragraph 20. The method according to Paragraph 19, wherein the compound of Formula IIa and/or Formula Ib is administered at a dosage ranging from about 0.1 mg/kg to about 1 mg/kg of the body mass of the subject, and wherein Remdesivir is administered at a dosage ranging from about 1 mg/kg to about 3 mg/kg of the body mass of the subject.

Paragraph 21. A method for inhibiting the RNA-dependent RNA polymerase of the Severe Acute Respiratory Syndrome coronavirus 2 (SARS-CoV-2) or SARS-CoV-2 variant strain, comprising administering to a subject having a SARS-CoV-2 or SARS-CoV-2 variant strain infection a therapeutically effective amount of an antiviral compound comprising:
  i) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide having the formula:

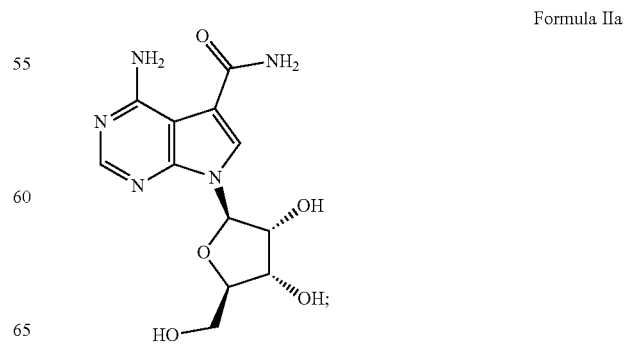

Formula IIa ii) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide hydrochloride having the formula:

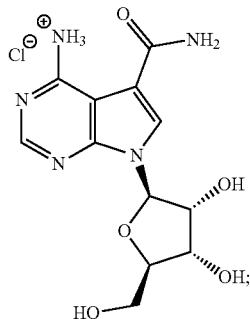

Formula Ib or iii) mixtures thereof.

Paragraph 22. The method according to Paragraph 21, wherein the effective amount is from about 0.1 mg/kg to about 10 mg/kg of the body mass of the subject or from 0.2 mg/kg to about 10 mg/kg of the body mass of the subject.

Paragraph 23. The method according to Paragraph 22, wherein the effective amount is a range selected from the group consisting of from about 0.1 mg/kg to about 1 mg/kg of the subject's body mass, from about 0.1 mg/kg to about 2 mg/kg of the subject's body mass, from about 0.2 mg/kg to about 1 mg/kg of the subject's body mass, from about 0.2 mg/kg to about 2 mg/kg of the subject's body mass, from 1 mg/kg to about 8 mg/kg of the subject's body mass, from about 2 mg/kg to about 5 mg/kg of the subject's body mass, from about 1.5 mg/kg to about 4 mg/kg of the subject's body mass, from about 4 mg/kg to about 10 mg/kg of the subject's body mass, and from about 5 mg/kg to about 8 mg/kg of the subject's body mass.

Paragraph 24. The method according to any of Paragraphs 21 to 23, wherein the antiviral compound of Formula IIa and/or Formula Ib is administered with a pharmaceutically acceptable carrier.

Paragraph 25. The method according to any of Paragraphs 21 to 24, wherein the antiviral compound of Formula IIa and/or Formula Ib is administered in combination with one or more vaccine, therapeutic, and/or other small molecule drug intended for treatment of a coronavirus as a combination therapy to treat and/or to inhibit infection with the coronavirus in the subject.

Paragraph 26. The method according to Paragraph 25, wherein the small molecule drug is selected from the group consisting of Remdesivir, Molnupiravir, Bamlanivimab, and VIR-7831.

Paragraph 27. The method according to Paragraph 26, wherein the compound of Formula IIa and/or Formula Ib is administered at a dosage ranging from about 0.1 mg/kg to about 1 mg/kg of the body mass of the subject, and wherein Remdesivir is administered at a dosage ranging from about 1 mg/kg to about 3 mg/kg of the body mass of the subject.

Paragraph 28. A pharmaceutical composition comprising:
a) a therapeutically effective amount of an antiviral compound comprising:
i) 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide having the formula:

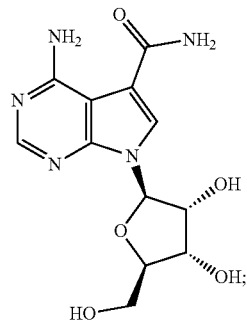

Formula IIa ii) 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide hydrochloride having the formula:

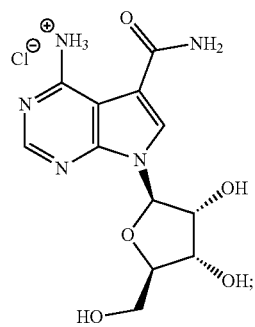

Formula Ib or iii) mixtures thereof; and
b) the balance a pharmaceutically acceptable carrier.

Paragraph 29. The composition according to Paragraph 28, comprising from about 5 mg to about 200 mg of 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide and/or the hydrochloride salt thereof.

Paragraph 30. The composition according to Paragraph 28, comprising from about 5 mg to about 25 mg of 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide and/or the hydrochloride salt thereof.

Paragraph 31. The composition according to Paragraph 28, comprising from about 10 mg to about 50 mg of 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide and/or the hydrochloride salt thereof.

Paragraph 32. The composition according to Paragraph 28, comprising from about 20 mg to about 100 mg of 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide and/or the hydrochloride salt thereof.

Paragraph 33. The composition according to Paragraph 28, comprising from about 30 mg to about 150 mg of 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide and/or the hydrochloride salt thereof.

Paragraph 34. The composition according to Paragraph 28, comprising from about 40 mg to about 200 mg of 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide and/or the hydrochloride salt thereof.

Paragraph 35. The composition according to Paragraph 28, comprising from about 5 mg to about 50 mg of 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide and/or the hydrochloride salt thereof.

Paragraph 36. The composition according to any of Paragraphs 28 to 35, wherein the composition is in the form of an oral-use composition.

Paragraph 37. The composition according to any of Paragraphs 28 to 35, wherein the composition is in the form of a pill.

Paragraph 38. The composition according to any of Paragraphs 28 to 35, wherein the composition is in the form of a capsule.

Paragraph 39. The composition according to any of Paragraphs 28 to 35, wherein the composition is in the form of a nasal delivery composition.

Paragraph 40. The composition according to any of Paragraphs 28 to 35, wherein the composition is in the form of a sterile injectable composition.

Paragraph 41. The composition according to any of Paragraphs 28 to 40, wherein the antiviral compound of Formula IIa and/or Formula Ib is administered with a pharmaceutically acceptable carrier.

Paragraph 42. The composition according to any of Paragraphs 28 to 41, wherein the antiviral compound of Formula IIa and/or Formula Ib is administered in combination with one or more vaccine, therapeutic, and/or other small molecule drug intended for treatment of a coronavirus as a combination therapy to treat and/or to inhibit infection with the coronavirus in the subject.

Paragraph 43. The composition according to Paragraph 42, wherein the small molecule drug is selected from the group consisting of Remdesivir, Molnupiravir, Bamlanivimab, and VIR-7831.

Paragraph 44. The composition according to Paragraph 43, wherein the compound of Formula IIa and/or Formula Ib is administered at a dosage ranging from about 0.1 mg/kg to about 1 mg/kg of the body mass of the subject, and wherein Remdesivir is administered at a dosage ranging from about 1 mg/kg to about 3 mg/kg of the body mass of the subject.

Paragraph 45. A kit comprising a pharmaceutical composition according to any of Paragraphs 28 to 44.

Paragraph 46. Use of a pharmaceutical composition according to any of Paragraphs 28 to 44 for the treatment of coronavirus disease 2019 (COVID-19) or COVID-19 variant disease and/or for inhibition of infection with Severe Acute Respiratory Syndrome coronavirus 2 (SARS-CoV-2) or a SARS-CoV-2 variant strain in combination with a vaccine, a therapeutic, and/or other small molecule drug intended for treatment of a coronavirus as a combination therapy to treat COVID-19 or COVID-19 variant disease and/or to inhibit infection with SARS-CoV-2 or a SARS-CoV-2 variant strain in a subject.

Paragraph 47. The use according to Paragraph 46, wherein the combination therapy is effective to inhibit and/or prevent the emergence of drug resistant strains of SARS-CoV-2.

Paragraph 48. A method for preventing the emergence of a drug-resistant strain of Severe Acute Respiratory Syndrome coronavirus 2 (SARS-CoV-2) or a SARS-CoV-2 variant strain, comprising administering to a subject having a SARS-CoV-2 infection or a SARS-CoV-2 variant strain infection a therapeutically effective amount of the pharmaceutical composition according to any of Paragraphs 28 to 44.

These and other objects, features, and advantages of this disclosure will become apparent from the following detailed description of the various aspects of the disclosure taken in conjunction with the accompanying drawings.

BRIEF DESCRIPTION OF THE FIGURES

Figures 1, 2A:
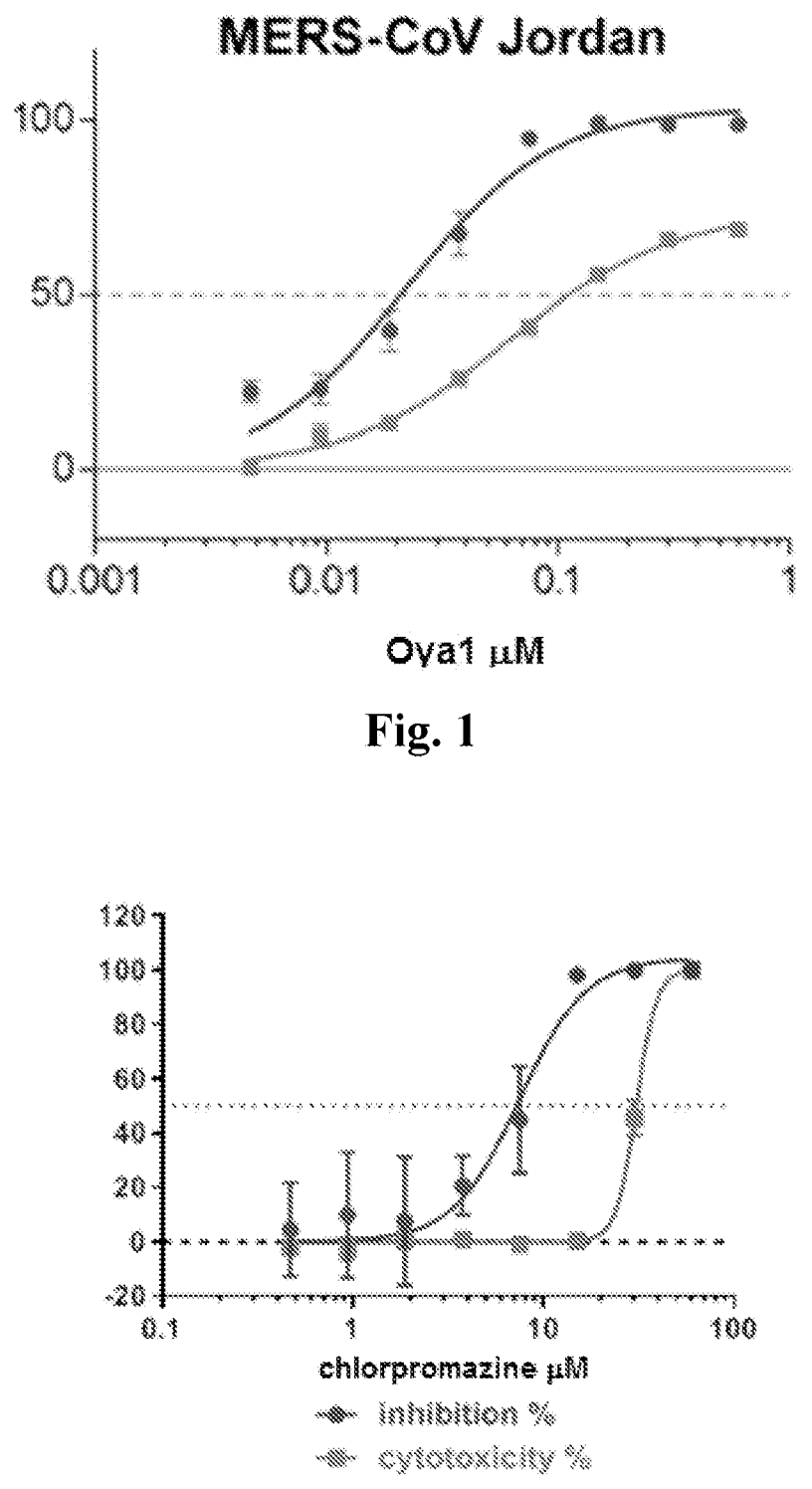

FIG. 1 depicts the antiviral activity of Oya1 against the Middle East Respiratory Syndrome (MERS) coronavirus. The top curve indicates the percentage of inhibition versus concentration and the bottom curve depicts the cytotoxicity.

FIG. 2A depicts the antiviral activity of the control compound chlorpromazine HCl on SARS-CoV2 infected Vero E6 cells at a Multiplicity of Infection 0.6 as reported in Tables 3A and 3D.

FIG. 15A: VeroE6 monkey kidney cells infected for 48 hours at a multiplicity of infection (MOI) of 0.012; FIG. 15B: Calu3 human lung cells infected for 72 hours at an MOI of 2; and FIG. 15C: Caco2 human intestinal cells infected for application in order to more fully describe the state of the art to which the disclosed matter pertains. The references disclosed are also individually and specifically incorporated by reference herein for the material contained in them that is discussed in the sentence in which the reference is relied upon.

General Definitions

Figure 2B:
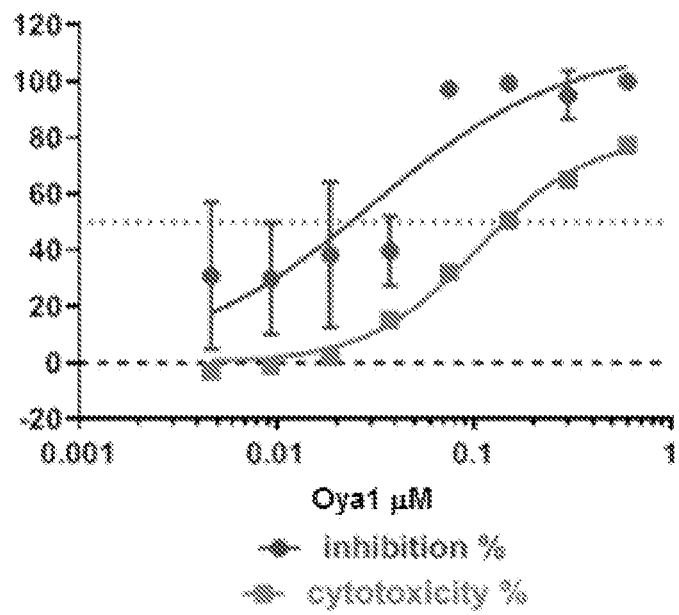
FIG. 2B depicts the antiviral activity of Oya1 on SARS-CoV2 infected Vero E6 cells at a Multiplicity of Infection 0.6 as reported in Tables 3B and 3E.

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the disclosed compounds or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

As used herein, the term "*Coronaviridae*" refers to a family of enveloped, positive-sense, single-stranded RNA viruses. The term "coronaviruses" refers to any virus in the *Coronaviridae* family, including, without limitation, Middle East Respiratory Syndrome (MERS) coronavirus, Human coronavirus 229E (HCoV-229E), Human coronavirus OC43 (HCoV-OC43), Severe Acute Respiratory Syndrome-related coronavirus (SARS-CoV), Human coronavirus NL63 (HCoV-NL63, New Haven coronavirus), Human coronavirus HKU1, novel coronavirus (2019-nCoV), also known as Severe Acute Respiratory Syndrome coronavirus 2 (SARS-CoV-2), which is the causal agent of the disease known as Wuhan pneumonia or coronavirus disease 2019 (COVID-19), and related or variant strains of any of the coronaviruses (e.g., B.1.1.7 from the U.K., B.1.351 from South Africa, and P.1 from Brazil, etc.). The term "coronavirus" also refers in the methods described herein specifically to SARS-CoV-2, which causes COVID-19, and which originated in Wuhan China in 2019. The term "SARS-CoV-2" may be used interchangeably with the term "Wuhan coronavirus" and variations thereof throughout the disclosure. The term coronavirus and variations thereof are used interchangeably throughout the disclosure. Other *Coronaviridae* viruses are used as examples, targets and standards by which the presently disclosed compounds are measured, including, without limitation, MERS (Middle East Respiratory Syndrome) coronavirus.

As used herein, the term "subject" refers to a human or an animal. The term subject can refer to a human or animal exposed to or infected with a virus of the *Coronaviridae* family. More particularly, the term subject can refer to a human or animal that has been diagnosed with COVID-19 or one or more strains of SARS-CoV-2, or has tested positive for COVID-19 or one or more strains of SARS-CoV-2. The term subject also includes humans or animals that have been exposed to Wuhan coronavirus but are not symptomatic.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

As used herein, "pharmaceutically acceptable" means physiologically tolerable, for either human or veterinary applications. In addition, "pharmaceutically acceptable" is meant for a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient, to minimize any adverse side effects in the subject, and to optimize formulation for drug delivery and dosing to the target tissues infected by *Coronaviridae* as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

"Test agents" or otherwise "test compounds" as used herein refers to an agent or compound that is to be screened in one or more of the assays described herein. Test agents include compounds of a variety of general types including, but not limited to, small organic molecules, known pharmaceuticals, polypeptides; carbohydrates such as oligosaccharides and polysaccharides; polynucleotides; lipids or phospholipids; fatty acids; steroids; or amino acid analogs. Test agents can be obtained from libraries, such as natural product libraries and combinatorial libraries. In addition, methods of automating assays are known that permit screening of several thousands of compounds in a short period.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

As used herein "stop-gap" refers to the administration of the disclosed compounds to ameliorate the spread of a coronavirus and emergence of drug resistant strains. A stop-gap administration is a temporary measure designed to control the spread of the virus until medical personnel can evaluate the extent of infection and/or the source.

Details associated with the embodiments described above and others are described below.

Methods

Disclosed herein are methods for treating a subject having a viral infection caused by a virus of the family *Coronaviridae*, particularly a coronavirus infection. Although a particular method may be described herein as an antiviral treatment or prophylactic against a specific coronavirus (e.g., the COVID-19 coronavirus), any such method is meant to also include an antiviral treatment or prophylactic against other coronaviruses in the *Coronaviridae* family.

Compounds disclosed herein for treating a coronavirus infection have Formula I:

Formula I

[Chemical structure of Formula I showing NH$_2$ group, X, R$^1$, R$^2$ substituents on a pyrrolopyrimidine nucleoside with OH, OH, and HO groups on the sugar ring]

wherein X is chosen from O or S;
R$^1$ is chosen from —NH$_2$, —NHOH and —NHNH$_2$; and
R$^2$ is chosen from hydrogen and —NHNH$_2$; or
a pharmaceutically acceptable salt thereof.

As used herein, a compound can include, without limitation, derivatives, homologs, analogs, metabolites, prodrugs, conjugates, complexes, salts, free acids, bases, solvates, enantiomers, isomers, hydrates, esters, racemates, and/or polymorphs of the compounds described herein (including, without limitation, the compounds identified herein as "Oya1" and "Oya2"), and/or any formulations thereof. In certain embodiments, the term derivatives can refer to any composition that is derived from the scaffold of the compound using chemical reactions on the compound or using de nova whole molecule chemical synthesis.

The disclosed compounds can be used to treat, cure, abate, minimize, control, and/or lessen the effects of a virus of the family *Coronaviridae* in humans and animals and spread through communities within and distal to the outbreak zone. The disclosed compounds can also be used to slow the rate of coronavirus spread in a population. The disclosed compounds can also be used to prevent or reduce the emergence of drug-resistant strains of coronaviruses by preventing coronavirus spread in a population. The disclosed compounds when administered to a subject in need of treatment can be used to stop the spread of a coronavirus virus infection. As such, the compounds disclosed herein can be administered as part of a combination therapy with one or more drugs or other pharmaceutical agents, including, without limitation, other *Coronaviridae* antiviral drugs (e.g., Remdesivir, Molnupiravir, Bamlanivimab, and VIR-7831).

As used herein, Remdesivir is meant to include all variants, derivatives, and formulations of Remdesivir, and all dosages and routes of administration. A suitable formulation of Remdesivir includes, without limitation, VEKLURY® (Gilead Sciences, Inc.). More particularly, and without meaning to be limiting, VEKLURY® can be formulated for administration by injection, and available as a sterile, preservative-free white to off-white to yellow lyophilized powder in a single-dose vial for reconstitution (100 mg/vial) (100 mg/20 ml or 5 mg/ml). Remdesivir and its formulations, dosages, routes of administration, and uses are described in the corresponding labels for VEKLURY®, as well as in U.S. Pat. Nos. 8,008,264, 8,318,682, 9,724,360, 9,949,994, 10,065,958, 10,675,296, 10,695,361, or RE46, 762 (the disclosures of which are hereby incorporated by reference herein).

Non-limiting examples of coronaviruses include Middle East Respiratory Syndrome (MERS) coronavirus, Human coronavirus 229E (HCoV-229E), Human coronavirus OC43 (HCoV-OC43), Severe Acute Respiratory Syndrome-related coronavirus (SARS-CoV), Human coronavirus NL63 (HCoV-NL63, New Haven coronavirus), Human coronavirus HKU1, novel coronavirus (2019-nCoV), also known as Severe Acute Respiratory Syndrome coronavirus 2 (SARS-CoV-2), which is the causal agent of the disease known as Wuhan pneumonia or coronavirus disease 2019 (COVID-19), and related strains of any of the coronaviruses. Examples of variant strains of SARS-CoV-2 can include, without limitation, B.1.1.7 from the U.K., B.1.351 from South Africa, and P.1 from Brazil, or other variant strains of SARS-CoV-2. As indicated in Formula I all enantiomers and diasteriomers of Formula I are included as compounds suitable for use in the herein disclosed methods for treating a subject infected with a virus of the family Coronaviridae.

Further disclosed herein is the use of the disclosed compounds for making a medicament useful in treating a subject infected with one or more viruses of the family *Coronaviridae*. The medicament can comprise one or more of the compounds having Formula I.

One aspect of the disclosure relates to methods for treating a subject having a *Coronaviridae* virus infection, comprising contacting the subject with a therapeutically effective amount of one or more compounds of Formula II:

Formula II

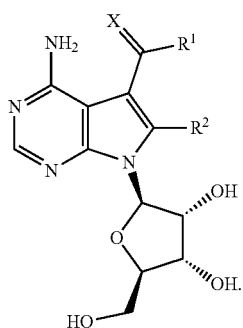

wherein X, R¹ and R² are the same as disclosed herein above; or
a pharmaceutically acceptable salt thereof.

One embodiment of this aspect comprises, contacting a subject having a COVID-19 virus infection with a therapeutically effective amount of 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide (also known as sangivamycin CAS No. 18417-89-6) and designated herein as "Oya1" having Formula IIa:

Formula IIa

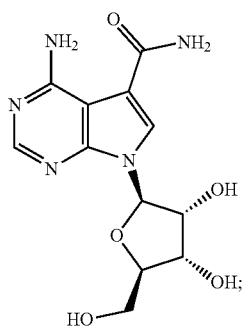 [SMILES: NC(=O)c1cn([C@@H]2O[C@H](CO)[C@@H](O)[C@H]2O)c2ncnc(N)c12]

This compound is available from Sigma-Aldrich™.

A further embodiment of this aspect comprises, contacting a subject having a COVID-19 virus infection with a therapeutically effective amount of 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide hydrochloride ("Oya1 hydrochloride," also known as sangivamycin hydrochloride CAS No. 21090-35-7) and designated herein as "Oya2" having Formula Ib:

Formula Ib

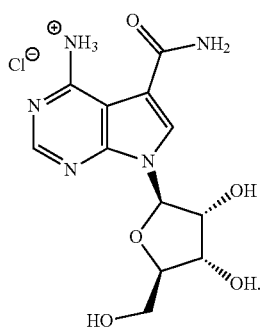

A still further example of this embodiment comprises, contacting a subject having an COVID-19 virus infection with a therapeutically effective amount of 4-amino-7-((2R,3R,4S,5R)-3,4-dihydroxy-5-(hydroxymethyl)tetrahydrofuran-2-yl)-6-hydrazinyl-N-hydroxy-7H-pyrrolo[2,3-d]pyrimidine-5-carboximidamide having Formula III:

Formula III

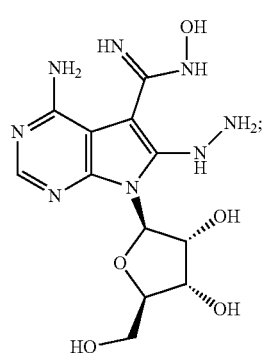

or a pharmaceutically acceptable salt thereof. This compound is referred to as 'Oya1-Like Molecule 5 (SLM5) and is available from the NIH Developmental Therapeutics Program (DTP).

A still further embodiment comprises, contacting a subject having an COVID-19 virus infection with a therapeutically effective amount of 4-amino-7-((2R,3R,4S,5R)-3,4-dihydroxy-5-(hydroxymethyl)tetrahydrofuran-2-yl)-6-hydrazinyl-7H-pyrrolo[2,3-d]pyrimidine-5-carboximidhydrazide having Formula IV:

Formula IV

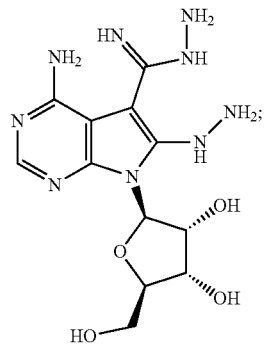

or a pharmaceutically acceptable salt thereof. This compound is referred to as 'Oya1-Like Molecule 6 (SLM6) and is available from the NIH Developmental Therapeutics Program (DTP).

A another further embodiment comprises, contacting a subject having an COVID-19 virus infection with a therapeutically effective amount of 4-amino-7-((2R,3R,4S,5R)-3,4-dihydroxy-5-(hydroxymethyl)tetrahydrofuran-2-yl)-6-hydrazinyl-7H-pyrrolo[2,3-d]pyrimidine-5-carboximidamide having Formula V:

Formula V or a pharmaceutically acceptable salt thereof. This compound is referred to as 'Oya1-Like Molecule 7 (SLM7) and is available from the NIH Developmental Therapeutics Program (DTP).

A yet further embodiment comprises, contacting a subject having an COVID-19 virus infection with a therapeutically effective amount of 4-amino-7-((2R,3R,4S,5R)-3,4-dihydroxy-5-(hydroxymethyl)tetrahydrofuran-2-yl)-7H-pyrrolo[2,3-d]pyrimidine-5-carbothioamide (thioOya1) having Formula VI:

Formula VI or a pharmaceutically acceptable salt thereof.

Combination Therapy

One aspect of the disclosure relates to the use of a pharmaceutical composition as disclosed herein for the treatment of COVID-19 or variants thereof and/or for inhibition of infection with SARS-CoV-2 or variant strains thereof in combination with a vaccine, a therapeutic, and/or other small molecule drug intended for treatment of Coronavirus as a combination therapy to treat COVID-19 or variants thereof and/or to inhibit infection with SARS-CoV-2 or variant strains thereof in a subject. One embodiment of this aspect involves using the combination therapy in a manner and under conditions effective to inhibit and/or prevent the emergence of drug resistant strains of SARS-CoV-2 or its variants. Suitable small molecule drugs for use in combination with a compound of the present disclosure (e.g., Formula IIa and/or Formula Ib) can include, without limitation, any *Coronaviridae* antiviral small molecule compound (e.g., Remdesivir, Molnupiravir, Bamlanivimab, and VIR-7831).

In one embodiment, the combination therapy involves one or more *Coronaviridae* antiviral small molecule compound in addition to a compound of the present disclosure (e.g., Formula IIa and/or Formula Ib), where the combination results in a synergistic effect of the combined compounds. As used herein, but without limitation, in certain embodiments, the synergistic effect is such that one or more of the compounds in the combination can be used in a lower dosage and/or for a shorter time than needed when used without the combination. In certain embodiments, the combination of dosing a compound of the present disclosure (e.g., Formula IIa and/or Formula Ib) simultaneously with Remdesivir dosing in the treatment of a SARS-CoV-2 infection can have an additive effect in reducing viral replication. Additive effects of such combined treatments can reduce the IC50 of each compound commensurate with the dose and ratio.

In one embodiment, the combination therapy involves administering to a subject in need of treatment for Coronavirdae infection a compound of Formula IIa and/or Formula Ib in combination with Remdesivir. In certain embodiments, the combination therapy involves, without limitation, the administration to the subject in need thereof a compound of Formula IIa and/or Formula Ib at a dosage ranging from about 0.1 mg/kg to about 1 mg/kg of the body mass of the subject, and Remdesivir at a dosage ranging from about 1 mg/kg to about 3 mg/kg of the body mass of the subject for 5 to 10 days.

RNA-Dependent RNA Polymerase Inhibition

MERS-CoV Jordan virus, obtained from a subject infected with this virus in Jordan, was treated in vitro with a series of 2-fold dilutions of Oya1 as depicted in FIG. 1 to provide an 8-point dose curve. Oya1 was found to have approximately 100% inhibition of the MERS-CoV RNA polymerase at a concentration of 0.1 μM (see, top curve (●)) whereas the lower curve (■) indicates the percent cytotoxicity. The $IC_{50}$ value is indicated by the dotted line. Without wishing to be limited by theory, the RNA-dependent RNA polymerases of coronaviruses are highly conserved. Indeed, MERS-CoV and COVID-19 coronavirus have 98% homology. Because of this coronavirus homology, the results depicted in FIG. 1 indicate that administering Oya1 to a subject infected with SARS-CoV-2 or having COVID-19, provides a means and/or method for treating a subject diagnosed with COVID-19 or a SARS-CoV-2 infection.

Disclosed herein is a method for treating a subject with a COVID-19 coronavirus infection, comprising contacting a subject infected with the COVID-19 coronavirus with an effective amount of Oya1 or Oya2. The Oya1 or Oya2 can be delivered as an aqueous-based composition. The compositions can be delivered intramuscularly, intravenously, orally, or inhaled. The amount of Oya1 or Oya2 delivered to a subject in a single treatment (also referred to herein as a "bolus") can be determined by the person providing the treatment. In general, amounts up to 3 mg/kg can be delivered in a single treatment whether IM or IV as described herein.

One aspect disclosed herein are methods for treating a subject infected with the COVID-19 coronavirus, comprising: administering to a subject a therapeutically effective amount of 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide having the formula:

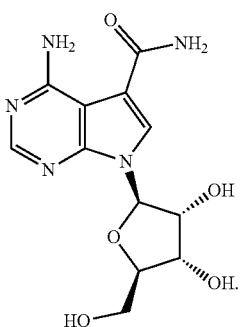 [SMILES: NC(=O)c1cn([C@@H]2O[C@H](CO)[C@@H](O)[C@H]2O)c2ncnc(N)c12]

Further disclosed herein are methods for treating a subject infected with the COVID-19 coronavirus, comprising: administering to a subject a therapeutically effective amount of 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide hydrochloride having the formula:

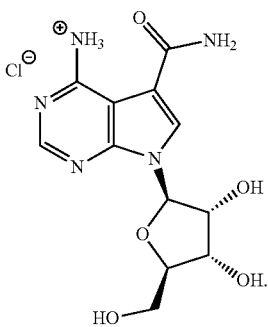 [SMILES: [Cl-] ; NC(=O)c1cn([C@@H]2O[C@H](CO)[C@@H](O)[C@H]2O)c2ncnc([NH3+])c12]

Still further disclosed is a method for inhibiting the RNA-dependent RNA polymerase of the COVID-19 coronavirus, comprising administering to a subject having a COVID-19 coronavirus infection a therapeutically effective amount of:

i) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide having the formula:

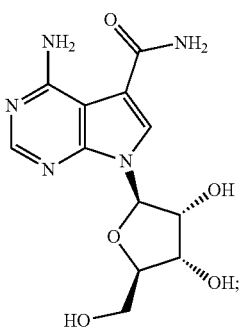 [SMILES: NC(=O)c1cn([C@@H]2O[C@H](CO)[C@@H](O)[C@H]2O)c2ncnc(N)c12]

ii) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide hydrochloride having the formula:

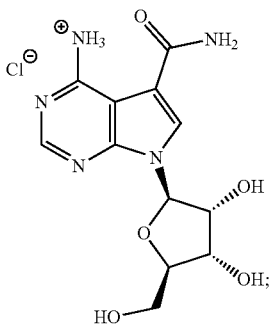 [SMILES: [Cl-] ; NC(=O)c1cn([C@@H]2O[C@H](CO)[C@@H](O)[C@H]2O)c2ncnc([NH3+])c12]

or iii) mixtures thereof.

The disclosed methods provide a single dose of Oya1 or Oya2 based upon the body mass of the subject being treated. Therefore, a single dose of Oya1 or Oya2 can range from about 0.1 mg/kg to about 10 mg/kg of the subject's body mass.

In one embodiment, the effective amount of the antiviral compound of the present disclosure (e.g., Formula IIa or Ib) is from about 0.1 mg/kg to about 10 mg/kg of the body mass of the subject or from 0.2 mg/kg to about 10 mg/kg of the body mass of the subject.

In one embodiment, the effective amount of the antiviral compound of the present disclosure (e.g., Formula IIa or Ib) can include, without limitation, from about 0.1 mg/kg to about 1 mg/kg of the subject's body mass, from about 0.1 mg/kg to about 2 mg/kg of the subject's body mass, from about 0.2 mg/kg to about 1 mg/kg of the subject's body mass, from about 0.2 mg/kg to about 2 mg/kg of the subject's body mass, from 1 mg/kg to about 8 mg/kg of the subject's body mass, from about 2 mg/kg to about 5 mg/kg of the subject's body mass, from about 1.5 mg/kg to about 4 mg/kg of the subject's body mass, from about 4 mg/kg to about 10 mg/kg of the subject's body mass, and from about 5 mg/kg to about 8 mg/kg of the subject's body mass.

In one embodiment, the amount of Oya1 or Oya2 in a single dose is from about 1 mg/kg to about 8 mg/kg of the subject's body mass.

In another embodiment, the amount of Oya1 or Oya2 in a single dose is from about 2 mg/kg to about 5 mg/kg of the subject's body mass.

In a further embodiment, the amount of Oya1 or Oya2 in a single dose is from about 1.5 mg/kg to about 4 mg/kg of the subject's body mass.

In a yet further embodiment, the amount of Oya1 or Oya2 in a single dose is from about 4 mg/kg to about 10 mg/kg of the subject's body mass.

In a still further embodiment, the amount of Oya1 or Oya2 in a single dose is from about 5 mg/kg to about 8 mg/kg of the subject's body mass.

For example, the dose can comprise any amount of Oya1 or Oya2 from about 0.1 mg/kg to about 10 mg/kg of the body mass of the subject being treated.

For example, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, or 50 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 90 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or 10.0 mg/kg of body mass.

Further disclosed is a "stop-gap" method for controlling the spread of the COVID-19 coronavirus (or other coronavirus) outbreak and the spread within an affected population and from people travelling from the outbreak zone or travelling into and around or nearby the outbreak zone as in the recent example of the COVID-19 outbreak. What is meant herein by "stop-gap" is a method for temporarily halting the transmission of a coronavirus (including, for example, the COVID-19 coronavirus) among a population group until such time when viral strain-specific therapies become available whether those are small molecule, vaccine, or other antiviral therapeutics. It has been determined that transmission of the virus can occur by close contact with an infected subject, wherein transmission is due in part to contact with a cough aspirant or other bodily fluid. Without wishing to be limited by theory, Oya1 or Oya2 is effective for eight days following a single maximum tolerated dose or with repeated daily submaximal doses in inhibiting the activity of coronavirus polymerase. Therefore, removing a subject from an area wherein infection has been found, but wherein the subject is otherwise asymptomatic, provides a means to protect the subject from infection, and protecting healthcare or other professional who must come in contact with the patient from disease transmission. Treatment of patients with or without symptoms, at large or in quarantine with Oya1 or Oya2, will reduced the replication of the virus and thereby mitigate the severity of and development of disease symptom, reduce the transmission the virus as a control measure and save lives for those who may be immunocompromised and at risk for sever complications and death. Thus, in one sense, a stop-gap in accordance with the present disclosure is a therapeutic treatment used to slow the progression of a disease within an infected patient or to reduce the spread of a viral infection to uninfected people within an outbreak zone as a temporary means of controlling morbidity and mortality.

Therefore, disclosed herein is a method of preventing the transmission and spread of COVID-19, comprising removing a subject from a site of infection risk and administering an effective amount of Oya1 or Oya2 to the subject. The subject once treated, can be isolated for the purposes of observation. After 8 days, an additional bolus of Oya1 or Oya2 can be further administered if warranted.

Further disclosed herein is a method of prophylactically treating a subject uninfected with SARS-CoV-2, but reasonably suspected as having been exposed, of currently being exposed, or in the future of being exposed to SARS-CoV-2, by administering a therapeutically effective amount of Oya1 or Oya2 to the uninfected subject. This method is intended to prevent and/or reduce new infections of SARS-CoV-2.

Further disclosed herein is a method of treating people prophylactically who have not been infected but need protection from infection when entering outbreak zones, treating infected individuals, decontaminating infected areas, or participating in maintaining civil rule of law by administering an effective amount of Oya1 or Oya2 to uninfected subjects a bolus of Oya1 or Oya2 prior to and during contact with infected people or surfaces.

Disclosed herein is the use of Oya1 and/or Oya2 to treat a COVID-19 coronavirus infection. Further disclosed is the use of Oya1 and Oya2 to treat one or more of the virus infections chosen from Middle East Respiratory Syndrome (MERS) coronavirus, Human coronavirus 229E (HCoV-229E), Human coronavirus OC43 (HCoV-OC43), Severe Acute Respiratory Syndrome-related coronavirus (SARS-CoV), Human coronavirus NL63 (HCoV-NL63, New Haven coronavirus), Human coronavirus HKU1, and a novel coronavirus (2019-nCoV), also known as SARS-CoV-2, which is the causal agent of the disease known as Wuhan pneumonia or COVID-19, or variant strains thereof.

Compositions

Disclosed herein are pharmaceutical compositions for use in treating a subject infected with a coronavirus, including, without limitation, the COVID-19 coronavirus, the pharmaceutical compositions comprising:
  a) a therapeutically effective amount of:
    i) 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide having the formula:

ii) 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide hydrochloride having the formula:

or iii) mixtures thereof; and b) the balance a pharmaceutically acceptable ingredients.

In one embodiment the therapeutically effective amount is from about 1 mg/kg to about 3 mg/kg of the body mass of the subject to be treated.

The disclosed compositions can comprise from about 5 mg to about 200 mg. In one aspect the disclosed single dose compositions of Oya1 or Oya2 can comprise any amount from about 5 mg to about 200 mg. For example, the disclosed compositions can comprise 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 120 mg, 121 mg, 122 mg, 123 mg, 124 mg, 125 mg, 126 mg, 127 mg, 128 mg, 129 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 190 mg, 191 mg, 192 mg, 193 mg, 194 mg, 195 mg, 196 mg, 197 mg, 198 mg, 199 mg, or 200 mg of Oya1 and/or Oya2. In certain embodiments, the disclosed compositions can comprise 201 mg, 202, mg, 203, mg, 204 mg, 205 mg, 206 mg, 207 mg, 208 mg, 209 mg, 210 mg, 212 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg of Oya1 and/or Oya2.

In general, the disclosed pharmaceutical compositions include but are not limited to those suitable for oral, rectal, nasal, topical (including buccal and sub-lingual), transdermal, vaginal or parenteral (including intramuscular, subcutaneous and intravenous) administration or in a form suitable for administration by inhalation or insufflation. The compositions can, where appropriate, be conveniently presented in discrete dosage units and may be prepared by any of the methods well known in the art of pharmacy. Pharmaceutical compositions suitable for oral administration are conveniently presented as discrete units such as capsules, cachets or tablets, each containing a predetermined amount of the active substance.

Oral-Use Compositions

Disclosed herein are compositions for oral delivery of 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide (Oya1) and/or 4-amino-7-((2R,3R,4S,5R)-3,4-dihydroxy-5-(hydroxymethyl)tetrahydro-furan-2-yl)-7H-pyrrolo[2,3-d]pyrimidine-5-carboxamide hydrochloride (Oya2). The compositions comprise:

a) from about 25 mg to about 250 mg by weight of Oya1, Oya2 or mixtures thereof, and b) a pharmaceutically acceptable ingredients.

The disclosed oral use compositions can be in the form of a liquid composition or a solid in the form of a tablet or flowable powder. The disclosed pharmaceutically-acceptable excipients include, but are not limited to, polymers, resins, plasticizers, fillers, lubricants, solvents, co-solvents, surfactants, preservatives, sweetener agents, flavoring agents, buffer systems, pharmaceutical-grade dyes or pigments, and viscosity agents.

When present the coating can contain a plasticizer and possibly other coating excipients such as coloring agents, talc, and/or magnesium stearate, many of which are well known in the coating art. In particular, anionic carboxylic acrylic polymers usually can contain 10-25% by weight of a plasticizer, especially dibutyl phthalate, polyethylene glycol, triethyl citrate and triacetin. Conventional coating techniques such as spray or pan coating are employed to apply the coating. As previously mentioned, the coating thickness must be sufficient to ensure that the oral dosage form remains intact until the desired site of topical delivery in the lower intestinal tract is reached.

Liquid compositions comprise a suitable liquid carrier, for example, sterilized water. In addition, the liquid compositions can comprise buffers, preservatives, flavoring agents and co-solvents.

Nasal Delivery Compositions

Disclosed herein are compositions for delivery of the disclosed compounds via nasal inhalation. The compositions which are inhaled can reside in the nostril or sinus cavities or can percolate downward and flow into the lungs. Without wishing to be limited by theory it is believed there is a higher concentration of COVID-19 coronavirus in the nose and nasal passages. The compositions for nasal delivery are fine powders or nebulized solutions comprising Oya1 and/or Oya2 in an amount from about 25 mg to about 250 mg per inhaled dose.

Sterile Injectable Compositions

Administration of Sterile Injectable Composition

A disclosed sterile injectable composition can be injected using any of the known methods in the art. Particularly, a composition can be administered by means of an injection device suitable for intraepidermal and/or intradermally and/or subcutaneously.

The injection device particularly when a disclosed composition is administered by means of an injection device suitable for intraepidermal and/or intradermally and/or subcutaneously, can be selected from a syringe, a set of microsyringes, a laser device, a hydraulic device, an injection gun, a needleless injection device, or a rolling with microneedles. In one embodiment the injection device is chosen from a syringe or a set of microsyringe.

In a further embodiment, the injection device can be adapted to the technique of mesotherapy. Mesotherapy is a treatment technique by intraepidermal and/or intradermally and/or subcutaneously active(s) product(s). The administration intraepidermal and/or intradermally and/or subcutaneously according to the present disclosure is to inject a disclosed composition in an epidermal region, dermo-epidermal and/or dermal.

In addition, the injection device can comprise any conventionally used injection such as hypodermic needle or cannula. For example, a needle or a cannula according to the present disclosure can have a diameter ranging between 18 and 34 G. In one embodiment the diameter can be from about 25 to about 32 G. The length can vary from about 4 to about 70 mm. In one embodiment the diameter is from about 4 to about 25 mm. The needles used to inject the disclosed sterile compositions can be disposable. Advantageously, the needle or cannula is associated with a syringe or other device capable of delivering through the needle or cannula disclosed injectable composition.

According to one embodiment, a catheter may be inserted between the needle/cannula and syringe. In known manner, the syringe can be operated manually by the practitioner or by a syringe holder as guns.

The disclosed injectable sterile compositions comprise:
a) from about 25 mg to about 250 mg of a compound chosen from 4-amino-7-((2R,3R,4S,5R)-3,4-dihydroxy-5-(hydroxymethyl)-tetrahydrofuran-2-yl)-7H-pyrrolo[2,3-d]pyrimidine-5-carboxamide and/or the hydrochloride salt thereof (Oya1 and/or Oya2); and
b) a pharmaceutically acceptable carrier.

In one embodiment the pharmaceutically acceptable carrier is deionized, sterile water.

The injectable compositions can further comprise one or more isotonic agents suitable for the preparation of a disclosed composition, for example a sugar and/or sodium chloride. The acceptable carrier can be a balanced salt solution, for example, phosphate buffered saline.

In addition, the composition can further comprise an antioxidant, for example, glutathione, ellagic acid, spermine, resveratrol, retinol, L-carnitine, polyols, polyphenols, flavonols, theaflavins, catechins, caffeine, ubiquinol, ubiquinone, and mixture thereof.

In a further embodiment the disclosed composition can further comprise any excipient commonly used in the technical field, for example, mono- and/or di-hydrated dihydrogenophosphate sodium and sodium chloride, in physiological concentrations. The amounts of additional active agents and/or excipients of course depend on the nature of the desired properties determined by the formulator, the desired effect, and the destination of the composition according to the invention.

The disclosed composition, once prepared, can be sterilized by heat and directly packaged in suitable containers known in the art.

Capsules

Disclosed herein is a pharmaceutical preparation comprising a capsule containing from about 25 mg to about 250 mg of 4-amino-7-((2R,3R,4S,5R)-3,4-dihydroxy-5-(hydroxymethyl)-tetrahydrofuran-2-yl)-7H-pyrrolo[2,3-d]pyrimidine-5-carboxamide and/or the hydrochloride salt thereof (Oya1 and/or Oya2).

The compositions in the form of a capsule comprise:
a) from about 25 mg to about 250 mg of a compound chosen from 4-amino-7-((2R,3R,4S,5R)-3,4-dihydroxy-5-(hydroxymethyl)-tetrahydrofuran-2-yl)-7H-pyrrolo[2,3-d]pyrimidine-5-carboxamide and/or the hydrochloride salt thereof (Oya1 and/or Oya2); and
b) a pharmaceutically acceptable carrier.

Another embodiment of the disclosed compositions are compositions in the form of a tablet. The tablets can comprise the same amount of Oya1 and/or Oya2 as the capsules. A further embodiment of the disclosed compositions are compositions in the form of a sterile injectable formulation. The injectable formulations can comprise the same amount of Oya1 and/or Oya2 as the capsules.

The disclosed compositions can comprise one or more pharmaceutically acceptable excipients, carriers or binders.

Antiviral Control and Efficacy Testing

Dyall et al. screened a library of 290 compounds to identify drugs that inhibit MERS-CoV or the related human pathogen severe acute respiratory syndrome coronavirus (SARS-CoV). (See, Dyall et al., "Discovery of Inhibitors of Middle East Respiratory Syndrome Coronavirus Infection" International Conference on Antimicrobial Research, Madrid Spain, October 2014.)

Of the drugs that were screened, 27 were selected for further testing to determine if their inhibition of MERS and SARS were greater than 50% and the cytotoxicity was less than 30%. Chlorpromazine HCl was found to have a MERS $IC_{50}$ of 9.5 μM and a SARS $IC_{50}$ of 13.0 μM. Chlorpromazine HCl was further paired with the other selected drugs to determine if there was a synergy against MERS CoV. Based upon the measured synergy of chlorpromazine HCl with the following: emetine dihydrocloride hydrate, E-64-D and amodiaquine dihydrochloride dehydrate, chlorpromazine HCl was selected as the reference SARS-CoV inhibitor for testing of Oya1 and Oya2.

SARS-CoV-2019 Assay MOI 0.6 and 1.3

Oya1 and Oya2 activity was tested in a drug screen assay against nCoV-2019 at MOI 0.6 and 1.3 in Vero E6 cells. Chlorpromazine HCl was used as the positive control. The cells were fixed at 48 hours. ELISA stains were performed with the SARS-CoV nucleoprotein/NP antibody, Rabbit Mab antibody and IFA assay.

Stock solutions of 100 mM chlorpromazine, 20 mM Oya1 and 20 mM Oya2 in DMSO. The following 96 Well plates were prepared in preparation for duplicate experiments:

TABLE 1

| Plate type | Cell type | Cell Seeding | Notes |
|---|---|---|---|
| 96 Well Operetta x2 | Vero E6 | 30,000 cells/well | Plate all wells |
| 96 Well Black Opaque | Vero E6 | 30,000 cells/well | No cells in $12^{th}$ col. |
| 96 Well Operetta x2 | Vero E6 | 30,000 cells/well | Plate all wells |
| 96 Well Black Opaque | Vero E6 | 30,000 cells/well | No cells in $12^{th}$ col. |

The plates were prepared in DMEM w/10% FBS. As indicated below the following serial dilutions were used in triplicate of each MOI.

TABLE 2

| Chlorpromazine (μM) | | | Oya1 (μM) | | | Oya2 (μM) | | |
|---|---|---|---|---|---|---|---|---|
| 60.00 | 60.00 | 60.00 | 0.60 | 0.60 | 0.60 | 0.60 | 0.60 | 0.60 |
| 30.00 | 30.00 | 30.00 | 0.30 | 0.30 | 0.30 | 0.30 | 0.30 | 0.30 |
| 15.00 | 15.00 | 15.00 | 0.15 | 0.15 | 0.15 | 0.15 | 0.15 | 0.15 |
| 7.50 | 7.50 | 7.50 | 0.08 | 0.08 | 0.08 | 0.08 | 0.08 | 0.08 |
| 3.75 | 3.75 | 3.75 | 0.04 | 0.04 | 0.04 | 0.04 | 0.04 | 0.04 |
| 1.88 | 1.88 | 1.88 | 0.02 | 0.02 | 0.02 | 0.02 | 0.02 | 0.02 |
| 0.94 | 0.94 | 0.94 | 0.01 | 0.01 | 0.01 | 0.01 | 0.01 | 0.01 |
| 0.47 | 0.47 | 0.47 | 0.005 | 0.005 | 0.005 | 0.005 | 0.005 | 0.005 |

As seen in Table 2 all experiments were run in triplicate. 4 plates were run for efficacy (2× Vero E6, 2× Vero E6) and 2 plates for toxicity (1× Vero E6, 1× Vero E6).

50 µL of the compound solution to be tested dissolved in DMEM/10% FBS (Table 2) is pipetted to the corresponding wells of the efficacy and cytotoxicity plates. Prior to adding the test solution to the cell plates, Rainin liquidator-96 was used to mix all wells of the compound plate, by pipetting up and down 3 times with a maximum volume of 200 µL. All tips used in this step were discarded and fresh tips were used for the subsequent step.

50 µL of DMEM/10% FBS is added to the wells of the cytotoxicity plates to compensate for these plates not receiving any virus. 50 µL of DMEM/10% FBS is added to the 12$^{th}$ column of all the efficacy plates to compensate for these wells not receiving virus later in the assay.

Vero E6 cells were plated at 30,000/well in black opaque or clear bottom 96-well Operetta plates one day prior assay. Chlorpromazine HCl, Oya1 and Oya2 were tested in an 8-point dose response curve using the serial dilutions of Table 2. Each dose was run in triplicate.

48 hours after compound was added to virus containing wells supernatant was removed and 20% formalin was added to the wells to fix the cells onto the plate. Formalin was removed and plates were washed 3 times with PBS. Blocking was performed with 3% BSA in PBS for 30 minutes at room temperature. Primary antibody (SARS-CoV nucleoprotein/NP antibody) at a dilution of 1:8000 was added to the wells and incubated on an orbital shaker for 60 minutes at 37° C. After a 3× wash in PBS Goat anti-Rabbit IgG (H+L) Highly Cross-Adsorbed Secondary Antibody, Alexa Fluor 594 was added to the wells at a dilution of 1:2500 and incubated on the shaker for 30 minutes at room temperature. After a 6× wash with PBS Hoechst 33342, Trihydrochloride, Trihydrate—10 mg/mL Solution in Water at a dilution of 1:2500 was added to wells and incubated for 10 minutes in the dark. After a 6× wash in PBS fluorescence imaging was recorded on the Perkin Elmer Operetta in the Alexafor 594 and DAPI channels.

Cytotoxicity plates were measured with CellTiter-Glo (Promega) by adding 100 microliters to the cells not infected with virus 48 hours after compound addition. Plates were shaken for 2 minutes at room temperature and incubated for 10 minutes before luminescence was read on an M1000 Tecan plate reader for 1000 ms.

MOI 0.6 Plate 1

Figure 2C:
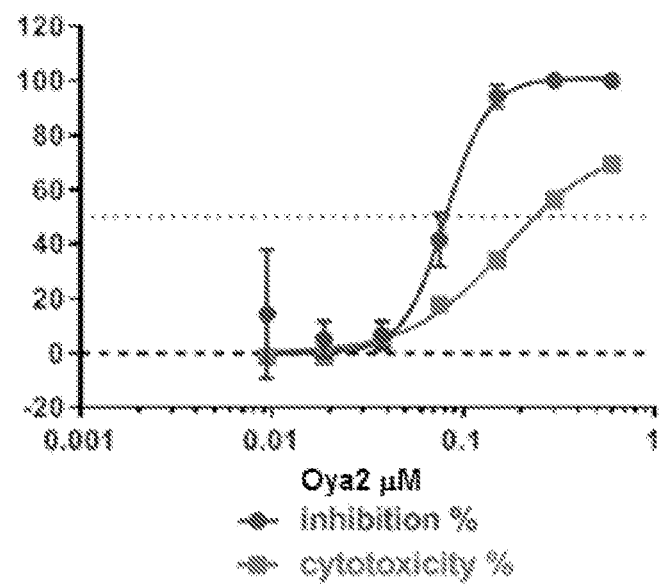
FIG. 2C depicts the antiviral activity of Oya2 on SARS-CoV2 infected Vero E6 cells at a Multiplicity of Infection 0.6 as reported in Tables 3C and 3F. The percent inhibition that the test compounds displayed is indicated by (●), whereas the percent toxicity is indicated by (■).

Tables 3A-3F below disclose the results of the SARS-CoV2-E6 assay with a multiplicity of infection (MOI) of 0.6 on Plate 1. All tests were run in triplicate. The inhibition results are shown in Tables 3A-3C whereas the cytotoxicity tests are shown in Tables 3D-3F. These data can be seen graphically in FIGS. 2A-2C.

TABLE 3A

Inhibition Chlorpromazine HCl MOI 0.6

| Concentration (µM) | Test 1 | Test 2 | Test 3 |
|---|---|---|---|
| 0.4688 | 22.1979493 | −12.9257 | 3.04648982 |
| 0.9375 | 7.60705942 | 33.95865 | −12.07231264 |
| 1.875 | 30.6738632 | 8.61889 | −16.61821703 |
| 3.75 | 31.6123727 | 10.15863 | 20.10096712 |
| 7.5 | 26.2012789 | 65.4867 | 43.12377828 |
| 15 | 99.2887326 | 99.59316 | 95.96772876 |
| 30 | 100.079574 | 100.0796 | 99.61691765 |
| 60 | 100.079574 | 100.0796 | 100.0795735 |

TABLE 3B

Inhibition Oya1 MOI 0.6

| Concentration (µM) | Test 1 | Test 2 | Test 3 |
|---|---|---|---|
| 0.0047 | 44.48755 | 0.802866 | 47.71368 |
| 0.0094 | 38.12328 | 44.50221 | 7.372432 |
| 0.0188 | 50.7345 | 55.95496 | 8.912174 |
| 0.0375 | 27.4624 | 39.73635 | 52.31824 |
| 0.075 | 95.45448 | 98.65583 | 98.30227 |
| 0.15 | 98.64189 | 99.77602 | 99.74479 |
| 0.3 | 100.0796 | 100.0796 | 85.35671 |
| 0.6 | 100.0796 | 100.0796 | 100.0796 |

TABLE 3C

Inhibition Oya2 MOI 0.6

| Concentration (µM) | Test 1 | Test 2 | Test 3 |
|---|---|---|---|
| 0.0047 | 15.08581 | −2.3646 | −10.9725 |
| 0.0094 | 3.354438 | 41.45206 | −1.64606 |
| 0.0188 | −2.21796 | 8.413591 | 9.660049 |
| 0.0375 | 12.21262 | 2.812862 | 5.216793 |
| 0.075 | 45.61669 | 48.79883 | 30.54189 |

TABLE 3C-continued

Inhibition Oya2 MOI 0.6

| Concentration (μM) | Test 1 | Test 2 | Test 3 |
|---|---|---|---|
| 0.15 | 90.10498 | 94.80632 | 98.18496 |
| 0.3 | 100.0796 | 100.0796 | 99.8055 |
| 0.6 | 100.0796 | 100.0796 | 99.75872 |

TABLE 3D

Cytotoxicity Chlorpromazine HCl MOI 0.6

| Concentration (μM) | Test 1 | Test 2 | Test 3 |
|---|---|---|---|
| 0.4688 | −1.92226 | −2.47389 | −1.85479 |
| 0.9375 | −7.06067 | 0.412456 | −1.53258 |
| 1.875 | −0.89998 | 4.449293 | −1.16314 |
| 3.75 | 0.005904 | 0.469812 | 1.571381 |
| 7.5 | −1.09398 | −3.32579 | 1.193507 |
| 15 | 1.600059 | 0.673931 | −1.39763 |
| 30 | 38.61481 | 46.71716 | 51.33768 |
| 60 | 99.94589 | 99.93324 | 99.97643 |

TABLE 3E

Cytotoxicity Oya1 MOI 0.6

| Concentration (μM) | Test 1 | Test 2 | Test 3 |
|---|---|---|---|
| 0.0047 | −3.31399 | −2.16687 | −3.38484 |
| 0.0094 | −0.23533 | −1.9307 | −0.58125 |
| 0.0188 | −0.57609 | 5.048156 | 2.473892 |
| 0.0375 | 14.23183 | 14.78684 | 16.69476 |
| 0.075 | 29.55765 | 33.63666 | 33.59955 |
| 0.15 | 49.52422 | 51.35623 | 51.37142 |
| 0.3 | 66.56565 | 64.56494 | 64.1314 |
| 0.6 | 79.77773 | 76.75643 | 75.87753 |

TABLE 3F

Cytotoxicity Oya2 MOI 0.6

| Concentration (μM) | Test 1 | Test 2 | Test 3 |
|---|---|---|---|
| 0.0047 | −2.539682 | −1.465104 | −2.75055 |
| 0.0094 | 0.449568419 | −3.730659 | −1.04674 |
| 0.0188 | −1.94588057 | −1.045057 | −1.4651 |
| 0.0375 | 0.621635881 | 5.5913491 | 5.689191 |
| 0.075 | 16.0756557 | 19.631717 | 18.12866 |
| 0.15 | 35.3674547 | 35.252743 | 31.56173 |
| 0.3 | 55.54489506 | 56.531753 | 57.44101 |
| 0.6 | 69.73539989 | 68.706369 | 69.50935 |

MOI 0.6 Plate 2

Figure 3A:
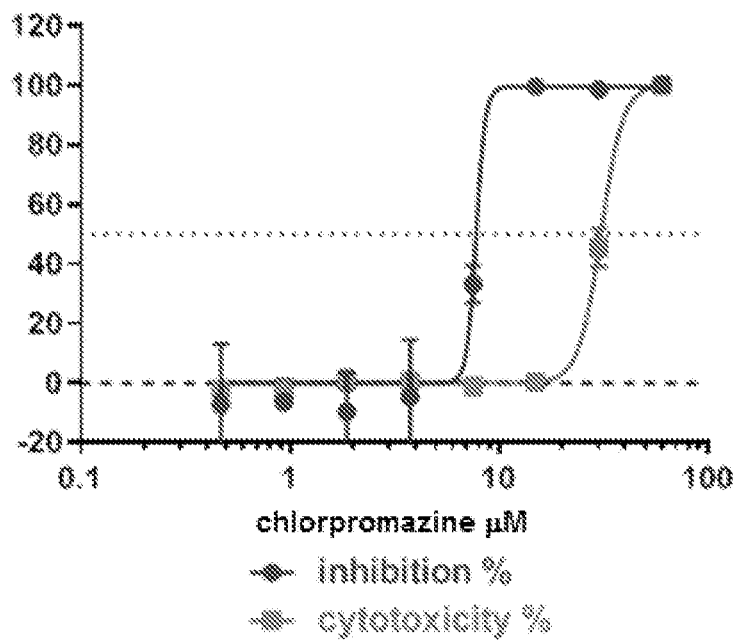
FIG. 3A depicts the antiviral activity of the control compound chlorpromazine HCl on SARS-CoV2 infected Vero E6 cells at a Multiplicity of Infection 0.6 as reported in Tables 4A and 4D.
Figure 3B:
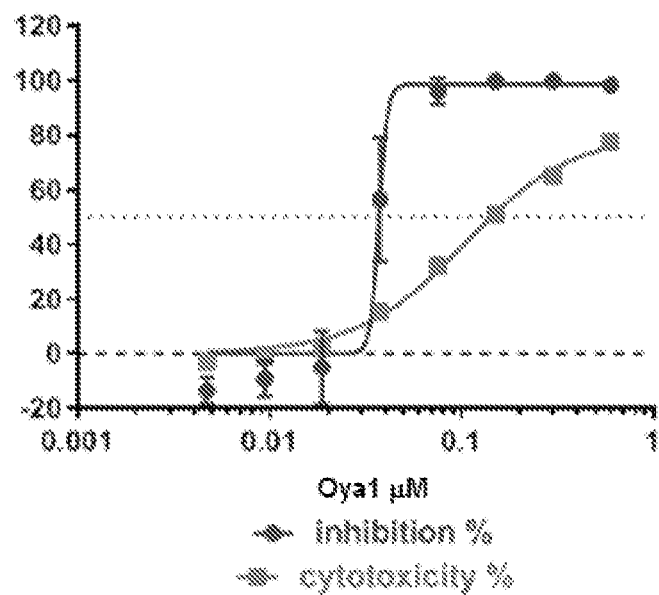
FIG. 3B depicts the antiviral activity of Oya1 on SARS-CoV2 infected Vero E6 cells at a Multiplicity of Infection 0.6 as reported in Tables 4B and 4E.
Figure 3C:
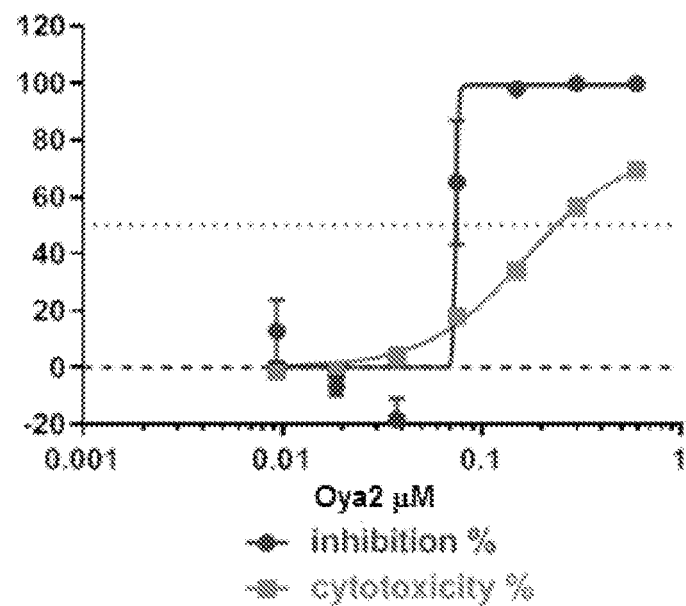
FIG. 3C depicts the antiviral activity of Oya2 on SARS-CoV2 infected Vero E6 cells at a Multiplicity of Infection 0.6 as reported in Tables 4C and 4F. The percent inhibition that the test compounds displayed is indicated by (●), whereas the percent toxicity is indicated by (■).
Figure 4:
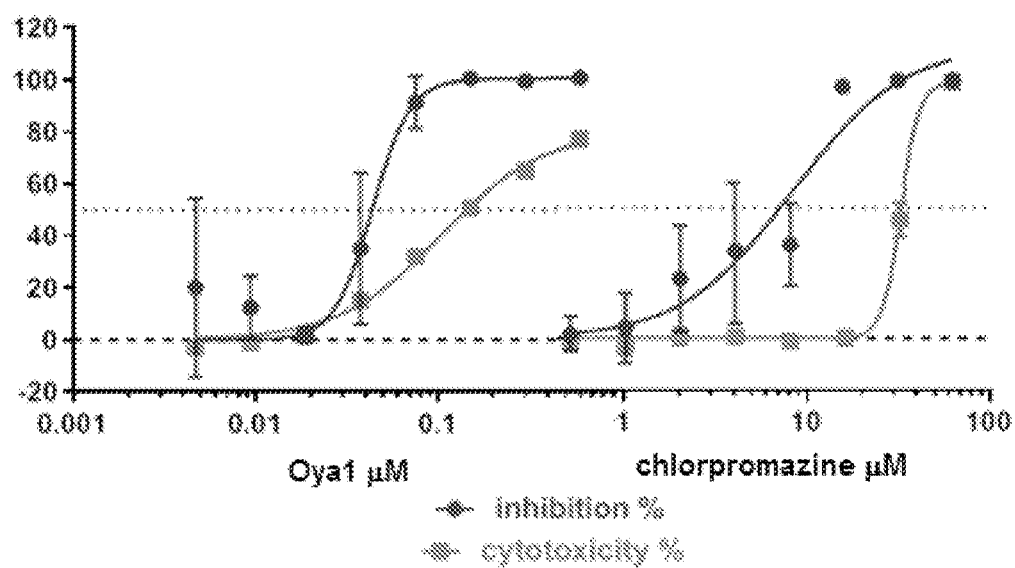
FIG. 4 depicts the antiviral activity shown in FIG. 2A and FIG. 2B on the same graph. As shown, there is a 1000-fold increase in activity for Oya1 over chlorpromazine HCl. The percent inhibition that the test compounds displayed is indicated by (●), whereas the percent toxicity is indicated by (■).
Figure 5:
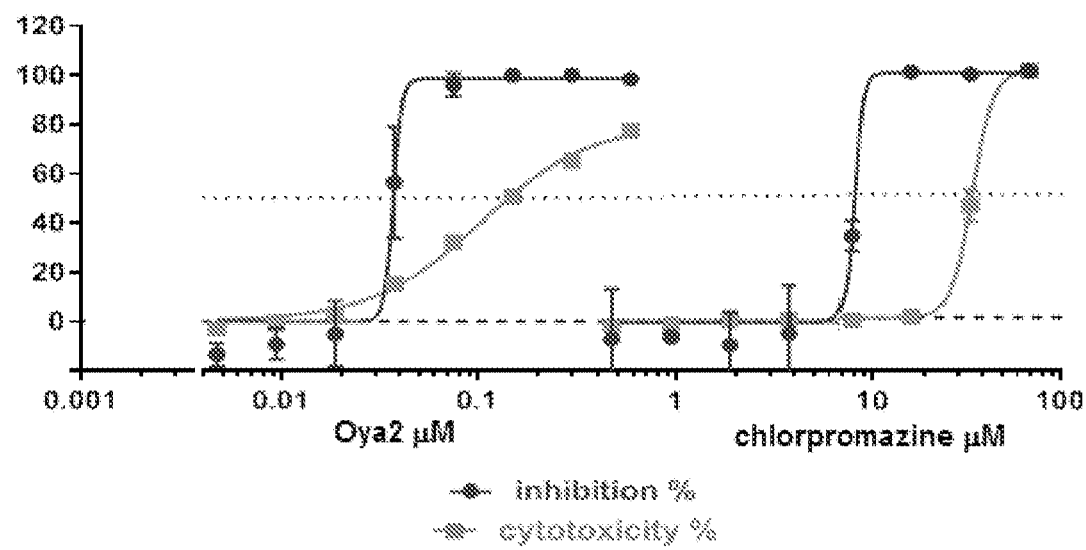
FIG. 5 depicts the antiviral activity shown in FIG. 3A and FIG. 3B on the same graph. As shown, there is a 1000-fold increase in activity for Oya1 over chlorpromazine HCl. The percent inhibition that the test compounds displayed is indicated by (●), whereas the percent toxicity is indicated by (■).

Tables 4A-4F below disclose the results of the SARS-CoV2-E6 assay with a multiplicity of infection (MOI) of 0.6 on Plate 2. All tests were run in triplicate. The inhibition results are shown in Tables 4A-4C whereas the cytotoxicity tests are shown in Tables 4D-4F. These data can be seen graphically in FIGS. 3A-3C. The results are also shown in FIG. 5

TABLE 4A

Inhibition Chlorpromazine HCl MOI 0.6

| Concentration (μM) | Test 1 | Test 2 | Test 3 |
|---|---|---|---|
| 0.4688 | −13.574571 | 21.32088 | 10.58631213 |
| 0.9375 | 5.9162891 | 8.137793 | 6.305457682 |
| 1.875 | −6.9262742 | 16.34276 | 2.592140759 |
| 3.75 | −8.5153793 | 25.26121 | 8.105362391 |
| 7.5 | 37.7470363 | 47.7357 | 39.12534175 |
| 15 | 99.7351059 | 99.19432 | 100.0302254 |

TABLE 4A-continued

Inhibition Chlorpromazine HCl MOI 0.6

| Concentration (µM) | Test 1 | Test 2 | Test 3 |
|---|---|---|---|
| 30 | 100.030225 | 96.31691 | 100.0302254 |
| 60 | 100.030225 | 100.0302 | 100.0302254 |

TABLE 4B

Inhibition Oya1 MOI 0.6

| Concentration (µM) | Test 1 | Test 2 | Test 3 |
|---|---|---|---|
| 0.0047 | 1.732727 | −3.975079 | 4.262323 |
| 0.0094 | 10.21336 | 3.435339 | −0.47256 |
| 0.0188 | 0.030124 | 2.916448 | 21.54789 |
| 0.0375 | 59.37832 | 43.50349 | 83.02032 |
| 0.075 | 91.85606 | 97.58819 | 100.0302 |
| 0.15 | 99.6777 | 100.0302 | 100.0302 |
| 0.3 | 100.0302 | 100.0302 | 100.0302 |
| 0.6 | 99.65403 | 96.03638 | 100.0302 |

TABLE 4C

Inhibition Oya2 MOI 0.6

| Concentration (µM) | Test 1 | Test 2 | Test 3 |
|---|---|---|---|
| 0.0047 | 6.759488 | 2.31648 | 2.31648 |
| 0.0094 | 33.92021 | 22.21272 | 22.21272 |
| 0.0188 | 9.743124 | 4.635276 | 4.635276 |
| 0.0375 | −1.2509 | −10.9963 | −10.9963 |
| 0.075 | 83.13382 | 77.73412 | 77.73412 |
| 0.15 | 97.4455 | 99.76267 | 99.76267 |
| 0.3 | 100.0302 | 99.75765 | 99.75765 |
| 0.6 | 99.64512 | 100.0302 | 100.0302 |

TABLE 4D

Cytotoxicity Chlorpromazine HCl MOI 0.6

| Concentration (µM) | Test 1 | Test 2 | Test 3 |
|---|---|---|---|
| 0.4688 | −1.92226 | −2.47389 | −1.85479 |
| 0.9375 | −7.06067 | 0.412456 | −1.53258 |
| 1.875 | −0.89998 | 4.449293 | −1.16314 |
| 3.75 | 0.005904 | 0.469812 | 1.571381 |
| 7.5 | −1.09398 | −3.32579 | 1.193507 |
| 15 | 1.600059 | 0.673931 | −1.39763 |
| 30 | 38.61481 | 46.71716 | 51.33768 |
| 60 | 99.94589 | 99.93324 | 99.97643 |

TABLE 4E

Cytotoxicity Oya1 MOI 0.6

| Concentration (µM) | Test 1 | Test 2 | Test 3 |
|---|---|---|---|
| 0.0047 | −3.31399 | −2.16687 | −3.38484 |
| 0.0094 | −0.23533 | −1.9307 | −0.58125 |
| 0.0188 | −0.57609 | 5.048156 | 2.473892 |
| 0.0375 | 14.23183 | 14.78684 | 16.69476 |
| 0.075 | 29.55765 | 33.63666 | 33.59955 |
| 0.15 | 49.52422 | 51.35623 | 51.37142 |
| 0.3 | 66.56565 | 64.56494 | 64.1314 |
| 0.6 | 79.77773 | 76.75643 | 75.87753 |

TABLE 4F

Cytotoxicity Oya2 MOI 0.6

| Concentration (µM) | Test 1 | Test 2 | Test 3 |
|---|---|---|---|
| 0.0047 | −2.539682 | −1.465104 | −2.75055 |
| 0.0094 | 0.449568419 | −3.730659 | −1.04674 |
| 0.0188 | −1.94588057 | −1.045057 | −1.4651 |
| 0.0375 | 0.621635881 | 5.5913491 | 5.689191 |
| 0.075 | 16.0756557 | 19.631717 | 18.12866 |
| 0.15 | 35.3674547 | 35.252743 | 31.56173 |
| 0.3 | 55.54489506 | 56.531753 | 57.44101 |
| 0.6 | 69.73539989 | 68.706369 | 69.50935 |

MOI 1.3 Plate 1

Figure 6A:
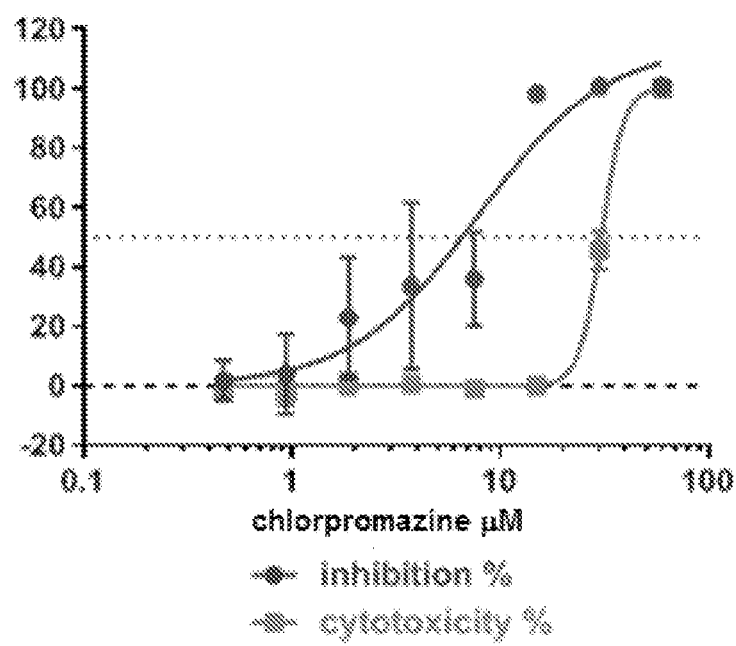
FIG. 6A depicts the antiviral activity of the control compound chlorpromazine HCl on SARS-CoV2 infected Vero E6 cells at a Multiplicity of Infection 1.3 as reported in Tables 5A and 5D.
Figure 6B:
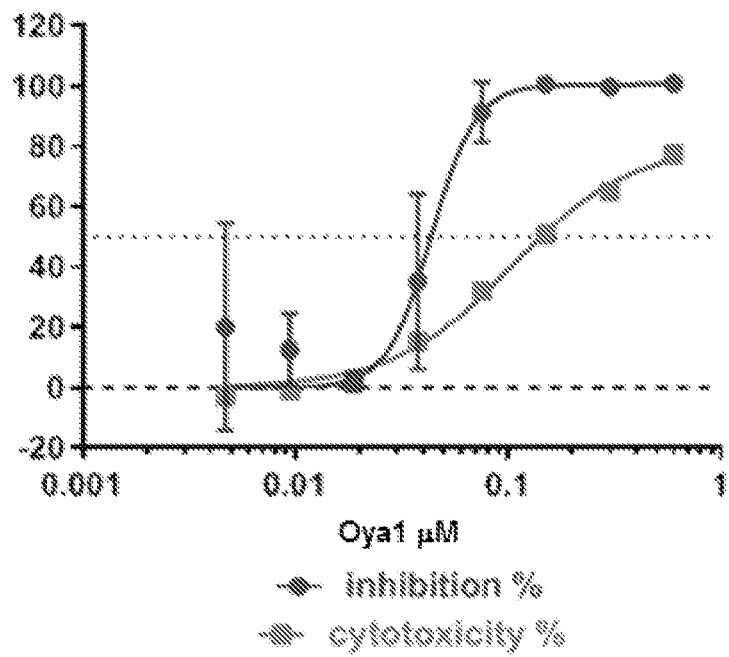
FIG. 6B depicts the antiviral activity of Oya1 on SARS-CoV2 infected Vero E6 cells at a Multiplicity of Infection 1.3 as reported in Tables 5B and 5E.
Figure 6C:
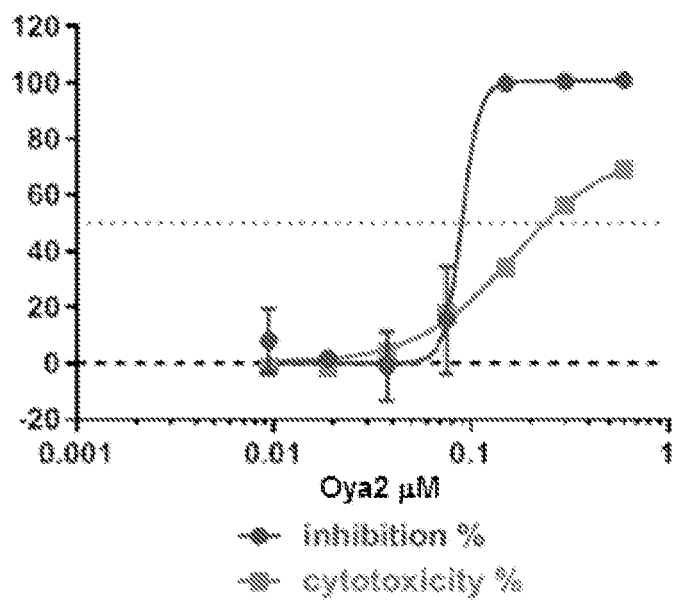
FIG. 6C depicts the antiviral activity of Oya2 on SARS-CoV2 infected Vero E6 cells at a Multiplicity of Infection 1.3 as reported in Tables 5C and 5F. The percent inhibition that the test compounds displayed is indicated by (●), whereas the percent toxicity is indicated by (■).
Figure 8:
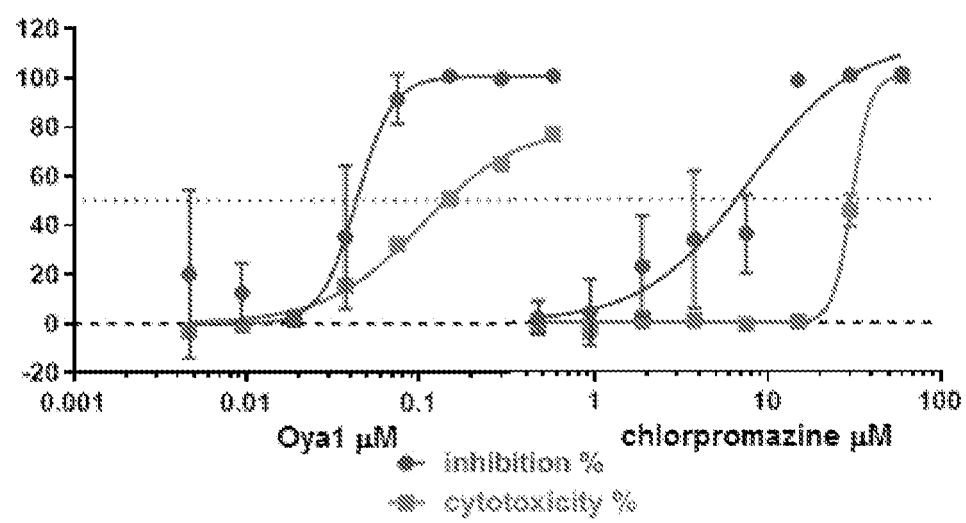
FIG. 8 depicts the antiviral activity shown in FIG. 6A and FIG. 6B on the same graph. As shown, there is a 1000-fold increase in activity for Oya1 over chlorpromazine HCl. The percent inhibition that the test compounds displayed is indicated by (●), whereas the percent toxicity is indicated by (■).

Tables 5A-5F below disclose the results of the SARS-CoV2-E6 assay with a multiplicity of infection (MOI) of 1.3 on Plate 1. All tests were run in triplicate. The inhibition results are shown in Tables 5A-5C whereas the cytotoxicity tests are shown in Tables 5D-5F. These data can be seen graphically in FIGS. 6A-6C. The results are also shown in FIG. 8.

TABLE 5A

Inhibition Chlorpromazine HCl MOI 0.6

| Concentration (µM) | Test 1 | Test 2 | Test 3 |
|---|---|---|---|
| 0.4688 | 3.56160044 | −5.83229 | 7.413422563 |
| 0.9375 | 17.2263855 | 4.601755 | 9.749126634 |
| 1.875 | 5.3656184 | 18.20503 | 45.20028514 |
| 3.75 | 13.5243302 | 65.69458 | 21.73179931 |
| 7.5 | 50.88863 | 37.75668 | 19.22892755 |
| 15 | 99.5256042 | 97.88086 | 97.65170089 |
| 30 | 100.881056 | 100.3088 | 100.8810556 |
| 60 | 100.881056 | 100.8812 | — |

TABLE 5B

Inhibition Oya1 MOI 0.6

| Concentration (µM) | Test 1 | Test 2 | Test 3 |
|---|---|---|---|
| 0.0047 | 59.64868 | 3.269057 | −2.28927 |
| 0.0094 | 6.259501 | 26.51001 | 4.731774 |
| 0.0188 | 4.894298 | 1.871349 | −1.05409 |

MOI 1.3 Plate 2

Figure 7A:
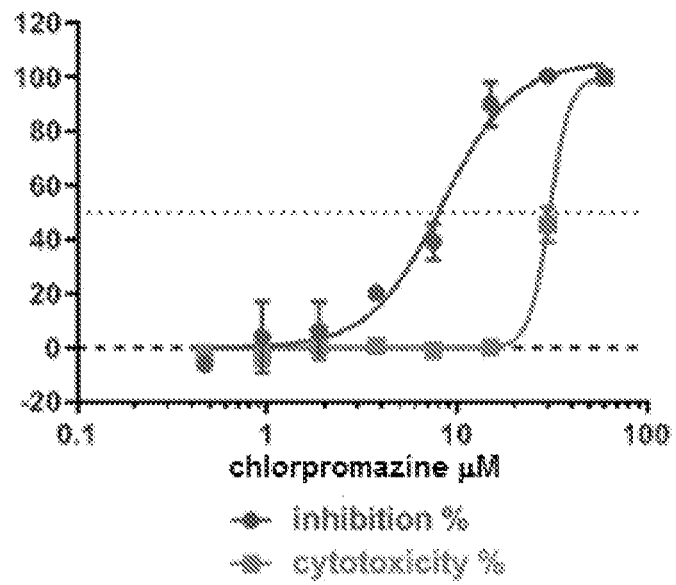
FIG. 7A depicts the antiviral activity of the control compound chlorpromazine HCl on SARS-CoV2 infected Vero E6 cells at a Multiplicity of Infection 1.3 as reported in Tables 6A and 6D.
Figure 7B:
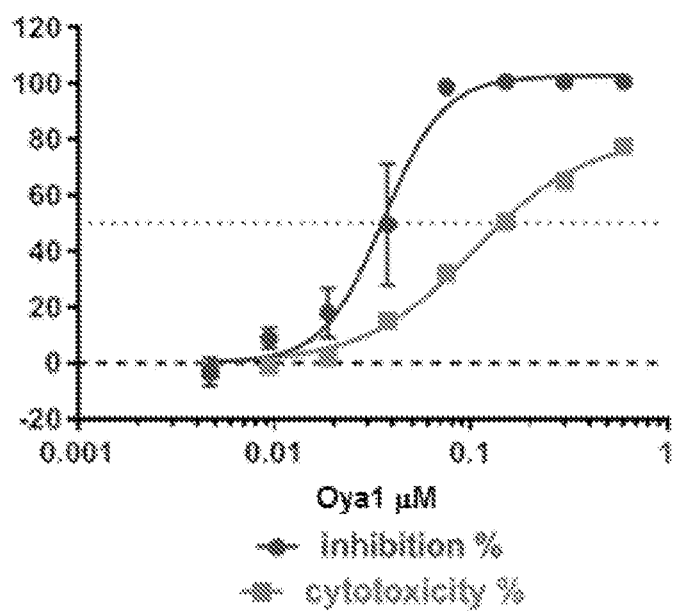
FIG. 7B depicts the antiviral activity of Oya1 on SARS-CoV2 infected Vero E6 cells at a Multiplicity of Infection 1.3 as reported in Tables 6B and 6E.
Figure 7C:
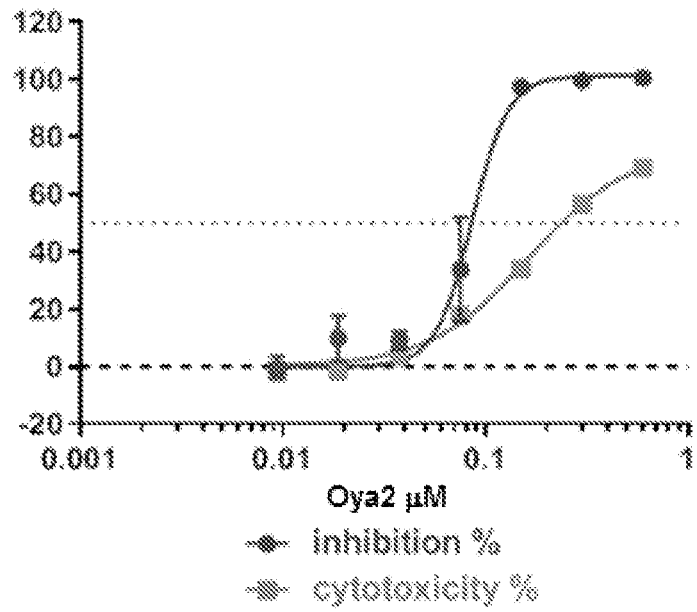
FIG. 7C depicts the antiviral activity of Oya2 on SARS-CoV2 infected Vero E6 cells at a Multiplicity of Infection 1.3 as reported in Tables 6C and 6F. The percent inhibition that the test compounds displayed is indicated by (●), whereas the percent toxicity is indicated by (■).
Figure 9:
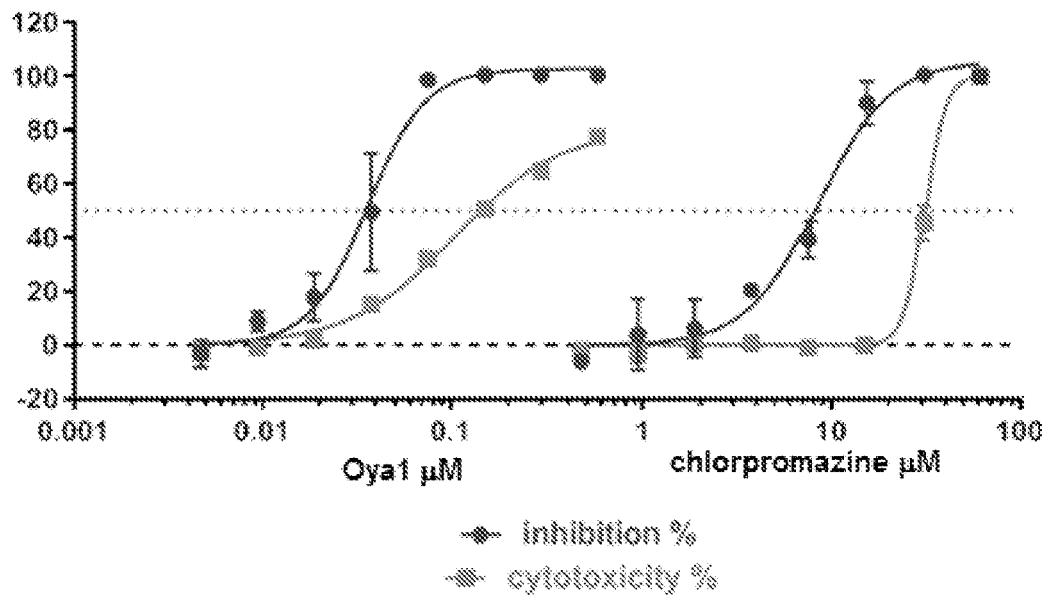
FIG. 9 depicts the antiviral activity shown in FIG. 7A and FIG. 7B on the same graph. As shown, there is a 1000-fold increase in activity for Oya1 over chlorpromazine HCl. The percent inhibition that the test compounds displayed is indicated by (●), whereas the percent toxicity is indicated by (■).
Figure 10A:
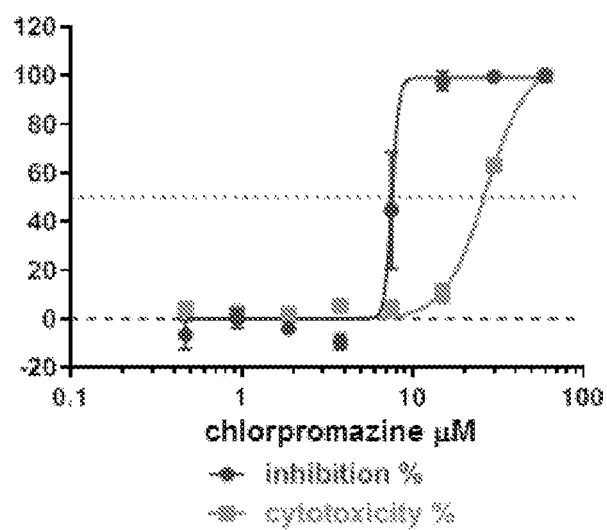
FIG. 10A depicts the antiviral activity of the control compound chlorpromazine HCl on SARS-CoV2 infected Vero E6 cells at a Multiplicity of Infection 0.2 as reported in Tables 11A and 11D.
Figure 10B:
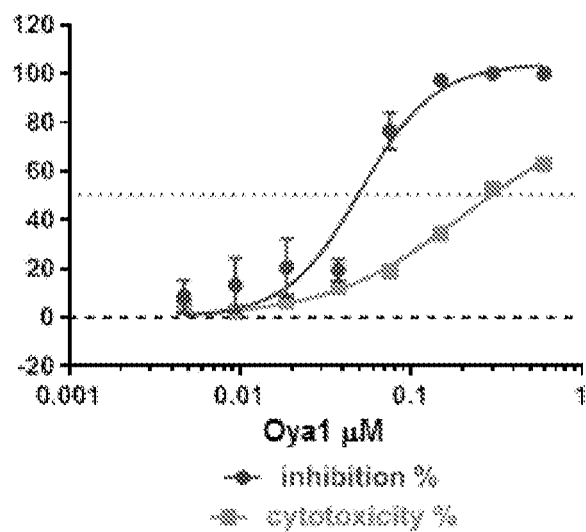
FIG. 10B depicts the antiviral activity of Oya1 on SARS-CoV2 infected Vero E6 cells at a Multiplicity of Infection 0.2 as reported in Tables 11B and 11E.
Figure 10C:
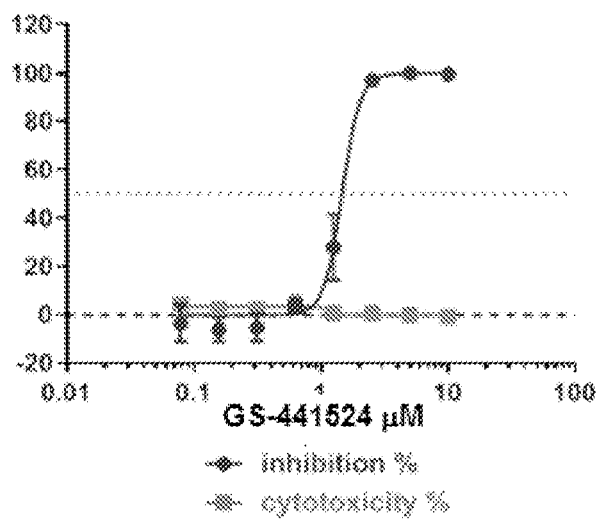
FIG. 10C depicts the antiviral activity of GS-441524 on SARS-CoV2 infected Vero E6 cells at a Multiplicity of Infection 0.2 as reported in Tables 11C and 11F. The percent inhibition that the test compounds displayed is indicated by (●), whereas the percent toxicity is indicated by (■).

Tables 6A-6F below disclose the results of the SARS-CoV2-E6 assay with a multiplicity of infection (MOI) of 1.3 on Plate 2. All tests were run in triplicate. The inhibition results are shown in Tables 6A-6C whereas the cytotoxicity tests are shown in Tables 6D-6F. These data can be seen graphically in FIGS. 7A-7C. The results are also shown in FIG. 9.

TABLE 5B-continued

Inhibition Oya1 MOI 0.6

| Concentration (μM) | Test 1 | Test 2 | Test 3 |
|---|---|---|---|
| 0.0375 | 52.59513 | 1.660068 | 51.50622 |
| 0.075 | 93.75122 | 100.0792 | 80.41927 |
| 0.15 | 100.8812 | 100.8812 | 100.3795 |
| 0.3 | 100.4418 | 97.58669 | 100.8812 |
| 0.6 | 100.8812 | 100.8812 | 100.8812 |

TABLE 5C

Inhibition Oya2 MOI 0.6

| Concentration (μM) | Test 1 | Test 2 | Test 3 |
|---|---|---|---|
| 0.0047 | −4.54835 | −2.30552 | −5.00342 |
| 0.0094 | −4.56461 | 12.18398 | 17.53868 |
| 0.0188 | 1.887602 | −0.51776 | 4.439231 |
| 0.0375 | 2.570203 | −14.7549 | 9.136178 |
| 0.075 | 25.50236 | 27.12135 | −6.82369 |
| 0.15 | 99.61873 | 100.5487 | 99.59874 |
| 0.3 | 100.8812 | 100.8812 | 99.49489 |
| 0.6 | 100.8812 | 100.8812 | 100.8812 |

TABLE 5D

Cytotoxicity Chlorpromazine HCl MOI 0.6

| Concentration (μM) | Test 1 | Test 2 | Test 3 |
|---|---|---|---|
| 0.4688 | −1.92226 | −2.47389 | −1.85479 |
| 0.9375 | −7.06067 | 0.412456 | −1.53258 |
| 1.875 | −0.89998 | 4.449293 | −1.16314 |
| 3.75 | 0.005904 | 0.469812 | 1.571381 |
| 7.5 | −1.09398 | −3.32579 | 1.193507 |
| 15 | 1.600059 | 0.673931 | −1.39763 |
| 30 | 38.61481 | 46.71716 | 51.33768 |
| 60 | 99.94589 | 99.93324 | 99.97643 |

TABLE 5E

Cytotoxicity Oya1 MOI 0.6

| Concentration (μM) | Test 1 | Test 2 | Test 3 |
|---|---|---|---|
| 0.0047 | −3.31399 | −2.16687 | −3.38484 |
| 0.0094 | −0.23533 | −1.9307 | −0.58125 |
| 0.0188 | −0.57609 | 5.048156 | 2.473892 |
| 0.0375 | 14.23183 | 14.78684 | 16.69476 |
| 0.075 | 29.55765 | 33.63666 | 33.59955 |
| 0.15 | 49.52422 | 51.35623 | 51.37142 |
| 0.3 | 66.56565 | 64.56494 | 64.1314 |
| 0.6 | 79.77773 | 76.75643 | 75.87753 |

TABLE 5F

Cytotoxicity Oya2 MOI 0.6

| Concentration (μM) | Test 1 | Test 2 | Test 3 |
|---|---|---|---|
| 0.0047 | −2.539682 | −1.465104 | −2.75055 |
| 0.0094 | 0.449568419 | −3.730659 | −1.04674 |
| 0.0188 | −1.94588057 | −1.045057 | −1.4651 |
| 0.0375 | 0.621635881 | 5.5913491 | 5.689191 |
| 0.075 | 16.0756557 | 19.631717 | 18.12866 |
| 0.15 | 35.3674547 | 35.252743 | 31.56173 |
| 0.3 | 55.54489506 | 56.531753 | 57.44101 |
| 0.6 | 69.73539989 | 68.706369 | 69.50935 |

TABLE 6A

Inhibition Chlorpromazine HCl MOI 0.6

| Concentration (μM) | Test 1 | Test 2 | Test 3 |
|---|---|---|---|
| 0.4688 | −6.2465532 | −6.00447 | −6.080122577 |
| 0.9375 | 5.50950318 | 16.22159 | −9.771857152 |
| 1.875 | 2.24141028 | 18.2944 | −1.692405253 |
| 3.75 | 19.398898 | 20.39748 | 21.5473665 |
| 7.5 | 32.1989286 | 40.21786 | 45.58903142 |
| 15 | 80.69077 | 95.71341 | 93.75406359 |
| 30 | 100.556538 | 100.5565 | 100.5565384 |
| 60 | 100.556538 | 100.5565 | — |

TABLE 6B

Inhibition Oya1 MOI 0.6

| Concentration (μM) | Test 1 | Test 2 | Test 3 |
|---|---|---|---|
| 0.0047 | −0.75434 | −8.894314 | 0.365283 |
| 0.0094 | 5.993665 | 7.809272 | 12.95349 |
| 0.0188 | 8.686816 | 26.46464 | 18.33979 |
| 0.0375 | 74.60849 | 35.1039 | 38.84102 |
| 0.075 | 99.3652 | 99.3891 | 97.8301 |
| 0.15 | 100.5565 | 100.5565 | 100.5565 |
| 0.3 | 100.5565 | 100.5565 | 100.5565 |
| 0.6 | 100.5565 | 100.5565 | 100.5565 |

TABLE 6C

Inhibition Oya2 MOI 0.6

| Concentration (μM) | Test 1 | Test 2 | Test 3 |
|---|---|---|---|
| 0.0047 | — | −12.4801 | −9.091 |
| 0.0094 | −4.5066 | −0.57278 | 3.754416 |
| 0.0188 | 15.29865 | 13.54356 | 0.925095 |
| 0.0375 | 12.22725 | 9.292018 | 6.129836 |
| 0.075 | 26.69159 | 20.42774 | 54.5309 |
| 0.15 | 98.76817 | 95.57128 | 98.32032 |
| 0.3 | 100.5565 | 97.80589 | 100.5565 |
| 0.6 | 100.5565 | 100.5565 | 100.5565 |

TABLE 6D

Cytotoxicity Chlorpromazine HCl MOI 0.6

| Concentration (μM) | Test 1 | Test 2 | Test 3 |
|---|---|---|---|
| 0.4688 | −1.92226 | −2.47389 | −1.85479 |
| 0.9375 | −7.06067 | 0.412456 | −1.53258 |
| 1.875 | −0.89998 | 4.449293 | −1.16314 |
| 3.75 | 0.005904 | 0.469812 | 1.571381 |
| 7.5 | −1.09398 | −3.32579 | 1.193507 |
| 15 | 1.600059 | 0.673931 | −1.39763 |
| 30 | 38.61481 | 46.71716 | 51.33768 |
| 60 | 99.94589 | 99.93324 | 99.97643 |

TABLE 6E

| Cytotoxicity Oya1 MOI 0.6 | | | |
|---|---|---|---|
| Concentration (μM) | Test 1 | Test 2 | Test 3 |
| 0.0047 | −3.31399 | −2.16687 | −3.38484 |
| 0.0094 | −0.23533 | −1.9307 | −0.58125 |
| 0.0188 | −0.57609 | 5.048156 | 2.473892 |
| 0.0375 | 14.23183 | 14.78684 | 16.69476 |
| 0.075 | 29.55765 | 33.63666 | 33.59955 |
| 0.15 | 49.52422 | 51.35623 | 51.37142 |
| 0.3 | 66.56565 | 64.56494 | 64.1314 |
| 0.6 | 79.77773 | 76.75643 | 75.87753 |

TABLE 6F

| Cytotoxicity Oya2 MOI 0.6 | | | |
|---|---|---|---|
| Concentration (μM) | Test 1 | Test 2 | Test 3 |
| 0.0047 | −2.539682 | −1.465104 | −2.75055 |
| 0.0094 | 0.449568419 | −3.730659 | −1.04674 |
| 0.0188 | −1.94588057 | −1.045057 | −1.4651 |
| 0.0375 | 0.621635881 | 5.5913491 | 5.689191 |
| 0.075 | 16.0756557 | 19.631717 | 18.12866 |
| 0.15 | 35.3674547 | 35.252743 | 31.56173 |
| 0.3 | 55.54489506 | 56.531753 | 57.44101 |
| 0.6 | 69.73539989 | 68.706369 | 69.50935 |

The disclosed compound Oya1 was tested further tested against SARS-CoV-2 infectivity in Vero E6 cells versus other antiviral compounds. The other antiviral compounds tested include:

i) chlorpromazine HCl having the formula:

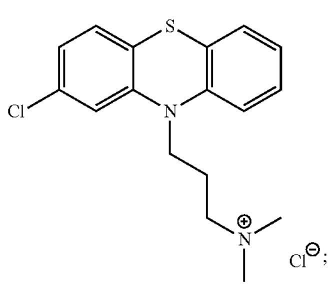 [SMILES: C[NH+](C)CCCN1c2ccccc2Sc2ccc(Cl)cc21 ; [Cl-]]

ii) GS-441524 having the formula:

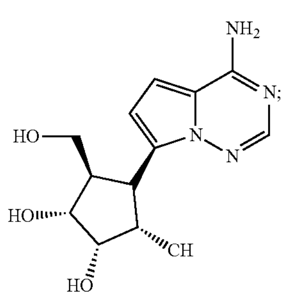

iii) remdesivir having the formula:

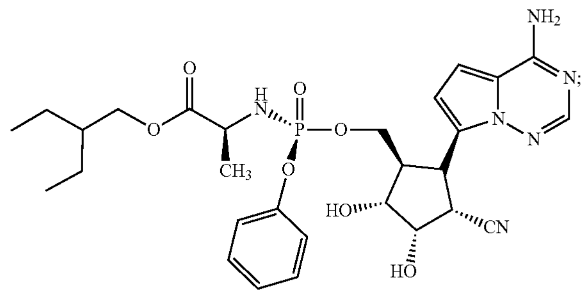

and iv) chloroquine having the formula:

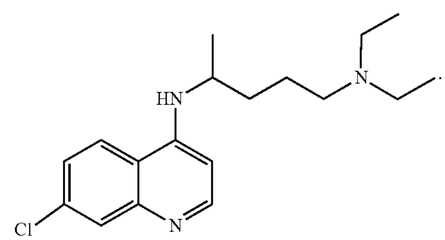 [SMILES: CCN(CC)CCCC(C)Nc1ccnc2cc(Cl)ccc12]

The results of these tests are shown below in Table 7.

TABLE 7

| Compound | $IC_{50}$ | source |
|---|---|---|
| Oya1 | 0.03 | NIAID-IRF testing |
| chlorpromazine HCl | 7.2 | NIAID-IRF testing |
| GS-441524 | 1.4 | NIAID-IRF testing |
| remdesivir | 0.77 | Wang et al.* |
| chloroquine | 1.13 | Wang et al.* |

*Wang M et al., “Remdesivir and chloroquine effectively inhibit the recently emerged novel coronavirus (2019-nCoV) in vitro,” *Cell Research* 30, 269-271 (2020).

It is particular to note that Oya1 was previously tested in Phase I clinical trials during the 1960’s for its anti-cancer activity, as detailed in Cavins et al., “Initial toxicity study of sangivamycin (NSC-65346),” *Cancer Chemotherapy Reports* 51(4), 197-200 (1967) (Cavins, 1967). The compound was shown to be inactive against cancer, but Oya1 was found to be well tolerated in humans as summarized in Table 8. These data suggest that the dosing levels indicated below produced no adverse effects.

TABLE 8

| | Testing in Humans | | |
|---|---|---|---|
| | daily | thrice weekly | weekly |
| Highest dosing regimen (μg/kg/day) | 120 × 41 days | 50-250 × 45 days | 200 × 150 days |
| Highest total dose reported (mg) | 2.8 | 1.57 | 1.73 |
| Observed toxic effect | 0 | 0 | 0 |

Important preclinical studies are shown in Table 9 below. Testing was done in African green monkeys. As seen below Oya1 was well tolerated for 10 days at 1.6 mg/kg/day (total dose 16 mg/kg) and 28 days at 0.4 mg/kg/day (total dose 11.2 mg/kg). From these studies a maximum tolerated dose (MTD) and maximum dosing and can be estimated.

TABLE 9

| NHP dosing regiment | Total dose | Effect |
|---|---|---|
| 0.4 mg/kg × 28 days | 11.2 | No effect |
| 1.6 mg/kg × 10 days | 16 | No effect |
| 1.6 mg/kg × 14 days | 22.4 | lethal |

In contrast to the aforementioned nonhuman primate and human outcomes, testing other animal models suggested a lower NOEAL and MTD for Oya1. Without wishing to be limited by theory, this can be accounted for because of the low Oya1 metabolism in rodents that leads to accumulation of Oya1 in tissues with repeated dosing of Oya1. Extensive pre-existing data on the 50% lethal dose (LD50) for a single dose and multiple daily doses in mice, dogs and rats for Oya1 are available in NCI archives and summarized in Table 10.

TABLE 10

| Oya1 $LD_{50}$ (mg/kg) | Mice | Dogs | Rats |
|---|---|---|---|
| Single dose | 4 | 2.5 | 1.2 |
| Multi dose | 0.5 × 9 days | 0.3 × 14 days | 0.05 × 24 days |
| Total dose | 4.5 | 4.2 | 1.2 |

Another study indicate that Oya1 is effective when given a single dose due to the fact that it is slowly metabolized. A published study traced the compound's metabolism in mice. It was slowly metabolized and only 40% was cleared following 12 days post injection with a half-life of 50 hours in blood (Hardesty et al., "The disposition of the antitumor agent, sangivamycin, in mice," *Cancer Res.* 34(5), 1005-1009). Without wishing to be limited by theory, our analysis has not uncovered PK and MTD studies in NHP (or humans) but given that Oya1 is well tolerated in NHP and humans compared to rodents, the long half-life of Oya1 may be unique to rodent drug metabolism and may have led to the unique toxicity finding in these animal models. It is recommended that the rodent LD is not relevant to humans. NHP pharmacokinetic (PK) and maximum tolerated dose (MTD) studies would identify the maximal tolerated single dose, maximum tolerated cumulative dose and levels of and chemical form of the drug retained in tissues. This would enable NHP efficacy studies for SARS-CoV-2 (and Ebola) through using NIAID-IRF BSL-4 facilities that would be followed by filing an IND, Phase I and then Phase II clinical trials.

It has been reported that remdesivir exhibited hepatocyte toxicity and cell culture toxicity in the low micromolar range. See, The W.H.O. R&D Blueprint for Ebola therapeutics, APPENDIX 4. Summaries of evidence from selected experimental therapeutics, which reported that "Remdesivir and the parent nucleoside analog GS-441524 were extensively profiled for in vitro cytotoxicity and mitochondrial toxicity in multiple relevant cell types. Both remdesivir and GS-441524 exhibited >3.5-fold margins in most in vitro toxicity assays. Data from in vitro studies with liver cell culture systems demonstrated that human hepatocytes are susceptible to remdesivir mediated toxicity, likely due to high cellular permeability and effective intracellular metabolism of the drug." By comparison in the 8 tests for Oya1 against SARS-CoV-2 the average toxicity margin or selectivity index was 4.8 with a high of 8.2 and low of 3.1 in a similar range reported for remdesivir. Notably in clinical trials also reported in the W.H.O. Summary "Single dose of remdesivir IV infusion from 3 to 225 mg was well tolerated with no dose limiting toxicity observed. No treatment emergent AEs were observed in more than 1 subject per arm. No evidence of renal or liver toxicity was observed. All AEs were Grade 1 or 2. Multiple-dose IV administration of remdesivir 150 mg once-daily for 7 or 14 days was generally well tolerated. No subjects had a Grade 3 or 4 treatment-emergent laboratory abnormality during the study. Reversible Grade 1 or 2 ALT or AST elevations were observed in several subjects without abnormalities in total bilirubin, alkaline phosphatase (ALP), or albumin. There was no abnormality or clinically significant change in international normalized ratio (INR) in any subjects. remdesivir did not show any effects on renal function in the multiple-dose study." These statements correlate with the lack of Oya1 toxicity in clinical trials and bodes well for Oya1 given parallels seen with remdesivir.

Figure 14:
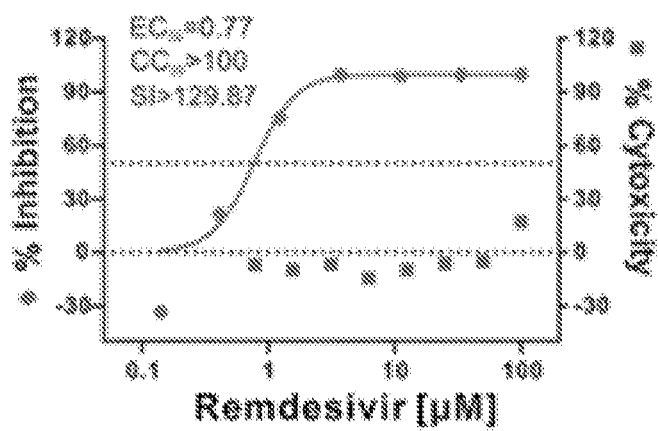
FIG. 14 depicts the inhibition of remdesivir as taken from Wang et al., "Remdesivir and chloroquine effectively inhibit the recently emerged novel coronavirus (2019-nCoV) in vitro," *Cell Research* 30, 269-271 (2020) (referred to herein as "Wang et al."). As compared to Oya1 having an $IC_{50}$ at 0.03 µM, remdesivir's $IC_{50}$ of 0.77 µM indicates that Oya1 has a 25-fold greater efficacy.

Turning to FIGS. 10B, 10C, 10D and 10F which depict the inhibition depict the SARS-CoV2-E6 inhibition of Oya1 and GS-441524, FIG. 14 depicts the inhibition of remdesivir as taken from Wang et al. These graphs show that Oya1 has an $IC_{50}$ at 0.03 µM which is 47-fold better than GS-4415124 at 1.4 µM and 25-fold better than remdesivir at 0.77 µM. Wang et al. also tested Chloroquine and reported an $IC_{50}$ of 1.13 µM and the disclosed tests at NIAID-IRF showed Chlorpromazine HCl had an $IC_{50}$ of 7.2 µM.

MOI 0.2 Plate 1

The tests depicted above were repeated wherein Chlorpromazine HCl, Oya1 and GS-441524 were tested against SARS-CoV2-E6. Tables 11A-11F below disclose the results of this assay with a multiplicity of infection (MOI) of 0.2 on Plate 1. All tests were run in triplicate. The inhibition results are shown in Tables 11A-11C whereas the cytotoxicity tests are shown in Tables 11D-11F. These data can be seen graphically in FIGS. 10A-10C.

TABLE 11A

Inhibition Chlorpromazine HCl MOI 0.2 (µM)

| Concentration (µM) | Test 1 | Test 2 | Test 3 |
|---|---|---|---|
| 0.4688 | −5.8265964 | −0.79961 | −12.71289722 |
| 0.9375 | 1.76152916 | −4.28991 | 3.226740221 |
| 1.875 | −5.5287893 | −5.15951 | −0.823436706 |
| 3.75 | −10.567686 | −5.7313 | −12.81847584 |
| 7.5 | 65.3493069 | 50.67337 | 18.53402655 |
| 15 | 93.2443049 | 99.87266 | 100.1570039 |
| 30 | 99.4684738 | 99.86646 | 99.48205384 |
| 60 | 100.157004 | 100.157 | 100.1570039 |

TABLE 11B

Inhibition Oya1 MOI 0.2 (µM)

| Concentration (µM) | Test 1 | Test 2 | Test 3 |
|---|---|---|---|
| 0.0047 | 0.927669 | 14.16222 | 10.04057 |
| 0.0094 | 2.333319 | 24.35913 | 12.99481 |
| 0.0188 | 33.59125 | 17.0569 | 10.74339 |
| 0.0375 | 22.34596 | 16.24687 | 59.6195 |
| 0.075 | 67.83897 | 81.55001 | 79.84656 |
| 0.15 | 97.23849 | 99.12206 | 95.58507 |
| 0.3 | 99.90244 | 100.157 | 99.68897 |
| 0.6 | 100.157 | 100.157 | 99.14529 |

TABLE 11C

Inhibition GS-441524 MOI 0.2 (µM)

| Concentration (µM) | Test 1 | Test 2 | Test 3 |
| --- | --- | --- | --- |
| 0.0781 | −12.0918 | 4.012951 | −3.42031 |
| 0.1563 | −9.72191 | −0.58519 | −7.80404 |
| 0.3125 | −3.33693 | −12.4373 | −0.81252 |
| 0.625 | 3.64367 | 7.765321 | 1.594757 |
| 1.25 | 12.2086 | 36.37863 | 35.04445 |
| 2.5 | 98.02123 | 95.2825 | 97.05028 |
| 5 | 99.7471 | 100.0036 | 99.77176 |
| 10 | 99.42964 | 99.4861 | 98.93123 |

TABLE 11D

Cytotoxicity Chlorpromazine HCl MOI 0.2 (µM)

| Concentration (µM) | Test 1 | Test 2 | Test 3 |
| --- | --- | --- | --- |
| 0.4688 | 4.422062 | 4.261796 | 4.169092 |
| 0.9375 | 2.740834 | 2.134335 | 3.185495 |
| 1.875 | 3.295482 | −1.49209 | 3.53274 |
| 3.75 | 5.015991 | 4.730025 | 6.541667 |
| 7.5 | 5.97602 | 4.396922 | 4.016682 |
| 15 | 6.445821 | 12.38109 | 13.79609 |
| 30 | 61.64195 | 63.60601 | 63.92654 |
| 60 | 99.96139 | 99.96626 | 99.96641 |

TABLE 11E

Cytotoxicity Oya1 MOI 0.2 (µM)

| Concentration (µM) | Test 1 | Test 2 | Test 3 |
| --- | --- | --- | --- |
| 0.0047 | 2.787971 | 3.237346 | 6.276127 |
| 0.0094 | −0.0654 | 3.441608 | 3.138358 |
| 0.0188 | 3.96326 | 6.640655 | 8.815253 |
| 0.0375 | 12.33326 | 14.8551 | 10.07382 |
| 0.075 | 18.09815 | 19.50284 | 18.92148 |
| 0.15 | 32.16076 | 35.21212 | 35.53264 |
| 0.3 | 53.54849 | 52.44548 | 51.78399 |
| 0.6 | 62.21074 | 63.79141 | 62.41343 |

TABLE 11F

Cytotoxicity GS-441524 MOI 0.2 (µM)

| Concentration (µM) | Test 1 | Test 2 | Test 3 |
| --- | --- | --- | --- |
| 0.0781 | 5.562783265 | 4.896577 | 3.083365 |
| 0.1563 | 3.845416571 | 1.1774489 | 2.3056 |
| 0.3125 | 2.076198916 | 2.0070643 | 3.380329 |
| 0.625 | 3.012087464 | 3.9239786 | 3.410183 |
| 1.25 | 2.200326975 | 0.76107 | −1.51723 |
| 2.5 | 0.358832222 | 2.8288235 | −1.30983 |
| 5 | −1.12441952 | 0.2127068 | 0.066581 |
| 10 | −1.40881419 | 0.5882334 | −1.52509 |

MOI 0.2 Plate 2

Figure 11A:
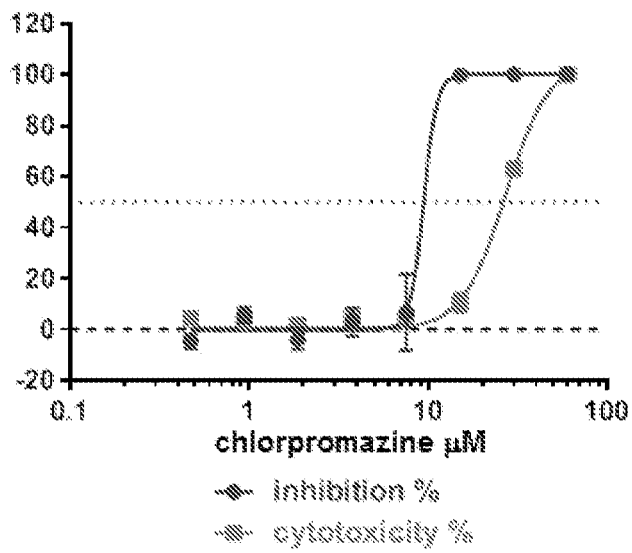
FIG. 11A depicts the antiviral activity of the control compound chlorpromazine HCl on SARS-CoV2 infected Vero E6 cells at a Multiplicity of Infection 0.2 as reported in Tables 12A and 12D.
Figure 11B:
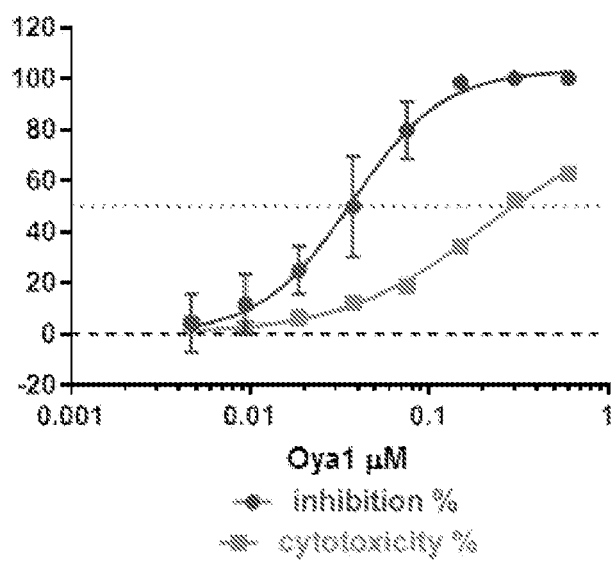
FIG. 11B depicts the antiviral activity of Oya1 on SARS-CoV2 infected Vero E6 cells at a Multiplicity of Infection 0.2 as reported in Tables 12B and 12E.
Figure 11C:
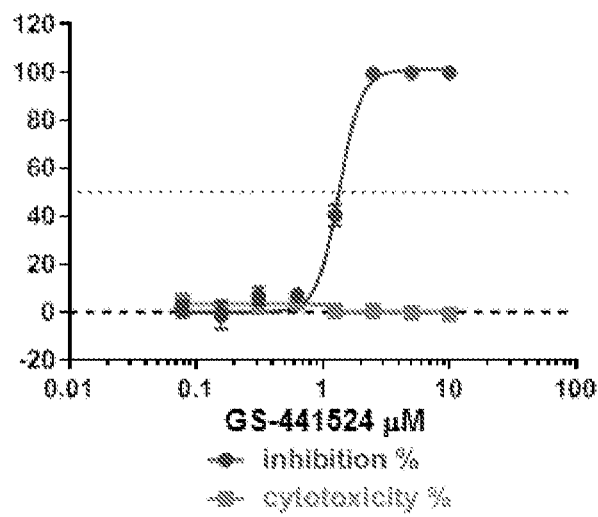
FIG. 11C depicts the antiviral activity of GS-441524 on SARS-CoV2 infected Vero E6 cells at a Multiplicity of Infection 0.2 as reported in Tables 12C and 12F. The percent inhibition that the test compounds displayed is indicated by (●), whereas the percent toxicity is indicated by (■).

The tests depicted above were repeated wherein Chlorpromazine HCl, Oya1 and GS-441524 where tested against SARS-CoV2-E6. Tables 12A-12F below disclose the results of this assay with a multiplicity of infection (MOI) of 0.2 on Plate 1. All tests were run in triplicate. The inhibition results are shown in Tables 12A-12C whereas the cytotoxicity tests are shown in Tables 12D-12F. These data can be seen graphically in FIGS. 11A-11C.

TABLE 12A

Inhibition Chlorpromazine HCl MOI 0.2 (µM)

| Concentration (µM) | Test 1 | Test 2 | Test 3 |
| --- | --- | --- | --- |
| 0.4688 | −2.5820912 | −7.81403 | −3.630835393 |
| 0.9375 | 9.29582238 | 5.206898 | 3.474702107 |
| 1.875 | 0.8125985 | −6.30572 | −6.164318913 |
| 3.75 | 9.70824993 | −0.02504 | −0.437467794 |
| 7.5 | 17.2026477 | 58.76356 | −3.9254265 |
| 15 | 100.206638 | 99.34655 | 99.86903658 |
| 30 | 100.206638 | 100.2066 | 100.206638 |
| 60 | 100.206638 | 100.2066 | 100.206638 |

TABLE 12B

Inhibition Oya1 MOI 0.2 (µM)

| Concentration (µM) | Test 1 | Test 2 | Test 3 |
| --- | --- | --- | --- |
| 0.0047 | −5.68129 | 1.718939 | 16.56633 |
| 0.0094 | 20.2664 | −1.604049 | 16.43671 |
| 0.0188 | 35.12379 | 16.91984 | 22.54064 |
| 0.0375 | 31.88507 | 46.61462 | 71.1246 |
| 0.075 | 88.5915 | 83.72132 | 67.18887 |
| 0.15 | 95.97395 | 100.2066 | 99.22259 |
| 0.3 | 100.2066 | 99.99359 | 99.98723 |
| 0.6 | 99.74001 | 100.2066 | 100.2066 |

TABLE 12C

Inhibition GS-441524 MOI 0.2 (µM)

| Concentration (µM) | Test 1 | Test 2 | Test 3 |
| --- | --- | --- | --- |
| 0.0781 | 4.947658 | 0.693762 | −1.5687 |
| 0.1563 | 4.594148 | −2.18145 | −6.71815 |
| 0.3125 | 3.733942 | 5.489705 | 10.85126 |
| 0.625 | 9.755385 | 6.609151 | 5.360085 |
| 1.25 | 45.42448 | 37.17592 | 38.21289 |
| 2.5 | 99.30707 | 99.83251 | 98.70304 |
| 5 | 99.97403 | 99.37035 | 99.68321 |
| 10 | 99.96095 | 99.10605 | 100.0591 |

TABLE 12D

Cytotoxicity Chlorpromazine HCl MOI 0.2 (µM)

| Concentration (µM) | Test 1 | Test 2 | Test 3 |
| --- | --- | --- | --- |
| 0.4688 | 4.422062 | 4.261796 | 4.169092 |
| 0.9375 | 2.740834 | 2.134335 | 3.185495 |
| 1.875 | 3.295482 | −1.49209 | 3.53274 |
| 3.75 | 5.015991 | 4.730025 | 6.541667 |
| 7.5 | 5.97602 | 4.396922 | 4.016682 |
| 15 | 6.445821 | 12.38109 | 13.79609 |
| 30 | 61.64195 | 63.60601 | 63.92654 |
| 60 | 99.96139 | 99.96626 | 99.96641 |

TABLE 12E

Cytotoxicity Oya1 MOI 0.2 (µM)

| Concentration (µM) | Test 1 | Test 2 | Test 3 |
| --- | --- | --- | --- |
| 0.0047 | 2.787971 | 3.237346 | 6.276127 |
| 0.0094 | −0.0654 | 3.441608 | 3.138358 |

TABLE 12E-continued

Cytotoxicity Oya1 MOI 0.2 (μM)

| Concentration (μM) | Test 1 | Test 2 | Test 3 |
|---|---|---|---|
| 0.0188 | 3.96326 | 6.640655 | 8.815253 |
| 0.0375 | 12.33326 | 14.8551 | 10.07382 |
| 0.075 | 18.09815 | 19.50284 | 18.92148 |
| 0.15 | 32.16076 | 35.21212 | 35.53264 |
| 0.3 | 53.54849 | 52.44548 | 51.78399 |
| 0.6 | 62.21074 | 63.79141 | 62.41343 |

TABLE 12F

Cytotoxicity GS-441524 MOI 0.2 (μM)

| Concentration (μM) | Test 1 | Test 2 | Test 3 |
|---|---|---|---|
| 0.0781 | 5.562783265 | 4.896577 | 3.083365 |
| 0.1563 | 3.845416571 | 1.1774489 | 2.3056 |
| 0.3125 | 2.076198916 | 2.0070643 | 3.380329 |
| 0.625 | 3.012087464 | 3.9239786 | 3.410183 |
| 1.25 | 2.200326975 | 0.76107 | −1.51723 |
| 2.5 | 0.358832222 | 2.8288235 | −1.30983 |
| 5 | −1.12441952 | 0.2127068 | 0.066581 |
| 10 | −1.40881419 | 0.5882334 | −1.52509 |

MOI 0.4 Plate 1

Figure 12A:
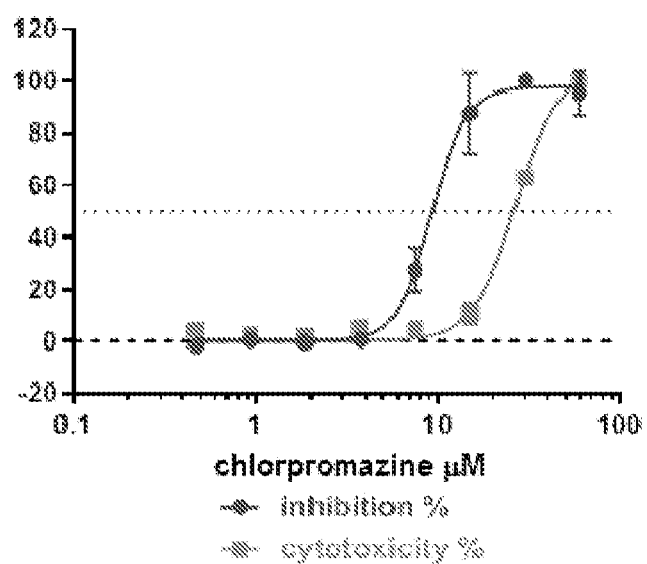
FIG. 12A depicts the antiviral activity of the control compound chlorpromazine HCl on SARS-CoV2 infected Vero E6 cells at a Multiplicity of Infection 0.4 as reported in Tables 13A and 13D.
Figure 12B:
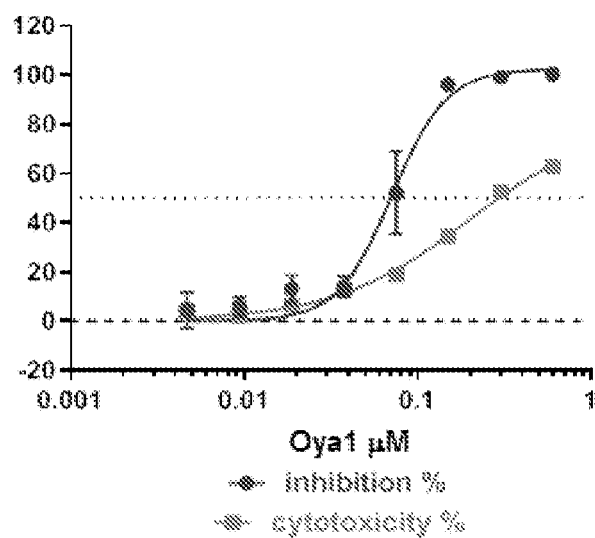
FIG. 12B depicts the antiviral activity of Oya1 on SARS-CoV2 infected Vero E6 cells at a Multiplicity of Infection 0.4 as reported in Tables 13B and 13E.
Figure 12C:
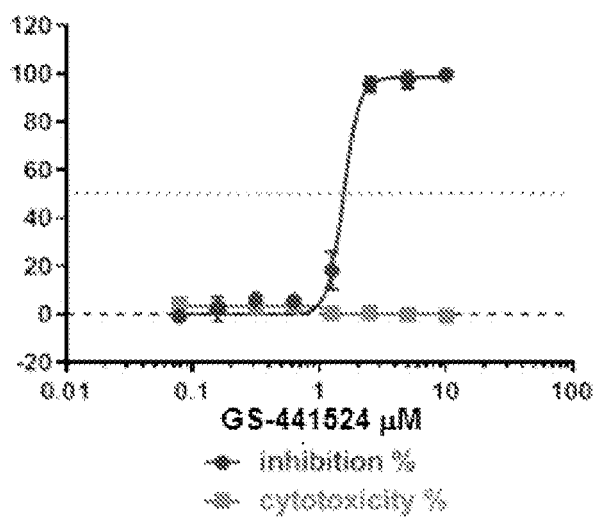
FIG. 12C depicts the antiviral activity of GS-441524 on SARS-CoV2 infected Vero E6 cells at a Multiplicity of Infection 0.4 as reported in Tables 13C and 13F. The percent inhibition that the test compounds displayed is indicated by (●), whereas the percent toxicity is indicated by (■).

The tests depicted above were repeated wherein Chlorpromazine HC, Oya1 and GS-441524 where tested against SARS-CoV2-E6. Tables 13A-13F below disclose the results of the assay with a multiplicity of infection (MOI) of 0.2 on Plate 1. All tests were run in triplicate. The inhibition results are shown in Tables 13A-13C whereas the cytotoxicity tests are shown in Tables 13D-13F. These data can be seen graphically in FIGS. 12A-12C.

TABLE 13A

Inhibition Chlorpromazine HCl MOI 0.4 (μM)

| Concentration (μM) | Test 1 | Test 2 | Test 3 |
|---|---|---|---|
| 0.4688 | −3.9891326 | −2.16189 | 0.122170505 |
| 0.9375 | 0.54712139 | −0.07968 | 1.035793408 |
| 1.875 | −0.2921469 | −0.69584 | −1.173899196 |
| 3.75 | −1.9919104 | 0.037182 | 3.213615446 |
| 7.5 | 17.5766174 | 32.55578 | 31.82276056 |
| 15 | 69.3981583 | 96.93433 | 95.98139779 |
| 30 | 99.9210247 | 100.2489 | 100.2488666 |
| 60 | 100.248867 | 100.2489 | 85.0678535 |

TABLE 13B

Inhibition Oya1 MOI 0.4 (μM)

| Concentration (μM) | Test 1 | Test 2 | Test 3 |
|---|---|---|---|
| 0.0047 | −2.26812 | 2.979898 | 12.44546 |
| 0.0094 | 9.364635 | 6.857484 | 1.875052 |
| 0.0188 | 6.761872 | 14.94198 | 17.42789 |
| 0.0375 | 10.94754 | 12.30735 | 18.81957 |
| 0.075 | 50.82824 | 69.60001 | 36.12529 |
| 0.15 | 95.88472 | 98.70208 | 94.16159 |
| 0.3 | 96.85571 | 100.2489 | 99.71631 |
| 0.6 | 100.2489 | 100.2489 | 100.2489 |

TABLE 13C

Inhibition GS-441524 MOI 0.4 (μM)

| Concentration (μM) | Test 1 | Test 2 | Test 3 |
|---|---|---|---|
| 0.0781 | 0.727712 | −0.46212 | −3.58544 |
| 0.1563 | −3.06489 | 2.236251 | 7.229307 |
| 0.3125 | 5.773884 | 5.88012 | 7.282424 |
| 0.625 | 4.424697 | 6.166955 | 6.995589 |
| 1.25 | 12.41359 | 14.6339 | 27.18028 |
| 2.5 | 95.26643 | 98.90605 | 92.22812 |
| 5 | 99.54017 | 93.51243 | 99.35033 |
| 10 | 99.5866 | 10.78819 | 99.77973 |

TABLE 13D

Cytotoxicity Chlorpromazine HCl MOI 0.4 (μM)

| Concentration (μM) | Test 1 | Test 2 | Test 3 |
|---|---|---|---|
| 0.4688 | 4.422062 | 4.261796 | 4.169092 |
| 0.9375 | 2.740834 | 2.134335 | 3.185495 |
| 1.875 | 3.295482 | −1.49209 | 3.53274 |
| 3.75 | 5.015991 | 4.730025 | 6.541667 |
| 7.5 | 5.97602 | 4.396922 | 4.016682 |
| 15 | 6.445821 | 12.38109 | 13.79609 |
| 30 | 61.64195 | 63.60601 | 63.92654 |
| 60 | 99.96139 | 99.96626 | 99.96641 |

TABLE 13E

Cytotoxicity Oya1 MOI 0.4 (μM)

| Concentration (μM) | Test 1 | Test 2 | Test 3 |
|---|---|---|---|
| 0.0047 | 2.787971 | 3.237346 | 6.276127 |
| 0.0094 | −0.0654 | 3.441608 | 3.138358 |
| 0.0188 | 3.96326 | 6.640655 | 8.815253 |
| 0.0375 | 12.33326 | 14.8551 | 10.07382 |
| 0.075 | 18.09815 | 19.50284 | 18.92148 |
| 0.15 | 32.16076 | 35.21212 | 35.53264 |
| 0.3 | 53.54849 | 52.44548 | 51.78399 |
| 0.6 | 62.21074 | 63.79141 | 62.41343 |

TABLE 13F

Cytotoxicity GS-441524 MOI 0.4 (μM)

| Concentration (μM) | Test 1 | Test 2 | Test 3 |
|---|---|---|---|
| 0.0781 | 5.562783265 | 4.896577 | 3.083365 |
| 0.1563 | 3.845416571 | 1.1774489 | 2.3056 |
| 0.3125 | 2.076198916 | 2.0070643 | 3.380329 |
| 0.625 | 3.012087464 | 3.9239786 | 3.410183 |
| 1.25 | 2.200326975 | 0.76107 | −1.51723 |
| 2.5 | 0.358832222 | 2.8288235 | −1.30983 |
| 5 | −1.12441952 | 0.2127068 | 0.066581 |
| 10 | −1.40881419 | 0.5882334 | −1.52509 |

MOI 0.4 Plate 2

Figure 13A:
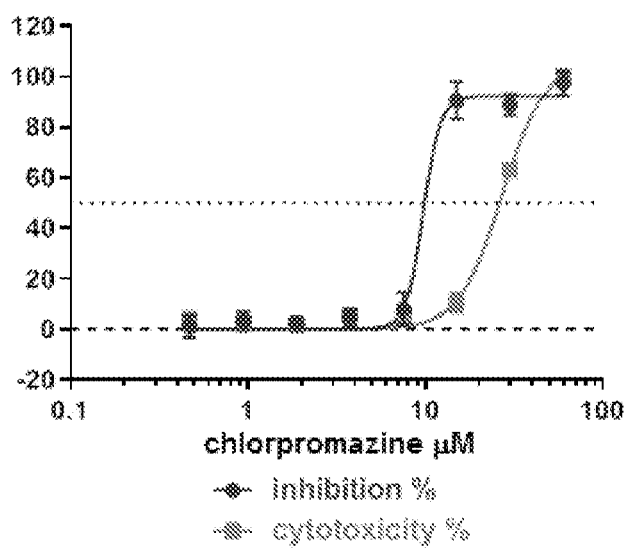
FIG. 13A depicts the antiviral activity of the control compound chlorpromazine HCl on SARS-CoV2 infected Vero E6 cells at a Multiplicity of Infection 0.4 as reported in Tables 14A and 14D.
Figure 13B:
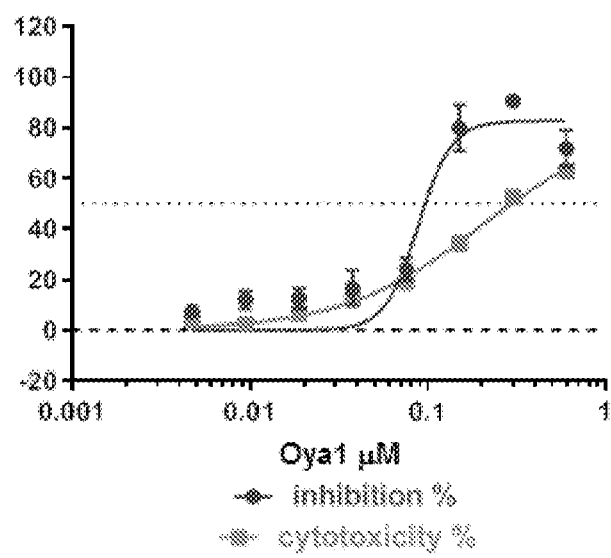
FIG. 13B depicts the antiviral activity of Oya1 on SARS-CoV2 infected Vero E6 cells at a Multiplicity of Infection 0.4 as reported in Tables 14B and 14E.
Figure 13C:
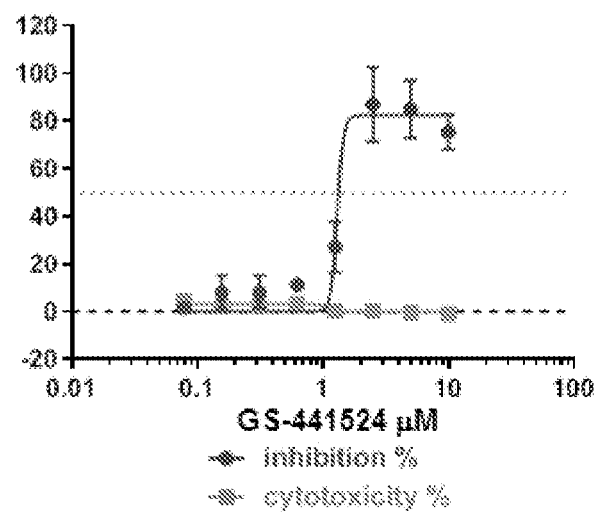
FIG. 13C depicts the antiviral activity of GS-441524 on SARS-CoV2 infected Vero E6 cells at a Multiplicity of Infection 0.4 as reported in Tables 14C and 14F. The percent inhibition that the test compounds displayed is indicated by (●), whereas the percent toxicity is indicated by (■).

The tests depicted above were repeated wherein Chlorpromazine HCl, Oya1 and GS-441524 where tested against SARS-CoV2-E6. Tables 14A-14F below disclose the results of the assay with a multiplicity of infection (MOI) of 0.2 on Plate 2. All tests were run in triplicate. The inhibition results are shown in Tables 14A-14C whereas the cytotoxicity tests are shown in Tables 14D-14F. These data can be seen graphically in FIGS. 13A-13C.

TABLE 14A

Inhibition Chlorpromazine HCl MOI 0.4 (μM)

| Concentration (μM) | Test 1 | Test 2 | Test 3 |
|---|---|---|---|
| 0.4688 | −1.6494187 | 6.01773 | −1.215429096 |
| 0.9375 | 0.90285328 | 7.526361 | 1.088848808 |
| 1.875 | 1.2955105 | 3.320795 | 2.897138643 |
| 3.75 | 0.83052169 | 6.141727 | 7.237034248 |
| 7.5 | 15.2968404 | 2.649145 | 6.658381501 |
| 15 | 90.9908196 | 82.79255 | 97.72695753 |
| 30 | 88.2794181 | 85.04516 | 93.30749718 |
| 60 | 93.88305 | 49.10669 | 100.7721276 |

TABLE 14B

Inhibition Oya1 MOI 0.4 (μM)

| Concentration (μM) | Test 1 | Test 2 | Test 3 |
|---|---|---|---|
| 0.0047 | 8.022349 | 5.573408 | 8.952326 |
| 0.0094 | 15.20384 | 12.24858 | 8.198012 |
| 0.0188 | 15.64817 | 14.1292 | 8.280676 |
| 0.0375 | 8.962659 | 18.79976 | 22.33367 |
| 0.075 | 19.8434 | 24.90661 | 28.1512 |
| 0.15 | 83.36087 | 86.80179 | 69.46287 |
| 0.3 | 91.37831 | 88.45508 | 92.27522 |
| 0.6 | 67.36525 | 67.76824 | 80.14728 |

TABLE 14C

Inhibition GS-441524 MOI 0.4 (μM)

| Concentration (μM) | Test 1 | Test 2 | Test 3 |
|---|---|---|---|
| 0.0781 | 0.799522 | 0.685859 | 3.496458 |
| 0.1563 | 0.05554 | 14.01554 | 9.758307 |
| 0.3125 | 4.219773 | 4.023445 | 16.37148 |
| 0.625 | 12.79623 | 8.291009 | 12.9719 |
| 1.25 | 15.22451 | 31.60245 | 34.82637 |
| 2.5 | 96.44979 | 95.64277 | 69.05988 |
| 5 | 72.30447 | 96.50352 | 86.1508 |
| 10 | 72.2838 | 70.43418 | 83.88786 |

TABLE 14D

Cytotoxicity Chlorpromazine HCl MOI 0.4 (μM)

| Concentration (μM) | Test 1 | Test 2 | Test 3 |
|---|---|---|---|
| 0.4688 | 4.422062 | 4.261796 | 4.169092 |
| 0.9375 | 2.740834 | 2.134335 | 3.185495 |
| 1.875 | 3.295482 | −1.49209 | 3.53274 |
| 3.75 | 5.015991 | 4.730025 | 6.541667 |
| 7.5 | 5.97602 | 4.396922 | 4.016682 |
| 15 | 6.445821 | 12.38109 | 13.79609 |
| 30 | 61.64195 | 63.60601 | 63.92654 |
| 60 | 99.96139 | 99.96626 | 99.96641 |

TABLE 14E

| Cytotoxicity Oya1 MOI 0.4 (μM) | | | |
|---|---|---|---|
| Concentration (μM) | Test 1 | Test 2 | Test 3 |
| 0.0047 | 2.787971 | 3.237346 | 6.276127 |
| 0.0094 | −0.0654 | 3.441608 | 3.138358 |
| 0.0188 | 3.96326 | 6.640655 | 8.815253 |
| 0.0375 | 12.33326 | 14.8551 | 10.07382 |
| 0.075 | 18.09815 | 19.50284 | 18.92148 |
| 0.15 | 32.16076 | 35.21212 | 35.53264 |
| 0.3 | 53.54849 | 52.44548 | 51.78399 |
| 0.6 | 62.21074 | 63.79141 | 62.41343 |

TABLE 14F

| Cytotoxicity GS-441524 MOI 0.4 (μM) | | | |
|---|---|---|---|
| Concentration (μM) | Test 1 | Test 2 | Test 3 |
| 0.0781 | 5.562783265 | 4.896577 | 3.083365 |
| 0.1563 | 3.845416571 | 1.1774489 | 2.3056 |
| 0.3125 | 2.076198916 | 2.0070643 | 3.380329 |
| 0.625 | 3.012087464 | 3.9239786 | 3.410183 |
| 1.25 | 2.200326975 | 0.76107 | −1.51723 |
| 2.5 | 0.358832222 | 2.8288235 | −1.30983 |
| 5 | −1.12441952 | 0.2127068 | 0.066581 |
| 10 | −1.40881419 | 0.5882334 | −1.52509 |

Kits

The present disclosure further relates to kits for use by medical or other trained personnel, as well as for use by trained subjects for delivery of the disclosed compositions to a subject. In general, the disclosed kits comprise:
A) an aqueous composition as described herein containing from about 0.5 mg/kg to about 10 mg/kg of the subject's body mass of the subject to which the disclose COVID-19 antiviral compound is to be administered; and
B) a means for delivering the composition to a subject.

The compositions of the disclosed kits can comprise the following concentrations of the disclosed compound: 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg/mL, 26 mg/mL, 27 mg/mL, 28 mg/mL, 29 mg/mL, 30 mg, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 101 mg/mL, 102/mL, mg/mL, 103/mL, mg/mL, 104 mg/mL, 105 mg/mL, 106 mg/mL, 107 mg/mL, 108 mg/mL, 109 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg 31 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, 200 mg/mL, 201 mg/mL, 202/mL, mg/mL, 203/mL, mg/mL, 204 mg/mL, 205 mg/mL, 206 mg/mL, 207 mg/mL, 208 mg/mL, 209 mg/mL, 210 mg/mL, 212 mg/mL, 212 mg/mL, 213 mg/mL, 214 mg/mL, 215 mg/mL, 216 mg/mL, 217 mg/mL, 218 mg/mL, 219 mg/mL, 220 mg/mL, 221 mg/mL, 222 mg/mL, 223 mg/mL, 224 mg/mL, 225 mg/mL, 226 mg/mL, 227 mg/mL, 228 mg/mL, 229 mg/mL, 230 mg/mL, 231 mg/mL, 232 mg/mL, 233 mg/mL, 234 mg/mL, 235 mg/mL, 236 mg/mL, 237 mg/mL, 238 mg/mL, 239 mg/mL, 240 mg/mL, 241 mg/mL, 242 mg/mL, 243 mg/mL, 244 mg/mL, 245 mg/mL, 246 mg/mL, 247 mg/mL, 248 mg/mL, 249 mg/mL, or 250 mg of Oya1 and/or Oya2.

The disclosed compositions can be delivered by any means in keeping with standard pharmaceutical or medical practice. The disclosed aqueous compositions can be administered in any manner chosen by the formulator. Non-limiting examples include parenteral delivery, i.e., intravenous, subcutaneous, and intramuscular. As used herein, "means for delivery" and "delivery device" are used interchangeably. Means for delivery include, but are not limited to, syringes, needles, infusion pumps, injectors. Syringes and injectors can be, for example, single-dose, multi-dose, fixed-dose or variable-dose. Examples of injectors include, but are not limited to, pen injectors, auto-injectors, and electronic patch injector systems. One convenient means for delivering the disclosed compositions is by single use disposable auto injectors. One non-limiting example is a single use injector configured like the single injector sold under the Tradename MOLLY™. Non-limiting examples of injectors are described in U.S. Pat. Nos. 7,442,185; 8,038,649; 8,062,255; 8,075,517; 8,235,952; 8,277,412; 8,529,510; and 8,551,054.

The kits can comprise any suitable means for delivery. In some embodiments the means for delivery provides for the adjustment of delivery volume. For example, the kit may comprise a delivery device that is capable of holding a single dose volume of 0.75 mL is capable of delivering 15 mg/mL of compound when the concentration of the compound is 20 mg/mL. As such, the formulator can provide delivery devices having a higher concentration of compound and adjust the delivered volume to provide an amount of compound that is less than the amount in the entire solution. In another embodiment the kit comprises a delivery device that contains a sufficient amount of a composition to allow for administration of multiple doses from the delivery device.

The following are non-limiting examples of compositions that can comprise the disclosed kits.

One example is a kit comprising:
A) an aqueous composition containing:
   a) 25 mg/mL of Oya1; and
   b) the balance a carrier system, comprising:
      i) a tonicity agent; and
      ii) water
      wherein the tonicity agent is present in an amount such that the concentration in the final composition is from about 1% to about 5% weight to volume and the carrier system is present in an amount such that the concentration of the disclosed compound has a concentration of 10 mg/mL; and
B) a means for delivering the aqueous composition.

A further aspect of the disclosure relates to kits which comprise a solid composition for reconstitution. The amount of compound in the container of dry composition can be in any convenient amount. For example, a container comprising 25 mg of a disclosed COVID-19 antiviral agent can have a demarcation line indicating a final volume of 1 mL. The user can then reconstitute the composition by adding sufficient carrier to create a composition comprising 20 mg/mL of the compound. The formulator also has options for use according to the instructions. For example, the instructions can direct the user to withdraw a sufficient amount according to the prescribed dose. If the prescribed dose is 75 mg/mL the user will withdraw 0.75 mL's of the 100 mg/mL solution for delivery to the subject. Therefore, instructions for re-constitution can afford the user with the proper method of reconstitution, as well as the amount of re-constituted formula to be delivered to a subject.

A set of instructions can be included in any of the herein described kits. The instructions can relate to the dosing amount, timing of dosing, and reconstitution of the composition when the kit contains a dry composition, methods of disposal of delivery means and unused composition, and the like.

Antiviral Disinfecting Compostions

The disclosed antiviral disinfecting compositions can be fully formulated, i.e., an aqueous based-solution ready for use, or the disclosed compositions can comprise separate components that are combined by the consumer at the time of use. For example, as disclosed herein, the COVID-19 antiviral agents and adjunct materials can be in a dry form that is admixed with water and other carriers at the time of use. Alternatively, the compositions can be impregnated or otherwise disposed upon a substrate and when ready for application to a situs, can be re-constituted by the addition of water.

In one aspect, the disclosed compositions relate to aqueous solutions comprising;
a) one or more of the disclosed coronavirus inhibitors;
b) one or more disinfecting agents; and
c) a carrier;
wherein the pH of the composition is from about 3 to about 8.

One embodiment of this aspect relates to compositions comprising:
a) one or more of the disclosed coronavirus inhibitors;
b) hydrogen peroxide; and
c) a carrier;
wherein the pH of the composition is from about 3 to about 8.

A general example of this embodiment includes compositions comprising:
a) from about 2 mM to about 100 mM of one or more of the coronavirus inhibitors;
b) from about 0.01% by weight (3 mM) to about 30% by weight ($8.8 \times 10^3$ mM) of hydrogen peroxide; and
c) the balance a carrier;
wherein the pH of the composition is from about 3 to about 8.

Another embodiment of this aspect relates to compositions comprising:
a) one or more of the disclosed coronavirus inhibitors;
b) hydrogen peroxide;
c) a buffer system; and
d) a carrier;
wherein the pH of the composition is from about 3 to about 8.

A general example, of this embodiment includes compositions comprising:
a) from about 2 mM to about 100 mM of one or more of the disclosed
b) coronavirus inhibitors;
b) from about 0.01% by weight (3 mM) to about 30% by weight ($8.8 \times 10^3$ mM) of hydrogen peroxide;
c) from about 0.01% to about 50% by weight of a buffer system; and
d) the balance a carrier;
wherein the pH of the composition is from about 3 to about 8.

A further embodiment of this aspect relates to compositions comprising:
a) one or more of the disclosed coronavirus inhibitors;
b) hydrogen peroxide;
c) a stabilizer system; and
d) a carrier;
wherein the pH of the composition is from about 3 to about 8.

A general example, of this embodiment includes compositions comprising:
a) from about 2 mM to about 100 mM of one or more of the disclosed coronavirus inhibitors;
b) from about 0.01% by weight (3 mM) to about 30% by weight ($8.8 \times 10^3$ mM) of hydrogen peroxide;
c) from about 0.01% to about 50% by weight of a stabilizer system; and
d) the balance a carrier;
wherein the pH of the composition is from about 3 to about 8.

A yet further embodiment of this aspect relates to compositions comprising:
a) one or more of the disclosed coronavirus inhibitors;
b) hydrogen peroxide;
c) a buffer system;
d) a stabilizer system; and
e) a carrier;
wherein the pH of the composition is from about 3 to about 8.

A general example, of this embodiment includes compositions comprising:
- a) from about 2 mM to about 100 mM of one or more of the disclosed coronavirus inhibitors;
- b) from about 0.01% by weight (3 mM) to about 30% by weight (8.8×10³ mM) of hydrogen peroxide;
- c) from about 0.01% to about 50% by weight of a buffer system;
- d) from about 0.01% to about 50% by weight of a stabilizer system; and
- e) the balance a carrier;
- wherein the pH of the composition is from about 3 to about 8.

In another aspect, the disclosed compositions relate to aqueous solutions comprising;
- a) one or more of the disclosed coronavirus inhibitors;
- b) one or more disinfecting agents; and
- c) a carrier;
- wherein the pH of the composition is from about 3 to about 8.

One embodiment of this aspect relates to compositions comprising:
- a) one or more of the disclosed coronavirus inhibitors;
- b) one or more peroxy acids; and
- c) a carrier;
- wherein the pH of the composition is from about 3 to about 8.

A general example of this embodiment includes compositions comprising:
- a) from about 2 mM to about 100 mM of one or more of the coronavirus inhibitors;
- b) from about 0.01% by weight (3 mM) to about 30% by weight (8.8×10³ mM) of one or more peroxy acids; and
- c) the balance a carrier;
- wherein the pH of the composition is from about 3 to about 8.

Another embodiment of this aspect relates to compositions comprising:
- a) one or more of the disclosed coronavirus inhibitors;
- b) one or more peroxy acids;
- c) a buffer system; and
- d) a carrier;
- wherein the pH of the composition is from about 3 to about 8.

A general example, of this embodiment includes compositions comprising:
- a) from about 2 mM to about 100 mM of one or more of the disclosed coronavirus inhibitors;
- b) from about 0.01% by weight (3 mM) to about 30% by weight (8.8×10³ mM) of one or more peroxy acids;
- c) from about 0.01% to about 50% by weight of a buffer system; and
- d) the balance a carrier;
- wherein the pH of the composition is from about 3 to about 8.

A further embodiment of this aspect relates to compositions comprising:
- a) one or more of the disclosed coronavirus inhibitors;
- b) one or more peroxy acids;
- c) a stabilizer system; and
- d) a carrier;
- wherein the pH of the composition is from about 3 to about 8.

A general example of this embodiment includes compositions comprising:
- a) from about 2 mM to about 100 mM of one or more of the disclosed coronavirus inhibitors;
- b) from about 0.01% by weight (3 mM) to about 30% by weight (8.8×10³ mM) of one or more peroxy acids;
- c) from about 0.01% to about 50% by weight of a stabilizer system; and
- d) the balance a carrier;
- wherein the pH of the composition is from about 3 to about 8.

A yet further embodiment of this aspect relates to compositions comprising:
- a) one or more of the disclosed coronavirus inhibitors;
- b) one or more peroxy acids;
- c) a buffer system;
- d) a stabilizer system; and
- e) a carrier;
- wherein the pH of the composition is from about 3 to about 8.

A general example, of this embodiment includes compositions comprising:
- a) from about 2 mM to about 100 mM of one or more of the disclosed coronavirus inhibitors;
- b) from about 0.01% by weight (3 mM) to about 30% by weight (8.8×10³ mM) of one or more peroxy acids;
- c) from about 0.01% to about 50% by weight of a buffer system;
- d) from about 0.01% to about 50% by weight of a stabilizer system; and
- e) the balance a carrier;
- wherein the pH of the composition is from about 3 to about 8.

In a further aspect, the disclosed compositions relate to aqueous solutions comprising;
- a) one or more of the disclosed coronavirus inhibitors;
- b) one or more surfactants; and
- c) a carrier;
- wherein the pH of the composition is from about 3 to about 8.

One embodiment of this aspect relates to compositions comprising:
- a) one or more of the disclosed coronavirus inhibitors;
- b) a surfactant system wherein the surfactant is chosen from one or more anionic surfactants, one or more zwitterionic (amphoteric) surfactants. One or more non-ionic surfactants, one or more cationic surfactants, or mixtures thereof, and
- c) a carrier.

The disclosed antiviral disinfecting compositions can comprise a surfactant system, comprising:
- i) optionally from about 25% to about 60% by weight of; on or more anionic surfactants;
- ii) optionally from about 15% to about 45% by weight of one or more zwitterionic (amphoteric) surfactants;
- iii) optionally from about 0.5% to about 10% by weight of one or more nonionic surfactants; or
- iv) optionally from about 5% to about 15% by weight of one or more cationic surfactants.

In as still further aspect of the disclosed antiviral compositions, comprise:
- a) one or more of the disclosed COVID-19 antiviral compounds;
- b) one or more quaternary ammonium salts; and
- c) the balance carriers and adjunct ingredients.

In one embodiment of this aspect, the disclosed antiviral disinfecting compositions comprise:
- a) one or more of the disclosed COVID-19 antiviral compounds;
- b) one or more quaternary ammonium salts; and
- c) one or more dispersing agents;

d) trichloromelamine; and
e) the balance carriers and adjunct ingredients.

In example of this aspect, the following solid composition is dissolved in water to deliver a liquid antiviral disinfecting composition.
a) from about 0.5% to about 5% by weight of one or more of the disclosed COVID-19 antiviral compounds;
b) from about 10% to about 90% by weight of one or more quaternary ammonium salts;
c) from about 5% to about 60% by weight of one or more dispersing agents; and d) from about 5% to about 30% by weight of trichloromelamine.

Hydrogen Peroxide

The disclosed compositions can comprise hydrogen peroxide as the source of hydrogen peroxide in any concentration from about 0.0017% by weight (0.5 mM) to about 30% by weight ($8.8\times10^3$ mM). In one embodiment, the hydrogen peroxide concentration is from about 0.5% by weight to about 5% by weight. In another embodiment, the hydrogen peroxide concentration is from about 0.1% by weight to about 1% by weight. In a yet further embodiment, he hydrogen peroxide concentration is from about 0.1% by weight to about 4% by weight.

In another embodiment of the disclosed compositions, the solid component described herein can be provided in a container or other suitable package and the user can purchase a medical source of hydrogen peroxide, for example, a 3% solution of stabilized hydrogen peroxide from a store or pharmacy and admix an amount of the purchased hydrogen peroxide with the solid component as directed by the directions listed on a kit or on a package containing the disclosed solid component.

Peroxyacids

The disclosed antimicrobial compositions can comprise from about 0.01 weight % to about 50 weight % of one or more peroxyacids. In one iteration, the disclosed compositions can comprise from about 0.05 weight % to 5 weight % of one or more peroxyacids. In another iteration, the disclosed compositions can comprise from about 0.05 weight % to 5 weight % of one or more peroxyacids. In a further iteration, the disclosed compositions can comprise from about 0.5 weight % to 10 weight % of one or more peroxyacids. In a yet another iteration, the disclosed compositions can comprise from about 1 weight % to 5 weight % of one or more peroxyacids. In a yet further iteration, the disclosed compositions can comprise from about 0.5 weight % to 2 weight % of one or more peroxyacids. In a still further iteration, the disclosed compositions can comprise from about 5 weight % to 25 weight % of one or more peroxyacids.

When the disclosed compositions comprise a two component system wherein the two components are combined prior to use, the component comprising the peroxy acid can comprise from about 0.01% to about 100% by weight of one or more peroxy acids. In one embodiment wherein the first component is a solid comprising one or more of the disclosed a-keto acids, the first component can comprised from about 0.01% to about 99.99% by weight of one or more carboxylic acids that can form a peroxy acid upon addition of a source of hydrogen peroxide by the user. In one embodiment, wherein the solid component comprises a buffer system, the first component can comprise from about 0.01% to about 90% by weight of a carboxylic acid that can form a peroxy acid upon addition of a source of hydrogen peroxide by the user.

The one or more peroxyacids can be purchased or the peroxyacids can be formed from the corresponding carboxylic acids. In one embodiment, the peroxyacid or combination of peroxyacids are be formed by combining a hydrogen peroxide ($H_2O_2$) solution with the desired amount of a carboxylic acid or carboxylic acid blend. In the case of higher molecular weight fatty acids, a solvent as part of the carrier can be required to fully solubilize the fatty acid. The $H_2O_2$ solution also can be added to previously made peroxyacids such as peroxyacetic acid, peroxyglutaric acid or various peroxy fatty acids to produce the peroxyacid composition admixture. In one iteration, the compositions can comprise from about 1 weight % to about 50 weight % of free hydrogen peroxide. In another iteration, the compositions can comprise from about, 5 weight % to about 25 weight % of hydrogen peroxide.

Suitable $C_1$-$C_{18}$ peroxyacids are peroxyfatty acids, monoperoxy- or diperoxydicarboxylic acids, and peroxy aromatic acids. The $C_2$-$C_{18}$ peroxyacids employed in the present invention may be structurally represented as follows:

$$R^{100}CO_3H$$

wherein $R^{100}$ is a hydrocarbon moiety having from about 1 to 17 carbon atoms (a $C_8$ peroxyacid is generally represented structurally as $C_7CO_3H$). $R^{100}$ can be substituted in the chain, for example, —OH, —$CO_2H$, or the chain can comprise heteroatoms as in the case of alkylether carboxylic acids. $R^{100}$ can be saturated or unsaturated, linear, branched or cyclic alkyl.

Non-limiting examples of suitable $C_2$-$C_{18}$ carboxylic fatty acids which can be reacted with hydrogen peroxide to form peroxyfatty acids include such saturated fatty acids as acetic ($C_2$), propionic ($C_3$), butyric ($C_4$), pentanoic ($C_5$), hexanoic ($C_6$), heptanoic ($C_7$), octanoic ($C_8$), nonanoic ($C_9$), decanoic ($C_{10}$), undecanoic ($C_{11}$), dodecanoic ($C_{12}$), tridecanoic ($C_{13}$), tetradecanoic ($C_{14}$), hexadecanoic ($C_{16}$), and octadecanoic ($C_{18}$). These acids can be derived from both natural and synthetic sources. Natural sources include animal and vegetable fats or oils which should be fully hydrogenated. Synthetic acids can be produced by the oxidation of petroleum wax.

Other suitable acids are the $C_6$-$C_{18}$ peroxyacids derived from the oxidation of dicarboxylic acids and aromatic acids. Suitable dicarboxylic acids include adipic acid ($C_6$) and sebacic acid ($C_{10}$). Examples of a suitable aromatic acid include benzoic acid, phthalic acid, terephthalic acid, hydroxy benzoic acid, etc. These acids can be reacted with hydrogen peroxide to form the peracid form suitable for use in the disclosed compositions. Non-limiting examples include monoperoxy- or diperoxyadipic acid, monoperoxy- or diperoxysebacic acid, and peroxybenzoic acid.

Surfactant

The disclosed compositions can comprise from about 0.05% to about 0.2% by weight of a surfactant. In further aspect, the disclosed compositions can comprise from about 0.05% to about 0.2% by weight of a non-ionic surfactant. In one embodiment the surfactant has an HLB of from about 10 to about 20. One aspect of the disclosed compositions comprises a surfactant having an HLB of from about 12 to about 18. A further aspect of the disclosed compositions comprises a surfactant having an HLB of from about 13 to about 16. Another embodiment of the disclosed compositions comprise from about 0.1% to about 0.2% by weight of a surfactant.

In one embodiment, the compositions comprise a nonionic surfactant having an HLB of from about 10 to about 20. One aspect of the disclosed compositions comprises a nonionic surfactant having an HLB of from about 12 to about 18. A further aspect of the disclosed compositions comprises a nonionic surfactant having an HLB of from about 13 to about 16. Another embodiment of the disclosed compositions comprise from about 0.1% to about 0.2% by weight of a nonionic surfactant.

Suitable surfactants include anionic surfactants, for example, linear alkyl sulfates. Non-limiting examples of linear alkyl sulfate surfactants include $C_{10}$ (decyl) sulfate, $C_{12}$ (dodecyl) sulfate, and $C_{14}$ (tetradecyl) sulfate. In addition, mixtures of two or more alkyl surfactants can be used. Suitable salts of linear alkyl sulfates include ammonium, sodium, and potassium.

In addition, branched alkyl surfactants can be used in the disclosed compositions, for example, mid-chain branched alkyl sulfate surfactants as disclosed in U.S. Pat. No. 6,232,282 included herein by reference in its entirety.

Suitable nonionic surfactants for use in the disclosed compositions include polyoxyethylene $C_6$-$C_{12}$ alkylphenyl ethers, polyoxyethylene sorbitan tri($C_{12}$-$C_{18}$)-alkanoates, polyoxyethylene sorbitan di($C_{12}$-$C_{18}$)-alkanoates, polyoxyethylene sorbitan mono-, di-, and tri-($C_{12}$-$C_{18}$)-alkanoates, and polyoxyethylene $C_{12}$-$C_{20}$ alkyl ethers.

One category of suitable nonionic surfactants for use in the disclosed compositions are the polyoxyethylene $C_6$-$C_{12}$ alkylphenyl ethers having the formula:

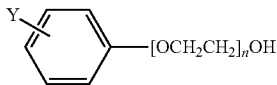

wherein Y is a $C_6$-$C_{12}$ alkyl unit and n is an index from 5 to 40. Non-limiting examples of $C_6$-$C_{12}$ alkylphenyl ethers includes polyoxyethylene(5) isooctylphenyl ethers sold under the tradenames IGEPAL™ CA-520 and IGEPAL™ CO-520, polyoxyethylene(8) isooctylphenyl ethers sold under the tradename TRITON™ X-114, polyoxyethylene(9) nonylphenyl ether sold under the tradename IGEPAL™ CO-630, polyoxyethylene(10) isooctylphenyl ether sold under the tradename TRITON™ X-100, polyoxyethylene (branched) nonylphenyl ethers sold under the tradename TRITON™ N-101, polyoxyethylene(12) nonylphenyl ether sold under the tradename IGEPAL™ CO-720, polyoxyethylene(12) isooctylphenyl ether sold under the tradename IGEPAL™ CA-720, polyoxyethylene(40) nonylphenyl ether sold under the tradename IGEPAL™ CO-890, and polyoxyethylene(40) isooctylphenyl ether sold under the tradename TRITON™ X-405.

Another category of nonionic surfactants for use in the disclosed compositions are polyoxyethylene sorbitan mono-, di-, and tri-($C_{12}$-$C_{18}$)-alkanoates, non-limiting examples of which include polyoxyethylene(20) sorbitan trioleate sold under the tradename TWEEN™ 85, polyoxyethylene(20) sorbitan monooleate sold under the tradename TWEEN™ 80, polyoxy-ethylene(20) sorbitan monostearate sold under the tradename TWEEN™ 60, polyoxyethyl-ene (20) sorbitan monopalmitate sold under the tradename TWEEN™ 40, and polyoxyethyl-ene(20) sorbitan monolaurate sold under the tradename TWEEN™ 20.

A further category of nonionic surfactants for use in the disclosed compositions are polyoxyethylene $C_9$-$C_{20}$ alkyl ethers, non-limiting examples of which include ethoxylate alcohols having the formula:

wherein R is a linear or branched alkyl group having from 6 to 20 carbon atoms and m is an integer of about 2 to about 20. On example of suitable ethoxylate alcohol surfactants are the NEODOL™ ethoxylated alcohols from Shell Chemicals. Non-limiting examples of suitable ethoxylated alcohols include NEODOL™ 91-5, NEODOL™ 91-6, NEODOL™ 91-8, NEODOL™ 91-9, NEODOL™ 23-6.5, NEODOL™ 25-5, NEODOL™ 25-7, NEODOL™ 25-9, NEODOL™ 25-12, NEODOL™ 45-7, and NEODOL™ 135-7, available from BASF.

Quaternary Ammonium Salts

The disclosed compositions comprise from about 10% to about 90% by weight of one or more quaternary ammonium salts. In one embodiment the compositions comprise from about 10% to about 90% by weight of any single quaternary ammonium salt.

In another embodiment the compositions comprise from about 20% to about 80% by weight of one or more quaternary ammonium salts. In a further embodiment the compositions comprise from about 20% to about 70% by weight of one or more quaternary ammonium salts. In another further embodiment the compositions comprise from about 20% to about 80% by weight of one or more quaternary ammonium salts. In yet further embodiment the compositions comprise from about 10% to about 60% by weight of one or more quaternary ammonium salts. In a still yet further embodiment the compositions comprise from about 30% to about 60% by weight of one or more quaternary ammonium salts. In a yet another embodiment the compositions comprise from about 40% to about 80% by weight of one or more quaternary ammonium salts. In a still another embodiment the compositions comprise from about 30% to about 70% by weight of one or more quaternary ammonium salts. In a yet still further embodiment the compositions comprise from about 30% to about 40% by weight of one or more quaternary ammonium salts. The disclosed compositions can comprise 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 88%, 82%, 83%, 84%, 85%, 86%, 87%, 88%, 89%, or 90% of one or more quaternary ammonium salts by weight of the composition.

One category of quaternary ammonium compounds relates to $C_{10}$-$C_{20}$ linear alkyl di-$C_1$-$C_4$ linear alkyl benzyl ammonium salts having the formula:

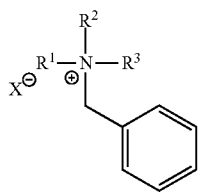

wherein $R^1$ is $C_{10}$-$C_{20}$ linear alkyl, $R^2$ and $R^3$ are each independently $C_1$-$C_4$ linear alkyl, X is fluorine, chlorine or bromine. In one embodiment X is chlorine. The following are non-limiting examples of this category of quaternary ammonium compounds: decanyl dimethyl benzyl ammonium chloride, undecanyl dimethyl benzyl ammonium chloride, dodecanyl dimethyl benzyl ammonium chloride, tridecanyl dimethyl benzyl ammonium chloride, tetradecanyl dimethyl benzyl ammonium chloride, pentadecanyl dimethyl benzyl ammonium chloride, hexadecanyl dimethyl benzyl ammonium chloride, heptadecanyl dimethyl benzyl ammonium chloride, octadecanyl dimethyl benzyl ammonium chloride, nonadecanyl dimethyl benzyl ammonium chloride, and eicosanyl dimethyl benzyl ammonium chloride.

In one embodiment of this category the quaternary ammonium compounds include: dodecanyl dimethyl benzyl ammonium chloride, tetradecanyl dimethyl benzyl ammonium chloride, hexadecanyl dimethyl benzyl ammonium chloride, and octadecanyl dimethyl benzyl ammonium chloride. The composition can comprise any number of compounds according to this category.

Another category of quaternary ammonium salts relates to $C_{10}$-$C_{20}$ linear alkyl di-$C_1$-$C_4$ linear alkyl mono-substituted benzyl ammonium salt having the formula:

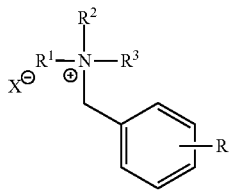

wherein R is from a $C_1$-$C_4$ linear alkyl substitution, $R^1$ is $C_{10}$-$C_{20}$ linear alkyl, $R^2$ and $R^3$ are each independently $C_1$-$C_4$ linear alkyl, X is fluorine, chlorine or bromine. In one embodiment X is chlorine.

The following are non-limiting examples of this category of quaternary ammonium compounds: decanyl dimethyl ethylbenzyl ammonium chloride, undecanyl dimethyl ethylbenzyl ammonium chloride, dodecanyl dimethyl ethylbenzyl ammonium chloride, tridecanyl dimethyl ethylbenzyl ammonium chloride, tetradecanyl dimethyl ethylbenzyl ammonium chloride, pentadecanyl dimethyl ethylbenzyl ammonium chloride, hexadecanyl dimethyl ethylbenzyl ammonium chloride, heptadecanyl dimethyl ethylbenzyl ammonium chloride, octadecanyl dimethyl ethylbenzyl ammonium chloride, nonadecanyl dimethyl ethylbenzyl ammonium chloride, and eicosanyl dimethyl ethylbenzyl ammonium chloride.

In one embodiment of this category the quaternary ammonium compounds include: dodecanyl dimethyl ethylbenzyl ammonium chloride, tetradecanyl dimethyl ethylbenzyl ammonium chloride, hexadecanyl dimethyl ethylbenzyl ammonium chloride, and octadecanyl dimethyl ethylbenzyl ammonium chloride. The composition can comprise any number of compounds according to this category. In a further embodiment the compositions comprise dodecanyl dimethyl ethylbenzyl ammonium chloride and tetradecanyl dimethyl ethylbenzyl ammonium chloride Another category of quaternary ammonium salts relates to N—$C_1$-$C_{20}$ linear alkyl substituted or unsubstituted pyridinium salt having the formula:

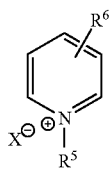

wherein $R^6$ is from 0 to 3 independently chosen $C_1$-$C_4$ linear alkyl substitutions, $R^5$ is $C_1$-$C_{20}$ linear alkyl, X is fluorine, chlorine or bromine. In one embodiment X is chlorine.

The following are non-limiting examples of pyridinium salts according to the present disclosure: N-dodecyl pyridinium chloride, N-tetradecyl pyridinium chloride, N-hexadecyl pyridinium chloride, N-octadecyl pyridinium chloride and N-eicosanyl pyridinium chloride (cetyl pyridium chloride). In one embodiment the pyridinium salt is cetyl pyridinium chloride.

Buffer System

The disclosed compositions have a pH of from about 3 to about 8. In one embodiment the pH is from about 5 to about 7. In another embodiment, the pH is from about 5 to about 6. In a further embodiment, the pH is from about 4.5 to about 5.5. In a further embodiment, the pH is about 5. In a still further embodiment, the pH is about 6. The compositions, however, can have any pH from about 3 to about 8 or any fractional part thereof, for example, a pH of 3, 3.5, 4, 4.5, 5, 5.5, 6, 6.5, 7, 7.5, and 8.

The disclosed compositions can comprise a buffer system to maintain the pH of the compositions whether pre-formulated as a liquid, diluted at the time of use, or whether constituted at the time of use, at a pH of from about 3 to about 8. In one embodiment the pH is from about 5 to about 7. In another embodiment, the pH is from about 5 to about 6. In a further embodiment, the pH is from about 4.5 to about 5.5. In a further embodiment, the pH is about 5. In a still further embodiment, the pH is about 6. The compositions, however, can comprise a buffer system to buffer the pH from about 3 to about 8 or any fractional part thereof, for example, a pH of 3, 3.5, 4, 4.5, 5, 5.5, 6, 6.5, 7, 7.5, and 8.

The formulator, depending upon the level of antimicrobial activity desired, can adjust the pH of the solution to be compatible with the type of microorganism being treated or the situs of application, for example, the skin of a burn victim, an open wound, an inert surface, or a food surface.

Carrier

The disclosed compositions can comprise a liquid carrier when not in the solid form. The user can add a liquid carrier to a dry or solid formulation to complete the composition, for example, the user in one embodiment will add an amount of water to a powder or other solid formulation. In another embodiment, the user can be directed by the instructions of a kit to add an amount of hydrogen peroxide, for example, a 3% by weight solution of hydrogen peroxide. More than one carrier can be added or more than one carrier can comprise the liquid embodiments disclosed herein.

In one embodiment, water is the carrier. In another embodiment, the carrier can be an aqueous solution of a source of hydrogen peroxide, for example, an aqueous solution of hydrogen peroxide or an aqueous solution of a source of hydrogen peroxide, i.e., a perborate. In addition, $C_1$-$C_{10}$ linear, branched, and cyclic aliphatic alcohols can be either carriers alone or can be a part of the carrier system. In one embodiment, methanol is added as a co-carrier.

Non-limiting examples of suitable organic acid buffer systems include acetic acid/sodium acetate, glycolic acid/sodium glycolate, lactic acid/sodium lactate, succinic acid/mono sodium succinate, adipic acid/mono sodium adipate, malic acid/mono sodium malate, tartaric acid/mono sodium tartrate, and the like. Non-limiting examples of suitable inorganic buffer systems include phosphate buffer systems.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Figure 17A:
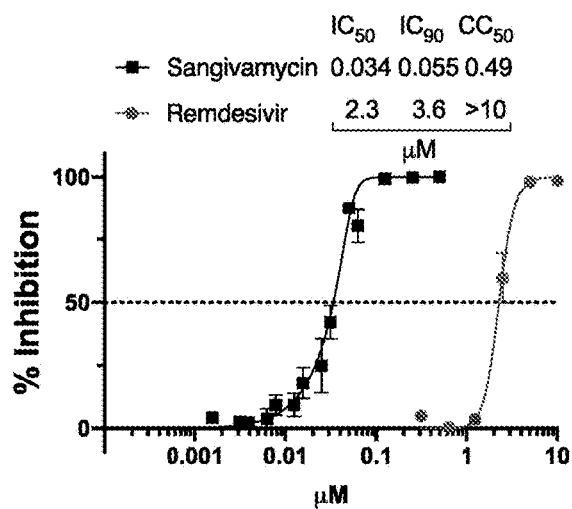
Figure 17B:
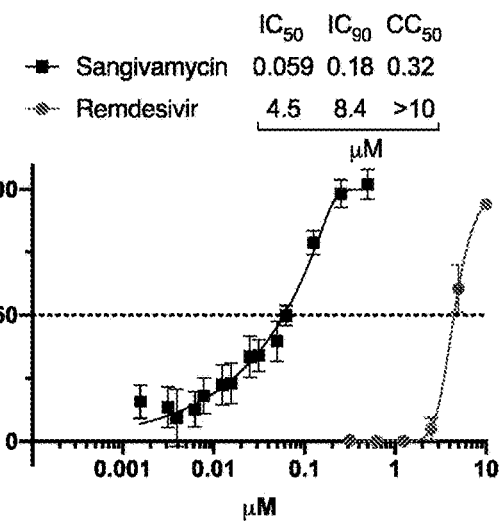

SARS-CoV-2. This proposed dosing is conservative considering the clinical doses of Remdesivir compared to the antiviral $IC_{90}$ (Table 15). In comparison, the proposed dosing is about 10-fold lower than the current dosing regimen for Remdesivir, with FIG. 17 showing Sangivamycin is >47-fold more effective against SARS-CoV-2 than Remdesivir in cells with highest infection rate (FIGS. 17A-17B).

TABLE 15

Comparison of Safe Dosing and Antiviral Activity between Sangivamycin and Remdesivir

| | Reported Safe Clinical Dosing From Cavins, et al. 1967 and Eastman, et al. 2020 | Efficacy in VeroE6/Calu3 Cells | | [2]Estimated mg/kg to achieve $IC_{90}$ | Differential between safe clinical doses and dose to achieve $IC_{90}$ |
|---|---|---|---|---|---|
| | | $IC_{90}$ (µM) | $IC_{90}$ (µg/L) | | |
| Sangivamycin | 0.12 mg/kg/day × 41 in daily dosing or up to 0.25 mg/kg/day in thrice weekly dosing or 0.3 mg/kg/day weekly dosing | 0.055/0.18 | 17/56 | 0.010 to 0.034 | 9 to 30 |
| Remdesivir | [1]1.57-1.71 mg/kg/day × 5-10 days (200 mg day 1, 100 mg/kg days 2-10) | 3.6/8.4 | 2169/5062 | 1.3 to 3.0 | 0.6 to 1.3 |

[1]Estimated based on 70 kg adult male and average 5 to 10-day doses.
[2]Dosing is based on 42 L in 70 kg adult male in a 2-compartment model.

Example 1

Clinically Safe Dosage Relative to Antiviral Activity

The in vivo animal data and human clinical data from studies conducted in the 1960s by NCI that supported the potential use of sangivamycin for the treatment of cancer, along with our estimated effective and safe antiviral dosing helped determine the proper dosing regimen for treatment of COVID-19 disease. The calculated dose required to be at the antiviral $IC_{50}$ and $IC_{90}$ is well within the safe dosing range from clinical trials performed in the 1960s (Cavins, 1967). The proposed dosing at 0.2 mg/kg for 5 days is lower than the highest single dose tested at 0.3 mg/kg wherein the MTD was not reached in humans, as that was merely the highest dose tested (Cavins, 1967). A total dose of 1 mg/kg is nearly 3-fold lower than the highest total dose tested in humans (Cavins, 1967).

Figure 15A:
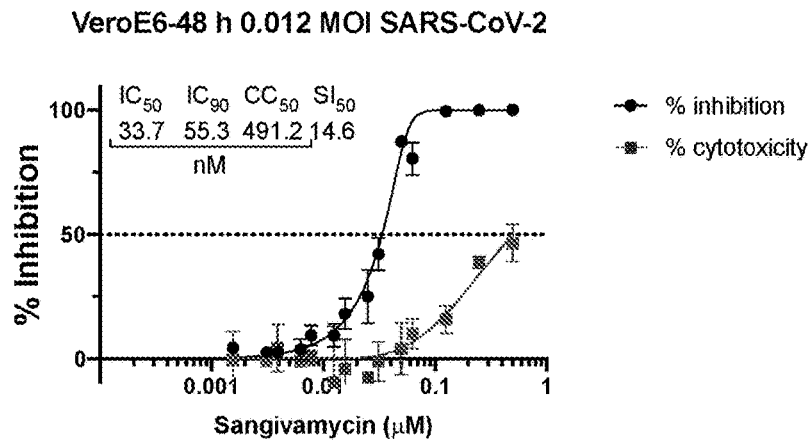
FIGS. 15A-15C are graphs of depicting antiviral activity of sangivamycin in three different cell types infected with SARS-CoV-2.
Figure 15B:
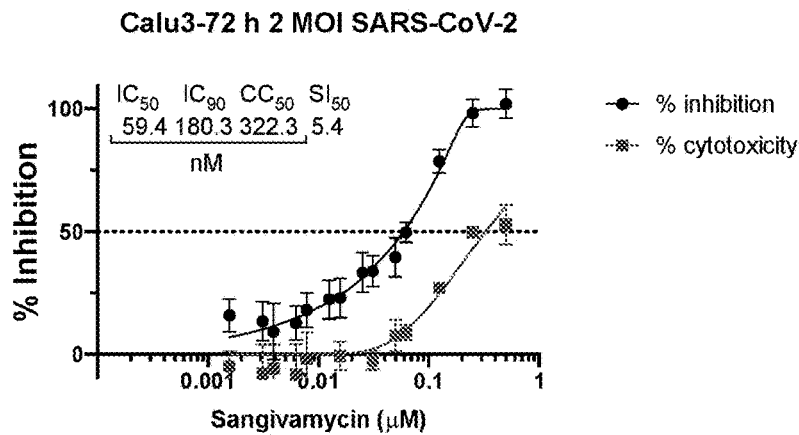
Figure 15C:
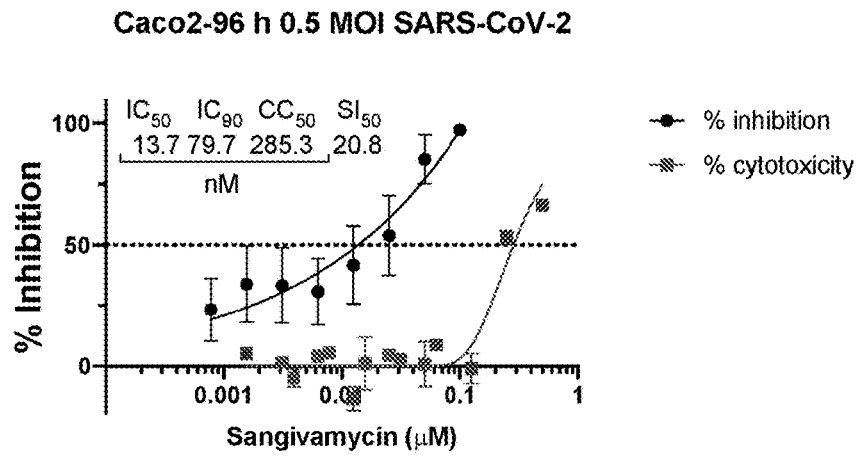

The 1974 radiotracer study in mice suggested a slow metabolism of sangivamycin (Hardesty, 1974). Assuming this is characteristic of the metabolism of sangivamycin in humans, we have estimated the amount of sangivamycin in a two-compartment model for a 70 kg adult male (extracellular and cellular water volumes will be 42 L). Our goal in the Phase 1 clinical trial is to determine the pharmacokinetics (PK) of sangivamycin in human subjects following a dose of 0.2 mg/kg per day (administered for one day and for 2 and five consecutive days as we believe this will be a safe dosing and anticipated dosing proposed for Phase II that is greater than the $IC_{90}$ for sangivamycin antiviral effect on Results As shown in FIGS. 15A-15C, three different cell types were infected with SARS-CoV-2, as follows: FIG. 15A: VeroE6 monkey kidney cells infected for 48 hours at a multiplicity of infection (MOI) of 0.012; FIG. 15B: Calu3 human lung cells infected for 72 hours at an MOI of 2; and FIG. 15C: Caco2 human intestinal cells infected for 96 hours at an MOI of 0.5. Graphs were generated in GraphPad Prism 9.0 and show the compiled data from three plates with an n of 9 for 14 concentrations of sangivamycin treatment (97% purity from Berry & associates) one hour before infection ranging from 500 to 0.78 nM, with the calculated $IC_{50}$, $IC_{90}$, $CC_{50}$ and $SI_{50}$ listed on each graph. The curves represent Perkin Elmer Operetta high content image reads in which the Perkin Elmer Columbus image analysis software identified positive cells. All values represent infectivity and cytotoxicity relative to the average of positive controls from each plate set to 100%, with the average % infected for VeroE6 at 77%±4%, for Calu3 at 76%±10%, and for Caco2 25%±6%. The cytotoxicity data have an n of 3 from a single plate read with Cell Titer-Glo and the positive controls set to 100%.

Figure 16A:
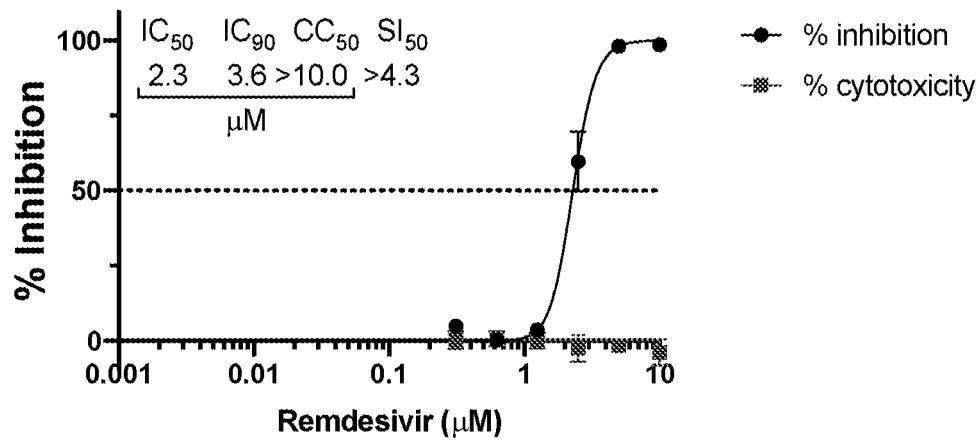
Figure 16B:
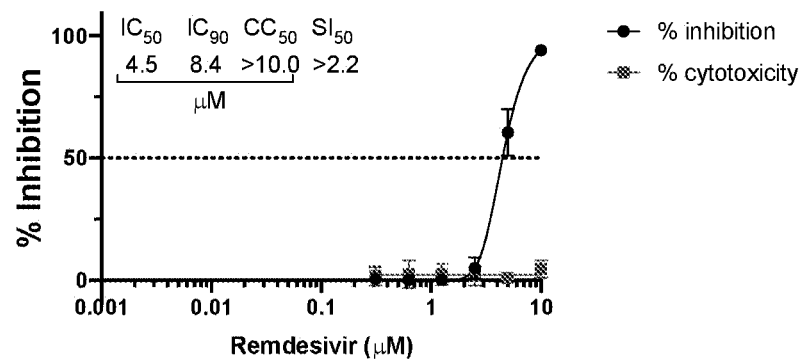
Figure 16C:
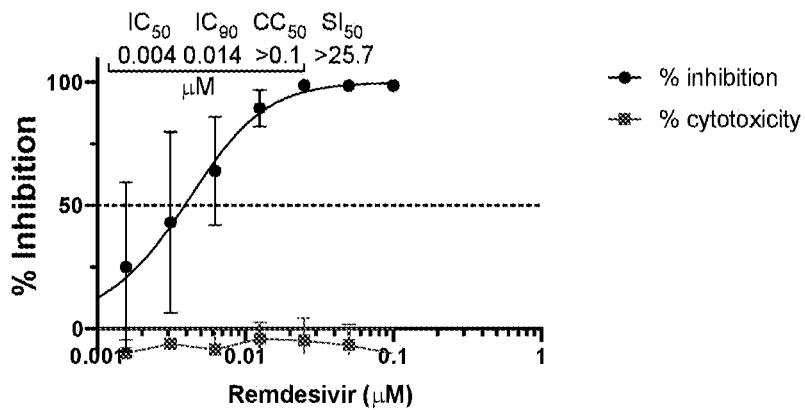

As shown in FIGS. 16A-16C, three different cell types were infected with SARS-CoV-2, as follows: FIG. 16A: VeroE6 monkey kidney cells infected for 48 hours at a multiplicity of infection (MOI) of 0.012; FIG. 16B: Calu3 human lung cells infected for 72 hours at an MOI of 2; and FIG. 16C: Caco2 human intestinal cells infected for 96 hours at an MOI of 0.5. Graphs were generated in GraphPad Prism 9.0 and show the compiled data from three plates with an n of 9 for 6 concentrations of remdesivir treatment (98% purity from BIOSYNTH) one hour before infection ranging from 10 to 0.313 µM, with the calculated $IC_{50}$, $IC_{90}$, $CC_{50}$ and $SI_{50}$ listed on each graph. The curves represent Perkin Elmer Operetta high content image reads in which the Perkin Elmer Columbus image analysis software identified positive cells. All values represent infectivity and cytotoxicity relative to the average of positive controls from each plate set to 100%, with the average % infected for VeroE6 at 77%±4%, for Calu3 at 76%±10%, and for Caco2 25%±6%. The cytotoxicity data have an n of 3 from a single plate read with Cell Titer-Glo and the positive controls set to 100%.

Figure 17C:
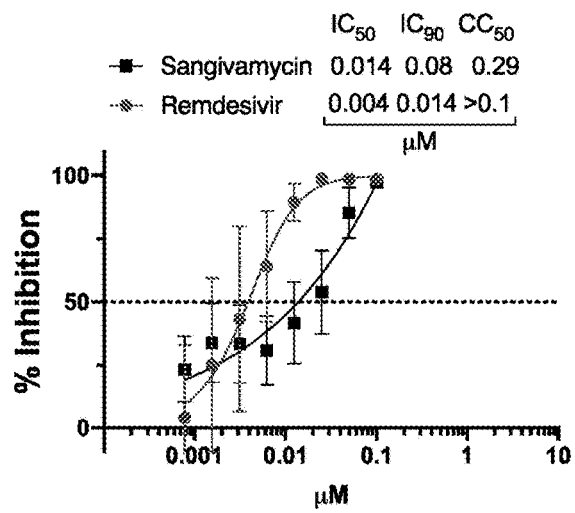

As shown in FIGS. 17A-17C, three different cell types were infected with SARS-CoV-2, as follows: FIG. 17A: VeroE6 monkey kidney cells infected for 48 hours at a multiplicity of infection (MOI) of 0.012; FIG. 17B: Calu3 human lung cells infected for 72 hours at an MOI of 2; and FIG. 17C: Caco2 human intestinal cells infected for 96 hours at an MOI of 0.5 from FIGS. 15 and 16. Graphs were generated in GraphPad Prism 9.0 and show the infectivity curves from FIGS. 15 and 16 plotted on the same graph for comparison of the differentials in efficacy between sangivamycin and remdesivir in the different cell types.

Figure 18A:
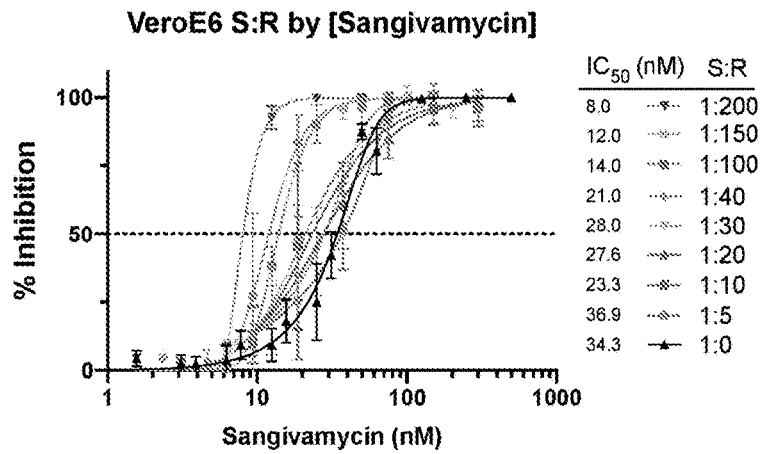
Figure 18B:
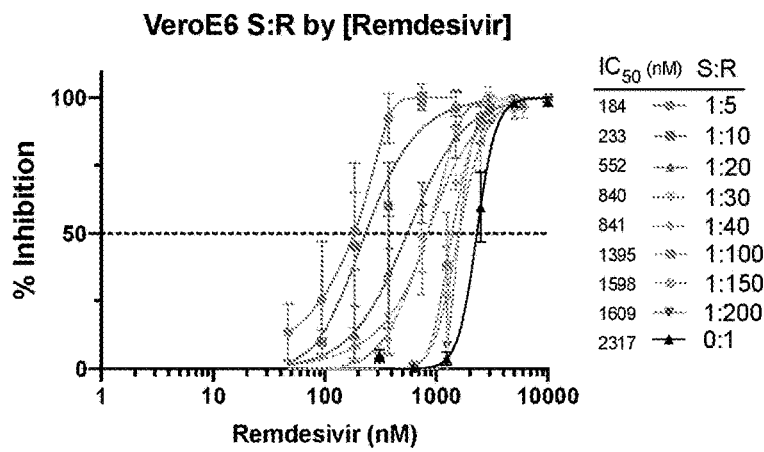
Figure 18C:
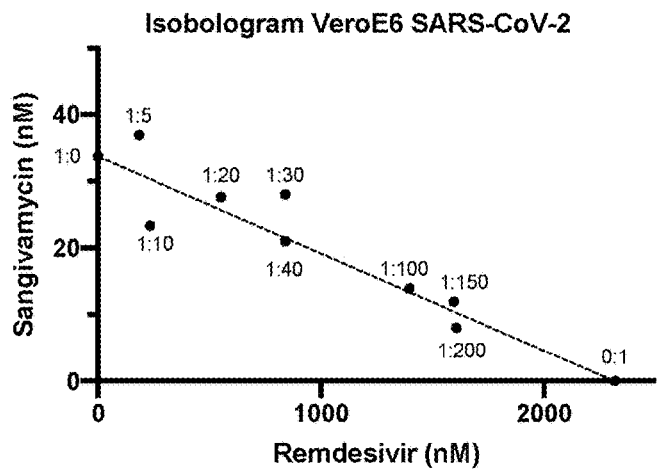

As shown in FIGS. 18A-18C, VeroE6 cells infected with SARS-CoV-2 as in FIGS. 15 and 16 were treated with combinations of sangivamycin (S) and remdesivir (R). Based on single drug treatment curves from FIGS. 15A and 16A constant ratios of sangivamycin:remdesivir (S:R) were established from 1:5, 1:10, 1:20, 1:30 and 1:40 with S ranging from 300-1.5 nM and R ranging from 6000-46 nM. For S:R 1:100, 1:150, and 1:200 the S concentrations were between 100-1.5 nM and R concentrations 10000-312 nM. The 1:0 and 0:1 curves were from the single drug experiment in FIGS. 15A and 16A. FIG. 18A illustrates the infectivity curves for each S:R plotted relative to sangivamycin concentration with IC$_{50}$ values listed on the right. FIG. 18B illustrates the infectivity curves for each S:R ratio plotted relative to remdesivir concentration with IC$_{50}$ values listed on the right. FIG. 18C illustrates an isobologram plotting the sangivamycin IC$_{50}$ values on the y-axis and the remdesivir IC$_{50}$ values on the x-axis for each constant ratio. The dotted line connects 1:0 (sangivamycin alone) to 0:1 (remdesivir alone). The S:R ratios plot along this line indicative of additivity between the two drugs in combination in VeroE6 cells.

Figure 19A:
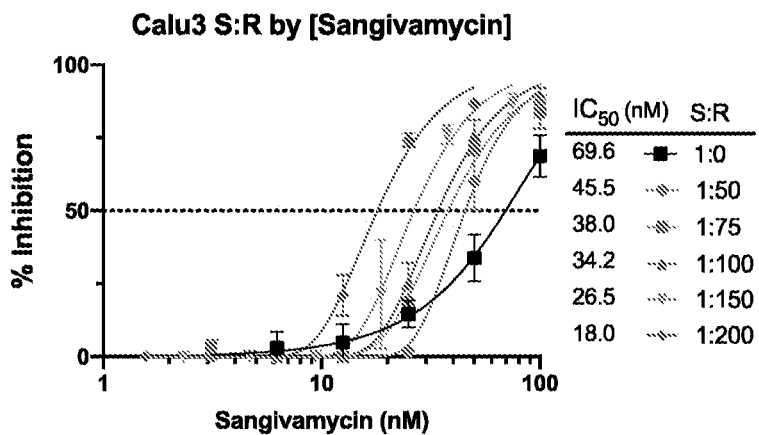
Figure 19B:
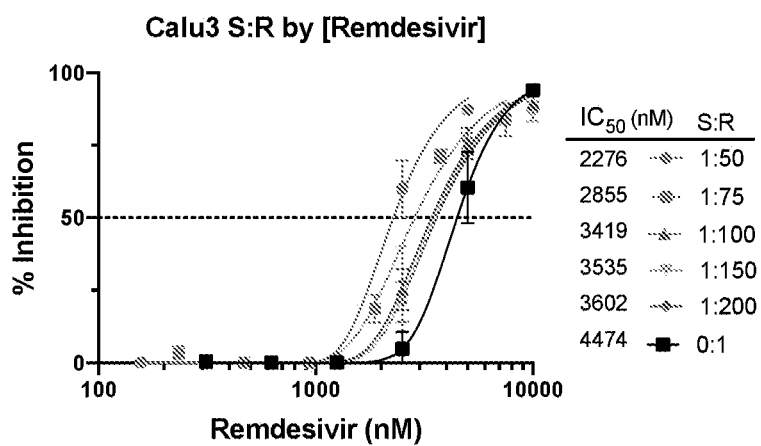
Figure 19C:
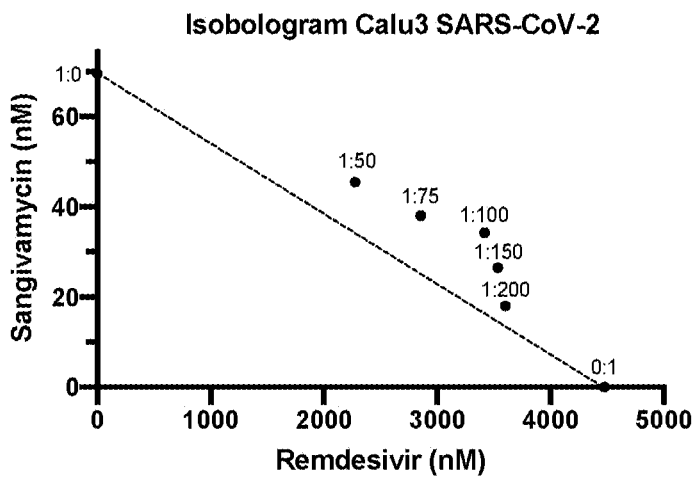

As shown in FIGS. 19A-19C, Calu3 cells infected with SARS-CoV-2 as in FIGS. 15 and 16 were treated with combinations of sangivamycin (S) and remedesivir (R). Based on single drug treatment curves from FIGS. 15B and 16B S:R ratios were established from 1:50, 1:75, 1:100, 1:150, and 1:200, the S concentrations were between 100-1.5 nM and R concentrations 10000-312 nM. FIG. 19A illustrates the infectivity curves for each S:R relative to sangivamycin concentration with IC$_{50}$ values listed on the right. FIG. 19B illustrates the infectivity curves for each S:R relative to remdesivir concentration with IC$_{50}$ values listed on the right. FIG. 19C illustrates an isobologram plotting the sangivamycin IC$_{50}$ values on the y-axis and the remdesivir IC$_{50}$ values on the x-axis for each constant ratio. The dotted line connects 1:0 (sangivamycin alone) to 0:1 (remdesivir alone). The S:R ratios plot slightly above this line indicative of mild antagonism between the two drugs in combination in Calu3 cells.

Figure 20A:
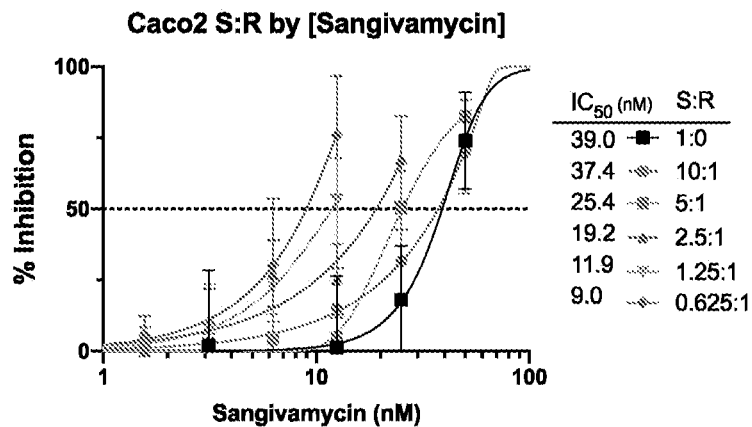
Figure 20B:
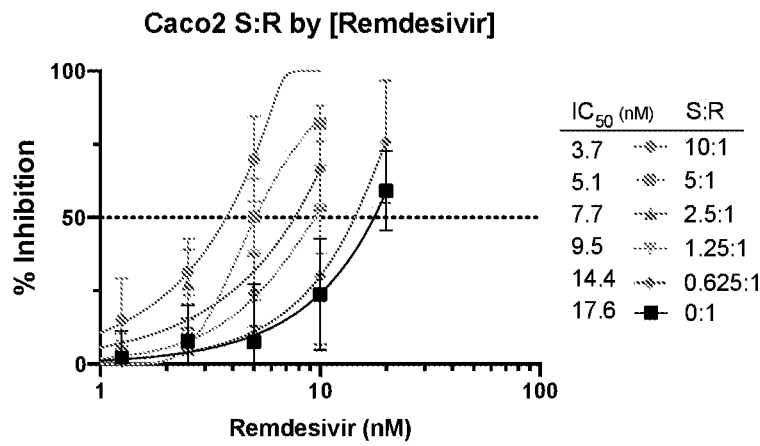
Figure 20C:
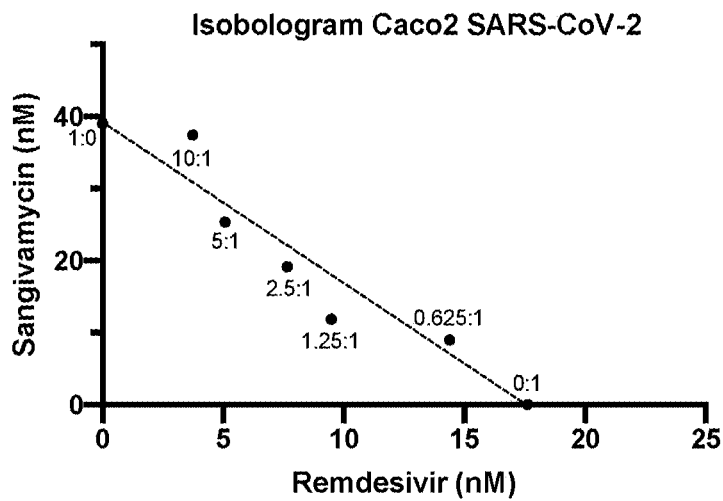

As shown in FIGS. 20A-20C, Caco2 cells infected with SARS-CoV-2 as in FIGS. 15 and 16 were treated with combinations of sangivamycin (S) and remedesivir (R). Based on single drug treatment curves from FIGS. 15C and 16C S:R were established from 10:1, 5:1, 2.5:1, 1.25:1, and 0.625:1, the S concentrations were between 100-0.39 nM and R concentrations 20-0.313 nM. FIG. 20A illustrates the infectivity curves for each S:R relative to sangivamycin concentration with IC$_{50}$ values listed on the right. FIG. 20B illustrates the infectivity curves for each S:R relative to remdesivir concentration with IC$_{50}$ values listed on the right. FIG. 20C illustrates an isobologram plotting the sangivamycin IC$_{50}$ values on the y-axis and the remdesivir IC$_{50}$ values on the x-axis for each constant ratio. The dotted line connects 1:0 (sangivamycin alone) to 0:1 (remdesivir alone). The S:R ratios plot slightly below this line indicative of mild synergy between the two drugs in combination in Caco2 cells.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for treating a *Coronaviridae* infection in a subject in need thereof comprising administering to the subject a combination therapy comprising a composition comprising a compound and a pharmaceutically acceptable carrier and one or more of a vaccine, a small molecule, or an antibody intended for the treatment of a Coronavirus infection;

wherein the compound is selected from a group consisting of:

i) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide having the formula:

Formula IIa

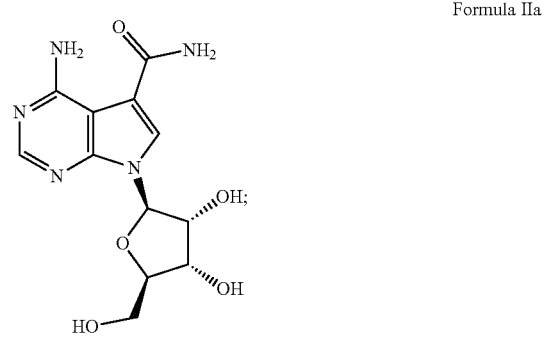 [SMILES: NC(=O)c1cn([C@@H]2O[C@H](CO)[C@@H](O)[C@H]2O)c2ncnc(N)c12]

ii) 4-amino-7-((2R,3R,4S,5R)-3,4-dihydroxy-5-(hydroxymethyl)tetrahydrofuran-2-yl)-7H-pyrrolo[2,3-d]pyrimidine-5carboxamide hydrochloride having the formula:

Formula Ib

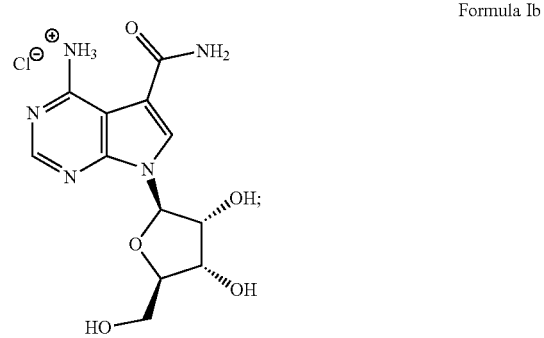 [SMILES: [Cl-] ; NC(=O)c1cn([C@@H]2O[C@H](CO)[C@@H](O)[C@H]2O)c2ncnc([NH3+])c12]

and iii) fixtures thereof;

wherein the compound is administered in an amount from about 0.1 mg/kg to about 1.0 mg/kg of the body mass of the subject.

2. The method according to claim 1, wherein the *Coronaviridae* infection is caused by a *Coronaviridae* virus.

3. The method according to claim 2, wherein the *Coronaviridae* virus is Severe Acute Respiratory Syndrome coronavirus 2 (SARS-CoV-2), or a variant strain of SARS-CoV-2 selected from the group consisting of B.1.1.7 from the U.K., B.1.351 from South Africa, and P.1 from Brazil, or other variant strains of SARS-CoV-2.

4. The method according to claim 1, wherein the small molecule is selected from the group consisting of Remdesivir and Molnupiravir.

5. The method according to claim 4, wherein the small molecule is Remdesivir, and wherein the Remdesivir is administered at a dosage ranging from about 1 mg/kg to about 3 mg/kg of the body mass of the subject.

6. A method of prophylactically treating a subject reasonably suspected of having been exposed, of currently being exposed, or potentially being exposed in the short term to SARS-CoV-2 or a variant strain of SARS-CoV-2 thereof with a combination therapy comprising administering to the subject a composition comprising a compound and a pharmaceutically acceptable carrier, and one or more of a vaccine, a small molecule, or an antibody intended for the treatment of a Coronavirus infection;

wherein the compound is selected from the group consisting of:

i) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide having the formula:

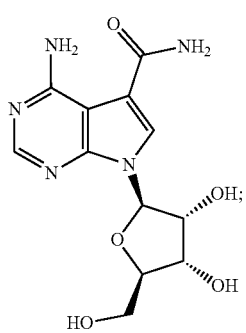

Formula IIa ii) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide hydrochloride having the formula:

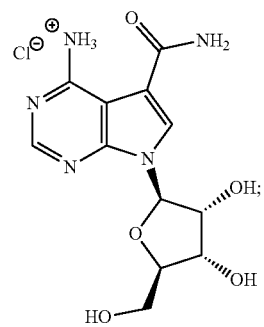

Formula Ib and iii) mixtures thereof;

wherein the compound is administered in an amount from about 0.1 mg/kg to about 1.0 mg/kg of the body mass of the subject.

7. The method according to claim 6, wherein prophylactically treating the subject prevents the spread of SARS-CoV-2 infection or SARS-CoV-2 variant strain infection and the related Coronavirus disease 2019 (COVID-19) or variant disease.

8. The method according to claim 6, wherein the small molecule is selected from the group consisting of Remdesivir and Molnupiravir.

9. The method according to claim 8, wherein the small molecule is Remdesivir, and wherein the Remdesivir is administered at a dosage ranging from about 1 mg/kg to about 3 mg/kg of the body mass of the subject.

10. A method for inhibiting the RNA-dependent RNA polymerase of the Severe Acute Respiratory Syndrome coronavirus 2 (SARS-CoV-2) or SARS-CoV-2 variant strain, comprising administering to a subject having a SARS-CoV-2 or SARS-CoV-2 variant strain infection a combination therapy comprising a composition comprising a compound and a pharmaceutically acceptable carrier and one or more of a vaccine, a small molecule, or an antibody intended for treatment of a Coronavirus infection;

wherein the compound is selected from the group consisting of:

i) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide having the formula:

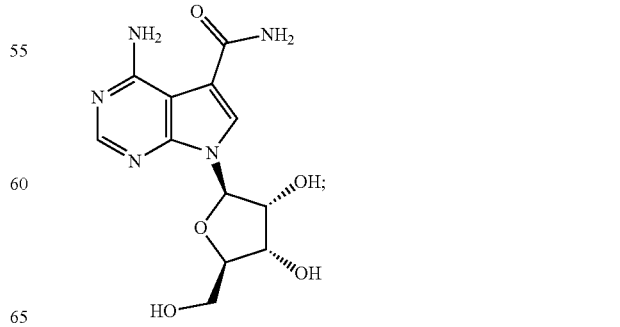

Formula IIa ii) 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide hydrochloride having the formula:

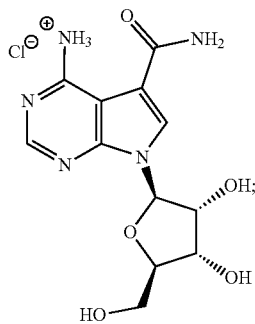

Formula Ib and
iii) mixtures thereof;
wherein the compound is administered in an amount from about 0.1 mg/kg to about .0 mg/kg of the body mass of the subject.

11. The method according to claim 10, wherein the all molecule is selected from the group consisting of Remdesivir and Molnupiravir.

12. The method according to claim 11, wherein the small molecule is Remdesivir, and wherein the Remdesivir is administered at a dosage ranging from about 1mg/kg to about 3 mg/kg of the body mass of the subject.

13. The method according to claim 1, wherein the composition comprises 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide, or the hydrochloride salt thereof, in an amount selected from a group consisting of: from about 5 mg to about 25 mg, from about 5 mg to about 50 mg, and from about 10 mg to about 50 mg.

14. The method according to claim 13, wherein the composition is in the form of an oral-use composition.

15. The method according to claim 13, wherein the composition is in the form of a nasal delivery composition.

16. The composition according to claim 13, wherein the composition is in the form of a sterile injectable composition.

17. The method according to claim 4, wherein the amount of the compound is from about 5 mg to about 25 mg, and wherein the small molecule is Remdesivir; and wherein Remdesivir is administered at a dosage ranging from about 1 mg/kg to about 3 mg/kg of the body mass of the subject.

18. A method for preventing the emergence of a drug-resistant strain of Severe Acute Respiratory Syndrome coronavirus 2 (SARS-CoV-2) or a SARS-CoV-2 variant strain, comprising administering to a subject having a SARS-CoV-2 infection or a SARS-CoV-2 variant strain infection a combination therapy comprising 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide, or the hydrochloride salt thereof, and Remdesivir, wherein the 4-amino-7-((2R,3R,4S,5R)-3,4-dihydroxy-5-(hydroxymethyl)tetrahydrofuran-2-yl)-7H-pyrrolo[2,3-d]pyrimidine-5-carboxamide, or the hydrochloride salt thereof, is administered in a dose selected from a group consisting of from about 5 mg to about 25 mg, from about 5 mg to about 50 mg, and from about 10 mg to about 50 mg; and wherein Remdesivir is administered in an amount ranging from 1 mg/kg to about 3 mg/kg of the body mass of the subject.

* * * * *